US011370770B2

(12) United States Patent
Scheidt et al.

(10) Patent No.: US 11,370,770 B2
(45) Date of Patent: Jun. 28, 2022

(54) 3-ARYLINDAZOLES AS SELECTIVE MEK4 INHIBITORS

(71) Applicant: NORTHWESTERN UNIVERSITY, Evanston, IL (US)

(72) Inventors: Karl A. Scheidt, Evanston, IL (US); Gary E. Schiltz, Naperville, IL (US); Matthew R. Clutter, Deerfield, IL (US); Ada J. Kwong, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 17 days.

(21) Appl. No.: 16/910,433

(22) Filed: Jun. 24, 2020

(65) Prior Publication Data

US 2020/0399241 A1    Dec. 24, 2020

Related U.S. Application Data

(60) Provisional application No. 62/865,384, filed on Jun. 24, 2019.

(51) Int. Cl.
*C07D 401/04* (2006.01)
*C07D 401/12* (2006.01)
*C07D 231/56* (2006.01)
*C07D 405/04* (2006.01)

(52) U.S. Cl.
CPC ......... *C07D 401/04* (2013.01); *C07D 231/56* (2013.01); *C07D 401/12* (2013.01); *C07D 405/04* (2013.01)

(58) Field of Classification Search
CPC .. C07D 401/04; C07D 401/12; C07D 231/56; C07D 405/04
See application file for complete search history.

(56) References Cited

U.S. PATENT DOCUMENTS

2015/0366824 A1* 12/2015 Hyder ................. A61K 31/277
514/520
2016/0168140 A1* 6/2016 Jones ................. C07D 405/04
514/234.5

OTHER PUBLICATIONS

Gao, J Phys Chem B, 2012, vol. 116, 4823-4830. (Year: 2012).*
Diebier, Chem Med Chem, vol. 14, 2019, 615-620. (Year: 2019).*
Pyrde, ACS Med Chem Lett, 2017, vol. 8, 666-671. (Year: 2017).*
Zhang, Tetrahedron Letters, vol. 57, 2016, 2511-2514. (Year: 2016).*
Chen, Org Lett, 2016, vol. 18, 1690-1691. (Year: 2016).*
Naas, J Org Chem, 2014, vol. 79, 7286-7293. (Year: 2014).*
Dubost, Tetrahedron, vol. 70, 2014, 8413-8418. (Year: 2014).*
Liu, Chem Commun, vol. 50, 2014, 5061-5063. (Year: 2014).*
Akintunde A., et al. "MEK and the inhibitors: from bench to bedside." Journal of Hematology & Oncology 6 (2013): 27.

Bembenek, S. D., et al. (2018). Determination of a focused mini kinase panel for early identification of selective kinase inhibitors. Journal of chemical information and modeling, 58(7), 1434-1440.
Cuenda, A. "Mitogen-activated protein kinase kinase 4 (MKK4)." The international journal of biochemistry & cell biology 32.6 (2000): 581-587.
Cunningham, S. C., et al. "Targeted deletion of MKK4 in cancer cells: a detrimental phenotype manifests as decreased experimental metastasis and suggests a counterweight to the evolution of tumor-suppressor loss." Cancer research 66.11 (2006): 5560-5564.
Da-Cunha, E. V. L., et al. "Protoberberine alkaloids." The Alkaloids: Chemistry and Biology 62 (2005): 1-75.
Deibler, K. K., et al. "A chemical probe strategy for interrogating inhibitor selectivity across the mek kinase family." ACS chemical biology 12.5 (2017): 1245-1256.
Deibler, K. K., et al. "Synthesis and Biological Evaluation of 3-Arylindazoles as Selective MEK4 Inhibitors." ChemMedChem 14.6 (Mar. 2019): 615-620.
Derijard, B., et al. "Independent human MAP-kinase signal transduction pathways defined by MEK and MKK isoforms." Science 267.5198 (1995): 682-685.
Friday, B. B., et al. (2008). Advances in targeting the Ras/Raf/MEK/Erk mitogen-activated protein kinase cascade with MEK inhibitors for cancer therapy. Clinical cancer research, 14(2), 342-346.
Hjalgren, T. A., et al. "Glide: a new approach for rapid, accurate docking and scoring. 2. Enrichment factors in database screening." Journal of medicinal chemistry 47.7 (2004): 1750-1759.
Hsueh, C-T et al. "Novel biomarkers for diagnosis, prognosis, targeted therapy and clinical trials." Biomarker Research 1 (2013): 1.
Irwin, J. J., et al. "An aggregation advisor for ligand discovery." Journal of medicinal chemistry 58.17 (2015): 7076-7087.
Kim, N., et al. "A Protoberberine derivative HWY336 selectively inhibits MKK4 and MKK7 in mammalian cells: the importance of activation loop on selectivity." PloS one 9.4 (2014): e91037.
Knight, Z. A., et al. "Features of Selective Kinase Inhibitors." Chemistry & Biology 12.6 (2005): 621-637.
Krishna, S. N., et al. "A fluorescence-based thermal shift assay identifies inhibitors of mitogen activated protein kinase kinase 4." PloS one 8.12 (2013): e81504.
Kwong, A.J. et al. "Design, Synthesis, and Evaluation of MEK4 Inhibitors Against Metastatic Pancreatic Ductal Adenocarcinoma". Poster. Presented at 9th Chicago Organic Symposium. Oct. 20, 2018.
Lee, D. E., et al. "7,3', 4'-Trihydroxyisoflavone, a metabolite of the soy isoflavone daidzein, suppresses ultraviolet B-induced skin cancer by targeting Cot and MKK4." Journal of Biological Chemistry 286.16 (2011): 14246-14256.

(Continued)

*Primary Examiner* — D Margaret M Seaman
(74) *Attorney, Agent, or Firm* — Quarles & Brady LLP

(57) ABSTRACT

Disclosed are indazole compounds and derivatives thereof for use as modulators of the activity of mitogen-activated protein kinase 4 (MEK4). The disclosed compounds include 3-Arylindazoles which may be formulated in pharmaceutical composition for treating cell proliferative diseases and disorders associated with MEK4 activity, including cancer.

25 Claims, 13 Drawing Sheets

(56) References Cited

OTHER PUBLICATIONS

Liu, F., et al. "Targeting ERK, an Achilles' Heel of the MAPK pathway, in cancer therapy." Acta pharmaceutica sinica B 8.4 (2018): 552-562.

Lotan, T. L., et al. "Up-regulation of MKK4, MKK6 and MKK7 during prostate cancer progression: an important role for SAPK signalling in prostatic neoplasia." The Journal of Pathology: A Journal of the Pathological Society of Great Britain and Ireland 212.4 (2007): 386-394.

McGovern, S. L., et al. "A specific mechanism of nonspecific inhibition." Journal of medicinal chemistry 46.20 (2003): 4265-4272.

Micel, L. N., et al. "Antitumor activity of the MEK inhibitor TAK-733 against melanoma cell lines and patient-derived tumor explants." Molecular cancer therapeutics 14.2 (2015): 317-325.

Pavese, J. M., et al. "Mitogen-Activated Protein Kinase Kinase 4 (MAP2K4) Promotes Human Prostate Cancer Metastasis." PLoS ONE 9.7 (2014).

Poplin, E., et al. "Phase III, randomized study of gemcitabine and oxaliplatin versus gemcitabine (fixed-dose rate infusion) compared with gemcitabine (30-minute infusion) in patients with pancreatic carcinoma E6201: a trial of the Eastern Cooperative Oncology Group." Journal of clinical oncology 27.23 (2009): 3778.

Wang, L., et al. "Evidence of MKK4 pro-oncogenic activity in breast and pancreatic tumors." Oncogene 23.35 (2004): 5978-5985.

Wellbrock, C., et al. "The complexity of the ERK/MAP-kinase pathway and the treatment of melanoma skin cancer." Frontiers in cell and developmental biology 4 (2016): 33.

Whitmarsh, A. J., et al. "Role of mitogen-activated protein kinase kinase 4 in cancer." Oncogene 26.22 (2007): 3172-3184.

Xu, L., et al. "MEK4 function, genistein treatment, and invasion of human prostate cancer cells." JNCI: Journal of the National Cancer Institute 101.16 (2009): 1141-1155.

Xu, L., et al. "Precision therapeutic targeting of human cancer cell motility." Nature Communications 9.1 (2018): 2454.

Xue, Z., et al. "MAP3K1 and MAP2K4 mutations are associated with sensitivity to MEK inhibitors in multiple cancer models." Cell research 28.7 (2018): 719-729.

Zhao, Y. et al. "The clinical development of MEK inhibitors." Nature reviews Clinical oncology 11.7 (2014): 385.

\* cited by examiner

3-ARYLINDAZOLES AS SELECTIVE MEK4 INHIBITORS

CROSS-REFERENCE TO RELATED PATENT APPLICATIONS

The present application claims the benefit of priority under 35 U.S.C. 119(e) to U.S. Provisional Patent Application No. 62/865,384, filed on Jun. 24, 2019, the content of which is incorporated herein by reference in its entirety.

STATEMENT REGARDING FEDERALLY SPONSORED RESEARCH OR DEVELOPMENT

This invention was made with government support under CA188015 awarded by the National Institutes of Health. The government has certain rights in the invention.

BACKGROUND

The field of the invention relates to indazole compounds and derivatives thereof for use as inhibitors of mitogen-activated protein kinase 4 (MEK4). In particular, the field of the invention relates to 3-aryl substituted indazole compounds (3-arylindazoles) and derivatives thereof for use as inhibitors of MEK4, which may be formulated as pharmaceutical compositions for treatment of cell proliferative diseases and disorders such as cancer.

Abstract. MEK4 is an upstream kinase in MAPK signaling pathways that phosphorylates p38 MAPK and JNK in response to mitogenic and cellular stress queues. MEK4 is overexpressed and induces metastasis in advanced prostate cancer lesions. However, the value of MEK4 as an oncology target has not been pharmacologically validated because selective chemical probes targeting MEK4 have not been developed. By optimizing this series via structure activity relationships and molecular modelling, the present inventors identified compound 6ff (4-(6-fluoro-2H-indazol-3-yl)benzoic acid), a highly potent and selective MEK4 inhibitor. This series of inhibitors is the first of its kind in both activity and selectivity and will be useful in further defining the role of MEK4 in prostate and other cancers.

Introduction. MAPK signaling cascades are dysregulated in human cancer and inflammatory diseases, and small molecule inhibitors targeting MAPK signaling components are under intense investigation in the clinic. A majority of MEK inhibitors target MEK1/2 including the FDA approved drug trametinib/Mekinist. Most clinically relevant MEK inhibitors today target the MEK1/2 allosteric site and therefore show no activity against MEK3/4/5/6 or 7. As a result, there is a dearth of chemical matter directed at these other MAPK kinase family members, which is surprising given their roles in a host of biological processes. Consequently, their value as therapeutic targets has not been thoroughly investigated and new compounds that are selective for MEK family kinases beyond MEK1/2 could have tremendous potential. Most clinical studies with MEK inhibitors have yielded disappointing results, due at least in part to the paucity of biomarkers of MEK inhibitor sensitivity and toxicity. Bernards and co-workers recently showed data suggesting that cancers having mutations in MEK4 or its upstream kinase MEKK1, which are frequent in tumors of breast, prostate and colon, may respond to MEK inhibitors. Their findings also suggest that MEKK1 and MEK4 are potential drug targets in combination with current MEK inhibitors, in spite of the fact that they are encoded by putative tumor suppressor genes.

MEK4 (also known as MAP2K4, MKK4, SEK1) is a dual-specificity kinase, i.e., it phosphorylates serine/threonine as well as tyrosine residues, and it constitutes a second tier signaling protein of the canonical three-tier MAPK cascade. MEK4 has become a target of interest for the therapeutic inhibition of prostate cancer (PCa) metastasis. Although often described only as an activator of JNK, MEK4 also activates p38α and p38β, which complicates any investigation in this area. MEK4 is overexpressed in advanced PCa lesions and induces invasion and metastasis in PCa. MEK4 also appears to have a similar pro-invasion/pro-metastatic role in several other cancer types, including breast and pancreatic cancers. Through genetic and chemical approaches, MEK4 was shown to increase the invasive potential of PCa cells in vitro by upregulating the production of several matrix metalloproteinases (MMP's) in response to TGF-β treatment. Overexpressing MEK4 increased the number of metastatic deposits observed in a PCa mouse model. These findings present MEK4 as a clinically important therapeutic target and underscore the need to develop selective MEK4 probes for in vivo target validation in advanced cancer model systems.

To date, in the literature there has been minimal advancement in MEK4 inhibitor development. HWY336, a proto-berberine derivative, inhibits both MEK4 and MEK7. HWY336 not only has poor selectivity and only moderate potency, but the pharmacological parameters are not ideal as it is a tetracyclic alkaloid, a compounds class known for promiscuity in biological effects. Trihydroxyisoflavones have also been shown to have effects against MEK4 but not in a selective manner. These isoflavones again are rather non-selective, for example 7, 3', 4'-trihydroxyisoflavone (THIF, 2) also inhibits Cot activity. The current landscape of chemical tools to probe this important kinase further stresses the need to develop selective and pharmacologically robust MEK4 inhibitors.

SUMMARY

Disclosed are indazole compounds and derivative thereof for use as inhibitors of mitogen-activated protein kinase 4 (MEK4). Diseases and disorders treated by the disclosed compounds, pharmaceutical compositions, and methods may include, but are not limited to, cell proliferative diseases and disorders such as cancer.

The disclosed indazole compounds include 3-aryl substituted indazoles compounds, which may be referred to as "3-arylindzoles" and derivatives thereof. The disclosed compounds may be described as having a formula as follows:

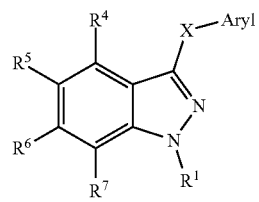

where:
$R^1$ is hydrogen or alkyl (e.g. methyl);
$R^4$, $R^5$, $R^6$, and $R^7$ are independently selected from hydrogen, alkyl (e.g., methyl), alkoxy (e.g., methoxy), halo, or haloalkyl (e.g., trifluoromethyl), optionally where at least one of $R^4$, $R^5$, $R^6$, and $R^7$ is not hydrogen; optionally where at least one of $R^4$, $R^5$, $R^6$, and $R^7$ is not alkyl; optionally where at least one of $R^4$, $R^5$, $R^6$, and $R^7$ is not halo;

X is selected from a bond, or sulfonamide (e.g., —NH—S(O)(O)—), alkylamino (e.g., —NH—CH$_2$—), and alkylcarboxamide (e.g., —NH—C(O)—CH$_2$—);

Aryl is an aryl moiety optionally selected from phenyl, pyridyl, and 1,3-benzodioxolyl; and Aryl is optionally substituted at one or more positions with one or more substituents selected from alkyl (e.g., methyl), alkoxy (e.g., methoxy), hydroxyalkyl (e.g., hydroxymethyl and 1-methyl-hydroxymethyl), aryl (e.g., phenyl), carbonyl, carboxyl, hydroxyl, carboxamido (e.g. H—C(O)—NH—), alkylcarboxamido (e.g., CH$_3$—CH$_2$—C(O)—NH—), alkenylcarboxamido (e.g., CH2=CH—C(O)—NH—), alkylamino-alkenyl-carboxamido (e.g., (CH$_3$)$_2$N—CH$_2$—CH=CH—C(O)—NH—), halo-alkenyl-carboxamido (e.g., Cl—CH$_2$—CH=CH—C(O)—NH—), hydroxyalkyl (e.g., HO—CH$_2$—), halo, carboxyalkyl (HO—C(O)—CH$_2$—), alkylcarboxy ester (e.g., CH$_2$—O—C(O)—), nitro, amino, alkylcarbonyl (e.g., acetyl or CH$_3$—C(O)—), haloalkyl-carbonyl (e.g., CF$_3$—C(O)—), sulfonylamino (e.g., S(O)(O)—NH—), alkyl-sulfonylamino (e.g., CH$_3$—S(O)(O)—NH—), haloalkyl-sulfonylamino (e.g., CF$_3$—S(O)(O)—NH—), cycloalkyl-sulfonylamino (e.g., cyclohexyl-S(O)(O)—NH— or cyclopropyl-S(O)(O)—NH—), pyridinyl-sulfonylamino (e.g., (pyridin-4-yl)-S(O)(O)—NH— or (pyridin-3-yl)-S(O)(O)—NH— or (pyridin-2-yl)-S(O)(O)—NH—), pyrazolinyl-sulfonylamino (e.g., pyrazolin-4-yl-S—(O)(O)—NH—), and N-alkylpyrazolinyl-sulfonylamino (e.g., N-methylpyrazolin-4-yl-S—(O)(O)—NH—), aminosulfonyl (e.g., NH2-S(O)(O)—).

Also contemplated are salts of the disclosed compounds including pharmaceutically acceptable salts of the disclosed compounds. Also contemplated are hydrates of the disclosed compounds including pharmaceutically acceptable hydrates of the disclosed compounds.

Specifically, the disclosed compounds may have a formula:

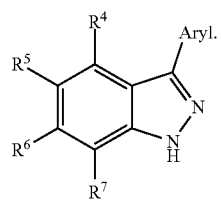

Specifically, the disclosed compounds may have a formula:

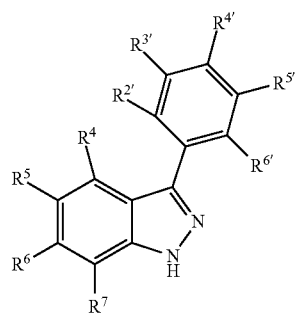

where:

$R^{2'}$, $R^{3'}$, $R^{4'}$, $R^{5'}$, and $R^{6'}$ are independently selected from hydrogen, alkyl (e.g., methyl), alkoxy (e.g., hydroxymethyl and 1-methyl-hydroxymethyl), aryl (e.g., phenyl), carboxyl, hydroxyl, carboxamido (e.g. H—C(O)—NH—), alkylcarboxamido (e.g., CH$_3$—CH$_2$—C(O)—NH—), alkenylcarboxamido (e.g., CH2=CH—C(O)—NH—), alkylamino-alkenyl-carboxamido (e.g., (CH$_3$)$_2$N—CH$_2$—CH=CH—C(O)—NH—), halo-alkenyl-carboxamido (e.g., Cl—CH$_2$—CH=CH—C(O)—NH—), hydroxyalkyl (e.g., HO—CH$_2$—), halo, carboxyalkyl (HO—C(O)—CH$_2$—), nitro, amino, alkylcarbonyl (e.g., acetyl or CH$_3$—C(O)—), haloalkyl-carbonyl (e.g., CF$_3$—C(O)—), sulfonylamino (e.g., S(O)(O)—NH—), alkyl-sulfonylamino (e.g., CH$_3$—S(O)(O)—NH—), haloalkyl-sulfonylamino (e.g., CF$_3$—S(O)(O)—NH—), cycloalkyl-sulfonylamino (e.g., cyclohexyl-S(O)(O)—NH— or cyclopropyl-S(O)(O)—NH—), pyridinyl-sulfonylamino (e.g., pyridin-3-yl-S(O)(O)—NH— or pyridin-3-yl-S(O)(O)—NH—), pyrazolinyl-sulfonylamino (e.g., pyrazolin-4-yl-S—(O)(O)—NH—), and N-alkylpyrazolinyl-sulfonylamino (e.g., N-methylpyrazolin-4-yl-S—(O)(O)—NH—); optionally wherein at least one of $R^{2'}$, $R^{3'}$, $R^{4'}$, $R^{5'}$, and $R^{6'}$ is not hydrogen; and optionally wherein at least one of $R^{2'}$, $R^{3'}$, $R^{4'}$, $R^{5'}$, and $R^{6'}$ is not alkyl.

The disclosed compounds may be formulated as pharmaceutical compositions comprising the compounds or pharmaceutically acceptable salts or pharmaceutically acceptable hydrates thereof together with a pharmaceutically acceptable carrier, excipient, or diluent. The disclosed compounds and pharmaceutical compositions thereof may be utilized in treatment methods for a subject in need thereof. In particular, the disclosed compounds and pharmaceutical compositions thereof may be utilized to treat cell proliferative diseases or disorders such as cancer.

The disclosed compounds and pharmaceutical compositions may be utilized to treat a subject having a disease or disorder that is associated with MEK4 activity, such as a cell proliferative disease or disorder (e.g., cancer) that is associated with MEK4 activity in a subject in need thereof. For example, the disclosed compounds and pharmaceutical compositions may be administered to a subject in need thereof to treat the disease or disorder that is associated with MEK4 activity.

DETAILED DESCRIPTION

Figure 1:
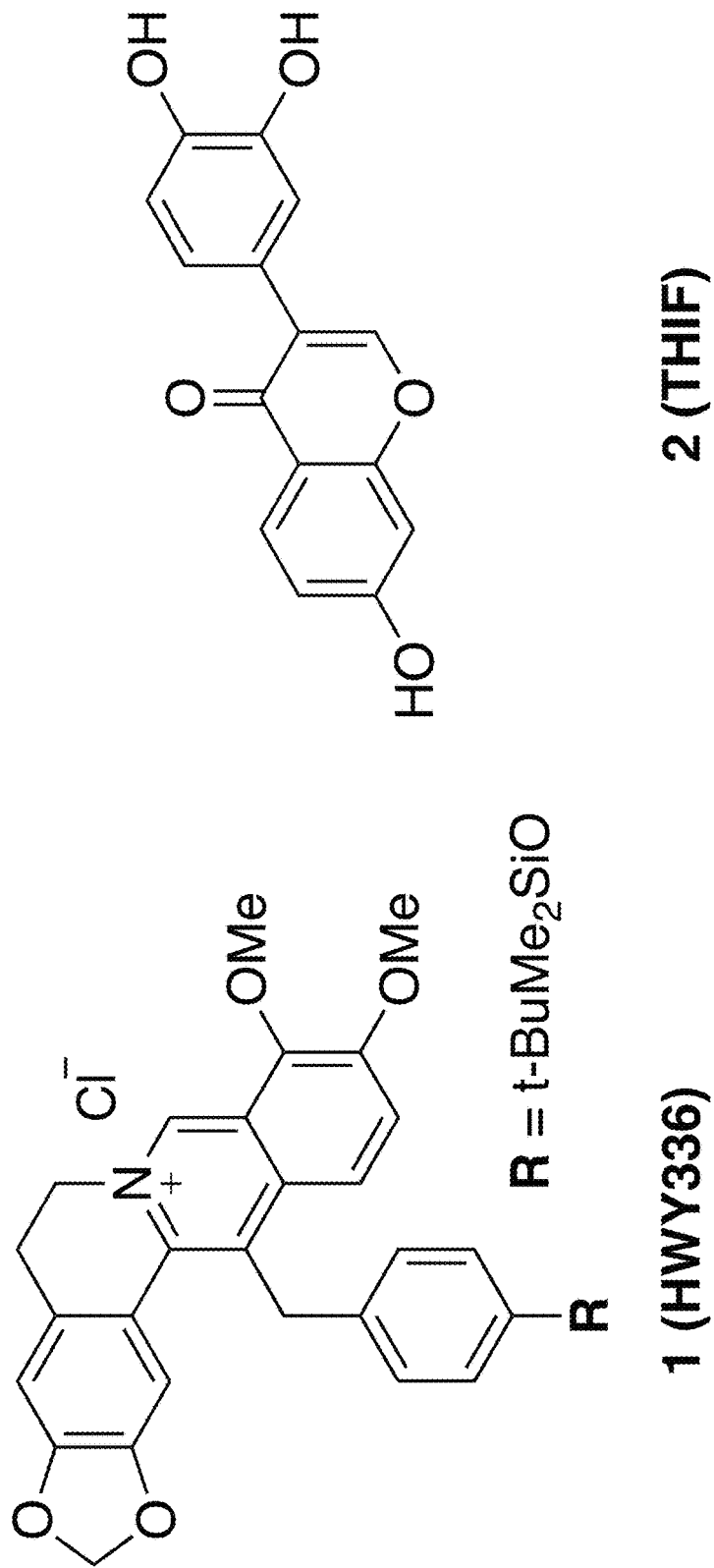
FIG. 1. Structures of previously reported MEK4 inhibitors.

The present invention is described herein using several definitions, as set forth below and throughout the application.

Definitions

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a substituent" should be interpreted to mean "one or more substituents," unless the context clearly dictates otherwise.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

A "subject in need thereof" as utilized herein refers to a subject in need of treatment for a disease or disorder associated with mitogen-activated protein kinase 4 (MEK4) activity. The term "subject" may be used interchangeably with the terms "individual" and "patient" and includes human and non-human mammalian subjects.

Diseases and disorders associated with MEK4 activity may include, but are not limited to, cell proliferative diseases and disorders such as cancer. Cancers may include, but are not limited to, adrenal cancer, anal cancer, bladder cancer, bone cancer, breast cancer, cervical cancer, Chronic Lymphocytic Leukemia (CLL), Chronic Myeloid Leukemia (CML), Chronic Myelomonocytic Leukemia (CMML), colorectal cancer, endometrial cancer, esophagus cancer, gallbladder cancer, carcinoid tumors, kidney cancer, leukemia, liver cancer, lung cancer, lymphoma, nasopharyngel cancer, non-small cell lung cancer, ovarian cancer, pancreatic cancer, penile cancer, pituitary tumors, prostate cancer, skin cancer, small cell lung cancer, small intestine cancer, stomach cancer, testicular cancer, thymus cancer, thyroid cancer, vaginal cancer, and vulvar cancer.

Chemical Entities

New chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of straight-chain or branched alkyl group (i.e., a diradical of straight-chain or branched C1-C6 alkyl group). Exemplary alkylene groups include, but are not limited to —CH$_2$—, —CH$_2$CH$_2$—, —CH$_2$CH$_2$CH$_2$—, —CH(CH$_3$)CH$_2$—, —CH$_2$CH(CH$_3$)CH$_2$—, —CH(CH$_2$CH$_3$)CH$_2$—, and the like.

The term "halo" refers to a halogen atom or halogen radical (e.g., —F, —Cl, —Br, or —I).

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido or carboxamido, amidino, amino, aryl, arylalkyl, azido, carbamate, carbonate, carboxy, carboxyamido, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloheteroalkyl" refers to a monovalent saturated cyclic, bicyclic, or bridged cyclic hydrocarbon group of 3-12, 3-8, 4-8, or 4-6 carbons in which at least one carbon of the cycloalkane is replaced with a heteroatom such as, for example, N, O, and/or S.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido or carboxamido, amidino, amino, aryl, arylalkyl, azido, carbamate, carbonate, carboxy, carboxyamido, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido or carboxamido, carboxylic acid, —C(O)alkyl, —CO$_2$alkyl, carbonyl, carboxyl, carboxyamido, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently hydrogen, alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" (or "carboxyamido") or "amidyl" as used herein refers to a radical of the form —R$^1$C(O)N(R$^2$)—, —R$^1$C(O)N(R$^2$)R$^3$—, —C(O)NR$^2$R$^3$, or —C(O)NH$_2$, wherein R$^1$, R$^2$ and R$^3$, for example, are each independently hydrogen, alkyl, alkoxy, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "−" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an R enantiomer of a given compound).

Use of the Disclosed Compounds for Modulating Mitogen-Activated Protein Kinase 4 (MEK4) Activity The disclosed compounds may exhibit one or more biological activities. In some embodiments, the disclosed compounds may modulate the activity of mitogen-activated protein kinase 4 (MEK4). For example, in some embodiments, the disclosed compounds inhibit the activity of MEK4 by at least 50%, 60%, 70%, 80%, 90%, 95%, 96%, 97%, 98%, or 99% at a concentration of less than about 100 $\mu M$, 50 $\mu M$, 10 $\mu M$, 1 $\mu M$, 0.1 $\mu M$, 0.05 $\mu M$, 0.01 $\mu M$, 0.005 $\mu M$, 0.001 $\mu M$, or less. The disclosed compounds may inhibit the growth of cells that express MEK4 (preferably by at least 50%, 60%, 70%, 80%, 90%, 95%, 96%, 97%, 98%, or 99% at a concentration of less than about 100 $\mu M$, 50 $\mu M$, 10 $\mu M$, 1 $\mu M$, 0.1 $\mu M$, 0.05 $\mu M$, 0.01 $\mu M$, 0.005 $\mu M$, 0.001 $\mu M$, or less). The disclosed compounds may not inhibit the growth of cells that do not express MEK4 (preferably by not more than 50%, 40%, 30%, 20%, 10%, 5%, 4%, 3%, 2% or less at a concentration of greater than about 0.001 $\mu M$, 0.005 $\mu M$, 0.01 $\mu M$, 0.5 $\mu M$, 0.1 $\mu M$, 1.0 $\mu M$, 10 $\mu M$, and 100 $\mu M$ or higher). Concentration ranges also are contemplated herein, for example, a concentration range bounded by end-point concentrations selected from 0.001 $\mu M$, 0.005 $\mu M$, 0.01 $\mu M$, 0.5 $\mu M$, 0.1 $\mu M$, 1.0 $\mu M$, 10 $\mu M$, and 100 $\mu M$.

Cell proliferation and inhibition thereof by the presently disclosed compounds may be assessed by cell viability methods disclosed in the art including colorimetric assays that utilize dyes such as MTT, XTT, and MTS to assess cell viability. Preferably, the disclosed compounds have an $IC_{50}$ of less than about 10 $\mu M$, 5 $\mu M$, 1 $\mu M$, 0.5 $\mu M$, 0.01 $\mu M$, 0.005 $\mu M$, 0.001 $\mu M$ or lower in the selected assay.

Pharmaceutical Compositions, Formulations, and Methods of Treatment for Diseases and Disorders Associated with Mitogen-Activated Protein Kinase 4 (MEK4) Activity The compounds employed in the compositions and methods disclosed herein may be administered as pharmaceutical compositions and, therefore, pharmaceutical compositions incorporating the compounds are considered to be embodiments of the compositions disclosed herein. Such compositions may take any physical form which is pharmaceutically acceptable; illustratively, they can be orally administered pharmaceutical compositions. Such pharmaceutical compositions contain an effective amount of a disclosed compound, which effective amount is related to the daily dose of the compound to be administered. Each dosage unit may contain the daily dose of a given compound or each dosage unit may contain a fraction of the daily dose, such as one-half or one-third of the dose. The amount of each compound to be contained in each dosage unit can depend, in part, on the identity of the particular compound chosen for the therapy and other factors, such as the indication for which it is given. The pharmaceutical compositions disclosed herein may be formulated so as to provide quick, sustained, or delayed release of the active ingredient after administration to the patient by employing well known procedures.

In some embodiments, the compounds disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 $\mu M$, 0.005 $\mu M$, 0.01 $\mu M$, 0.5 $\mu M$, 0.1 $\mu M$, 1.0 $\mu M$, 10 $\mu M$, and 100 $\mu M$ (e.g., 0.1 $\mu M$-1.0 $\mu M$).

The disclosed compounds and pharmaceutical compositions comprising the disclosed compounds may be administered in methods of treating a subject in need thereof. For example, in the methods of treatment a subject in need thereof may include a subject having a cell proliferative disease, disorder, or condition such as cancer.

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds may include doses falling within dose ranges having as end-points any of these disclosed doses (e.g., 2.5 mg-200 mg).

In some embodiments of the disclosed treatment methods, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds for achieving therapy in the disclosed methods of treatment may include dose levels falling within ranges having as end-points any of these disclosed dose levels (e.g., 500-2000 ng/kg body weight of the subject).

The compounds for use according to the methods of disclosed herein may be administered as a single compound or a combination of compounds. For example, a compound that modulates MEK4 activity may be administered as a single compound or in combination with another compound that modulates MEK4 activity or that has a different pharmacological activity.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, α-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

The particular counter-ion forming a part of any salt of a compound disclosed herein is may not be critical to the activity of the compound, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The pharmaceutical compositions may be utilized in methods of treating a disease or disorder associated MEK4 activity. As used herein, the terms "treating" or "to treat" each mean to alleviate symptoms, eliminate the causation of resultant symptoms either on a temporary or permanent basis, and/or to prevent or slow the appearance or to reverse the progression or severity of resultant symptoms of the named disease or disorder. As such, the methods disclosed herein encompass both therapeutic and prophylactic administration.

As used herein the term "effective amount" refers to the amount or dose of the compound, upon single or multiple dose administration to the subject, which provides the desired effect in the subject under diagnosis or treatment. The disclosed methods may include administering an effective amount of the disclosed compounds (e.g., as present in a pharmaceutical composition) for treating a disease or disorder associated with MEK4 activity.

An effective amount can be readily determined by the attending diagnostician, as one skilled in the art, by the use of known techniques and by observing results obtained under analogous circumstances. In determining the effective amount or dose of compound administered, a number of factors can be considered by the attending diagnostician, such as: the species of the subject; its size, age, and general health; the degree of involvement or the severity of the disease or disorder involved; the response of the individual subject; the particular compound administered; the mode of administration; the bioavailability characteristics of the preparation administered; the dose regimen selected; the use of concomitant medication; and other relevant circumstances.

A typical daily dose may contain from about 0.01 mg/kg to about 100 mg/kg (such as from about 0.05 mg/kg to about 50 mg/kg and/or from about 0.1 mg/kg to about 25 mg/kg) of each compound used in the present method of treatment.

Compositions can be formulated in a unit dosage form, each dosage containing from about 1 to about 500 mg of each compound individually or in a single unit dosage form, such as from about 5 to about 300 mg, from about 10 to about 100 mg, and/or about 25 mg. The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

Oral administration is an illustrative route of administering the compounds employed in the compositions and methods disclosed herein. Other illustrative routes of administration include transdermal, percutaneous, intravenous, intramuscular, intranasal, buccal, intrathecal, intracerebral, or intrarectal routes. The route of administration may be varied in any way, limited by the physical properties of the compounds being employed and the convenience of the subject and the caregiver.

As one skilled in the art will appreciate, suitable formulations include those that are suitable for more than one route of administration. For example, the formulation can be one that is suitable for both intrathecal and intracerebral administration. Alternatively, suitable formulations include those that are suitable for only one route of administration as well as those that are suitable for one or more routes of administration, but not suitable for one or more other routes of administration. For example, the formulation can be one that is suitable for oral, transdermal, percutaneous, intravenous, intramuscular, intranasal, buccal, and/or intrathecal administration but not suitable for intracerebral administration.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches, and suspensions. In general, compositions contain from about 0.5% to about 50% of the compound in total, depending on the desired doses and the type of composition to be used. The amount of the compound, however, is best defined as the "effective amount", that is, the amount of the compound which provides the desired dose to the patient in need of such treatment. The activity of the compounds employed in the compositions and methods disclosed herein are not believed to depend greatly on the nature of the composition, and, therefore, the compositions can be chosen and formulated primarily or solely for convenience and economy.

Capsules are prepared by mixing the compound with a suitable diluent and filling the proper amount of the mixture in capsules. The usual diluents include inert powdered substances (such as starches), powdered cellulose (especially crystalline and microcrystalline cellulose), sugars (such as fructose, mannitol and sucrose), grain flours, and similar edible powders.

Tablets are prepared by direct compression, by wet granulation, or by dry granulation. Their formulations usually incorporate diluents, binders, lubricants, and disintegrators (in addition to the compounds). Typical diluents include, for example, various types of starch, lactose, mannitol, kaolin, calcium phosphate or sulfate, inorganic salts (such as sodium chloride), and powdered sugar. Powdered cellulose derivatives can also be used. Typical tablet binders include substances such as starch, gelatin, and sugars (e.g., lactose, fructose, glucose, and the like). Natural and synthetic gums can also be used, including acacia, alginates, methylcellulose, polyvinylpyrrolidine, and the like. Polyethylene glycol, ethylcellulose, and waxes can also serve as binders.

Tablets can be coated with sugar, e.g., as a flavor enhancer and sealant. The compounds also may be formulated as chewable tablets, by using large amounts of pleasant-tasting substances, such as mannitol, in the formulation. Instantly dissolving tablet-like formulations can also be employed, for example, to assure that the patient consumes the dosage form and to avoid the difficulty that some patients experience in swallowing solid objects.

A lubricant can be used in the tablet formulation to prevent the tablet and punches from sticking in the die. The lubricant can be chosen from such slippery solids as talc, magnesium and calcium stearate, stearic acid, and hydrogenated vegetable oils.

Tablets can also contain disintegrators. Disintegrators are substances that swell when wetted to break up the tablet and release the compound. They include starches, clays, celluloses, algins, and gums. As further illustration, corn and potato starches, methylcellulose, agar, bentonite, wood cellulose, powdered natural sponge, cation-exchange resins, alginic acid, guar gum, citrus pulp, sodium lauryl sulfate, and carboxymethylcellulose can be used.

Compositions can be formulated as enteric formulations, for example, to protect the active ingredient from the strongly acid contents of the stomach. Such formulations can be created by coating a solid dosage form with a film of a polymer which is insoluble in acid environments and soluble in basic environments. Illustrative films include cellulose acetate phthalate, polyvinyl acetate phthalate, hydroxypropyl methylcellulose phthalate, and hydroxypropyl methylcellulose acetate succinate.

Transdermal patches can also be used to deliver the compounds. Transdermal patches can include a resinous composition in which the compound will dissolve or partially dissolve; and a film which protects the composition and which holds the resinous composition in contact with the skin. Other, more complicated patch compositions can also be used, such as those having a membrane pierced with a plurality of pores through which the drugs are pumped by osmotic action.

As one skilled in the art will also appreciate, the formulation can be prepared with materials (e.g., actives excipients, carriers (such as cyclodextrins), diluents, etc.) having properties (e.g., purity) that render the formulation suitable for administration to humans. Alternatively, the formulation can be prepared with materials having purity and/or other properties that render the formulation suitable for administration to non-human subjects, but not suitable for administration to humans.

3-Arylindazoles as Selective Inhibitors of Mitogen-Activated Kinase 4 (MEK4)

The subject matter disclosed herein relates to indazole compounds and uses thereof. Particularly disclosed are 3-ayrlindazole compounds, optionally which may be substituted at one or more positions, and the use thereof for modulating the activity of kinases such as mitogen-activated kinase 4 (MEK4) in a subject in need thereof.

In some embodiments, the disclosed compounds may be of a formula:

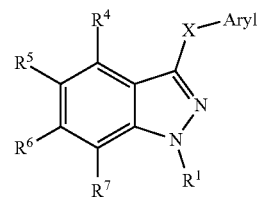

where:

R¹ is hydrogen or alkyl (e.g. methyl);

R⁴, R⁵, R⁶, and R⁷ are independently selected from hydrogen, alkyl (e.g., methyl), alkoxy (e.g., methoxyl), halo, or haloalkyl (e.g., trifluoromethyl), optionally where at least one of R⁴, R⁵, R⁶, and R⁷ is not hydrogen; optionally where at least one of R⁴, R⁵, R⁶, and R⁷ is not alkyl; optionally where at least one of R⁴, R⁵, R⁶, and R⁷ is not halo;

X is selected from a bond, or sulfonamide (e.g., —NH—S(O)(O)—), alkylamino (e.g., —NH—CH₂—), and alkylcarboxamide (e.g., —NH—C(O)—CH₂—);

Aryl is an aryl moiety optionally selected from phenyl, pyridyl, and 1,3-benzodioxolyl; and Aryl is optionally substituted at one or more positions with one or more substituents selected from alkyl (e.g., methyl), alkoxy (e.g., methoxy), hydroxyalkyl (e.g., hydroxymethyl and 1-methyl-hydroxymethyl), aryl (e.g., phenyl), carbonyl, carboxyl, hydroxyl, carboxamido (e.g. H—C(O)—NH—), alkylcarboxamido (e.g., CH₃—CH₂—C(O)—NH—), alkenylcarboxamido (e.g., CH2=CH—C(O)—NH—), alkylamino-alkenyl-carboxamido (e.g., (CH₃)₂N—CH₂—CH=CH—C(O)—NH—), halo-alkenyl-carboxamido (e.g., Cl—CH₂—CH=CH—C(O)—NH—), hydroxyalkyl (e.g., HO—CH₂—), halo, carboxyalkyl (HO—C(O)—CH₂—), alkylcarboxy ester (e.g., CH₂—O—C(O)—), nitro, amino, alkylcarbonyl (e.g., acetyl or CH₃—C(O)—), haloalkyl-carbonyl (e.g., CF₃—C(O)—), sulfonylamino (e.g., S(O)(O)—NH—), alkyl-sulfonylamino (e.g., CH₃—S(O)(O)—NH—), haloalkyl-sulfonylamino (e.g., CF₃—S(O)(O)—NH—), cycloalkyl-sulfonylamino (e.g., cyclohexyl-S(O)(O)—NH— or cyclopropyl-S(O)(O)—NH—), pyridinyl-sulfonylamino (e.g., (pyridin-4-yl)-S(O)(O)—NH— or (pyridin-3-yl)-S(O)(O)—NH— or (pyridin-2-yl)-S(O)(O)—NH—), pyrazolinyl-sulfonylamino (e.g., pyrazolin-4-yl-S—(O)(O)—NH—), and N-alkylpyrazolinyl-sulfonylamino (e.g., N-methylpyrazolin-4-yl-S—(O)(O)—NH—), aminosulfonyl (e.g., NH₂—S(O)(O)—).

In some embodiments, the compounds have a formula as follows, or a salt or hydrate thereof:

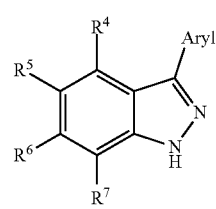

where:

R⁴, R⁵, R⁶, and R⁷ are independently selected from hydrogen, alkyl, alkoxy, halo, or haloalkyl, optionally wherein at least one of R⁴, R⁵, R⁶, and R⁷ is not hydrogen; optionally wherein at least one of R⁴, R⁵, R⁶, and R⁷ is not alkyl (e.g., wherein R and/or R⁶ are not alkyl); optionally wherein at least one of R⁴, R⁵, R⁶, and R⁷ is not halo (e.g., wherein R⁵ is not halo).

In some embodiments, the compounds have a formula as follows, or a salt or hydrate thereof:

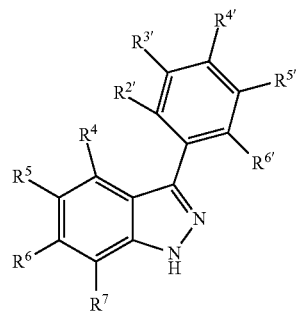

where R²', R³', R⁴', R⁵', and R⁶' are independent selected from hydrogen, alkyl (e.g., methyl), alkoxy (e.g., hydroxymethyl and 1-methyl-hydroxymethyl), aryl (e.g., phenyl), carboxyl, hydroxyl, carboxamido (e.g. H—C(O)—NH—), alkylcarboxamido (e.g., CH₃—CH₂—C(O)—NH—), alkenylcarboxamido (e.g., CH2=CH—C(O)—NH—), alkylamino-alkenyl-carboxamido (e.g., (CH₃)₂N—CH₂—CH=CH—C(O)—NH—), halo-alkenyl-carboxamido (e.g., Cl—CH₂—CH=CH—C(O)—NH—), hydroxyalkyl (e.g., HO—CH₂—), halo, carboxyalkyl (HO—C(O)—CH₂—), nitro, amino, alkylcarbonyl (e.g., acetyl or CH₃—C(O)—), haloalkyl-carbonyl (e.g., CF₃—C(O)—), sulfonylamino (e.g., S(O)(O)—NH—), alkyl-sulfonylamino (e.g., CH₃—S(O)(O)—NH—), haloalkyl-sulfonylamino (e.g., CF₃—S(O)(O)—NH—), cycloalkyl-sulfonylamino (e.g., cyclohexyl-S(O)(O)—NH— or cyclopropyl-S(O)(O)—NH—), pyridinyl-sulfonylamino (e.g., pyridin-3-yl-S(O)(O)—NH— or pyridin-3-yl-S(O)(O)—NH—), pyrazolinyl-sulfonylamino (e.g., pyrazolin-4-yl-S—(O)(O)—NH—), and N-alkylpyrazolinyl-sulfonylamino (e.g., N-methylpyrazolin-4-yl-S—(O)(O)—NH—); optionally wherein at least one of R²', R³', R⁴', R⁵', and R⁶' is not hydrogen; and optionally wherein at least one of R²', R³', R⁴', R⁵', and R⁶' is not alkyl.

In some embodiments, the compounds have a formula as follows, or a salt or hydrate thereof:

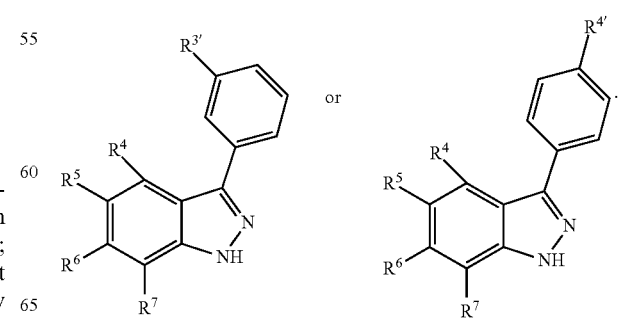

In some embodiments, the compounds have a formula as follows, or a salt or hydrate thereof:

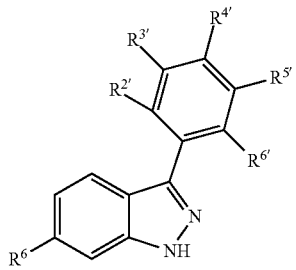

In some embodiments the compounds have a formula as follows, or a salt or hydrate thereof:

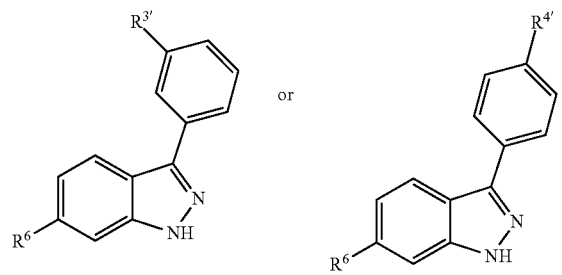

wherein optionally $R^6$ is halo (e.g., fluoro).

In some embodiments, the compounds have a formula as follows, or a salt or hydrate thereof:

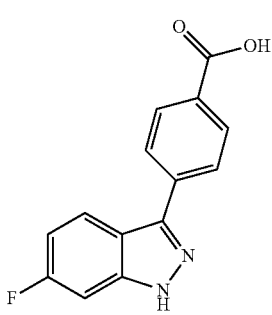 [SMILES: O=C(O)c1ccc(-c2n[nH]c3cc(F)ccc23)cc1]

In some embodiments, the compounds have a formula as follows, or a salt or hydrate thereof:

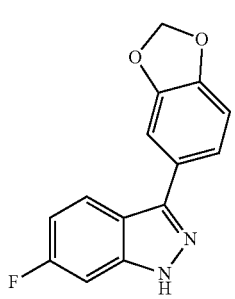 [SMILES: Fc1ccc2c(-c3ccc4c(c3)OCO4)n[nH]c2c1]

In some embodiments, the 3-Arylindazoles may include compounds having a formula selected from:

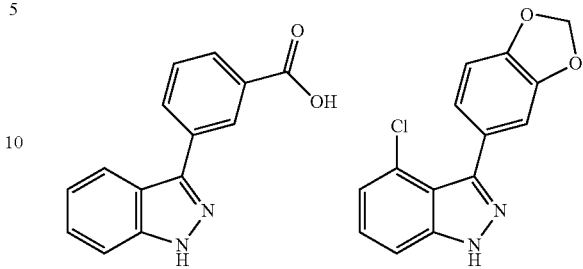

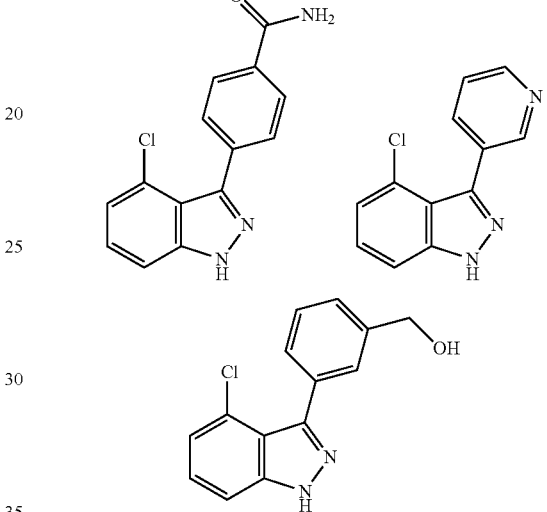

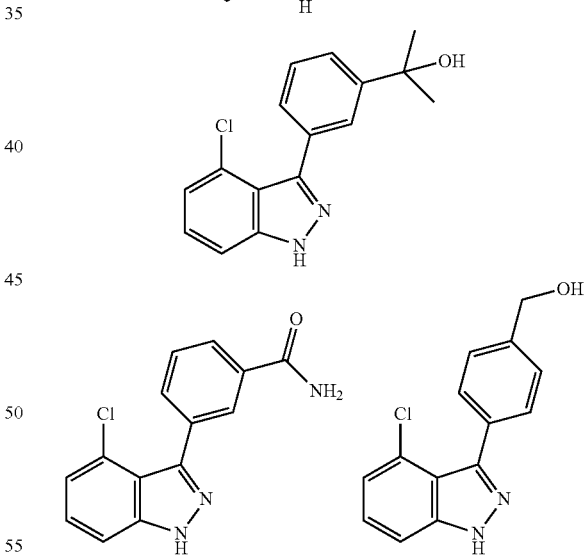

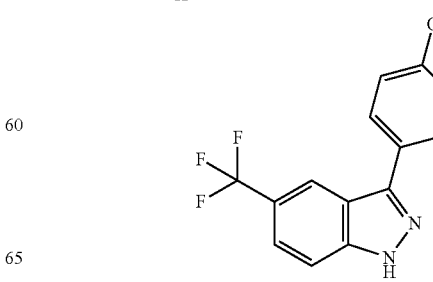

-continued
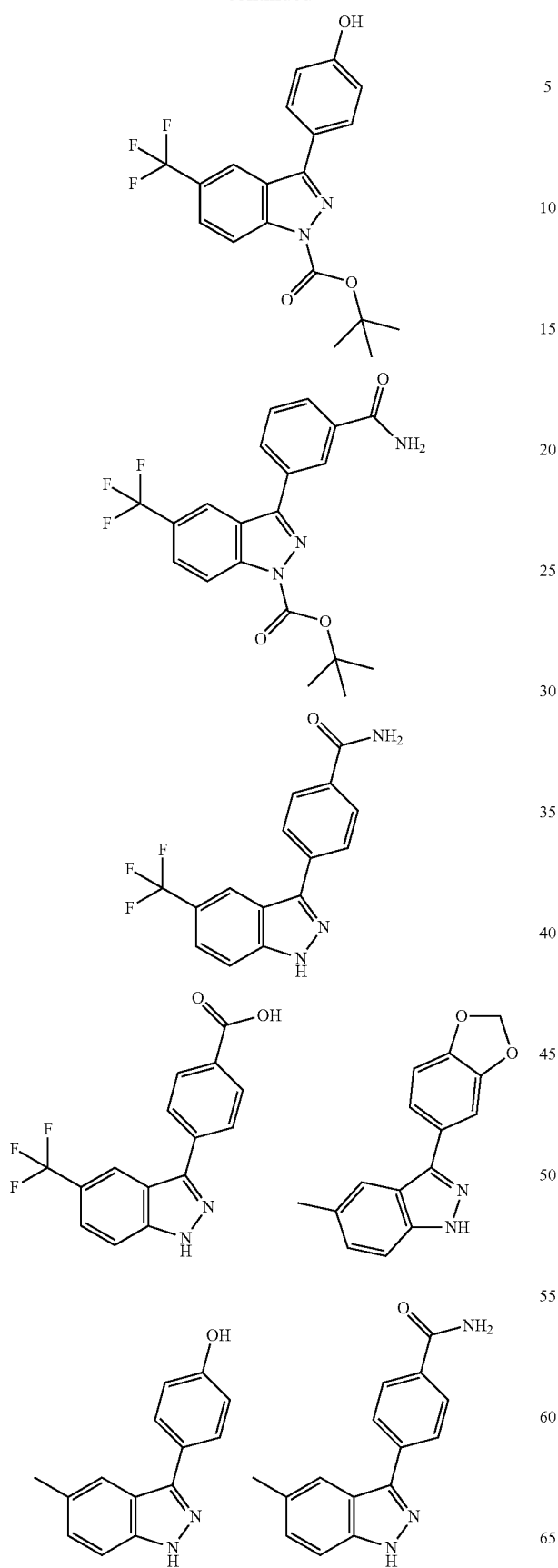
-continued
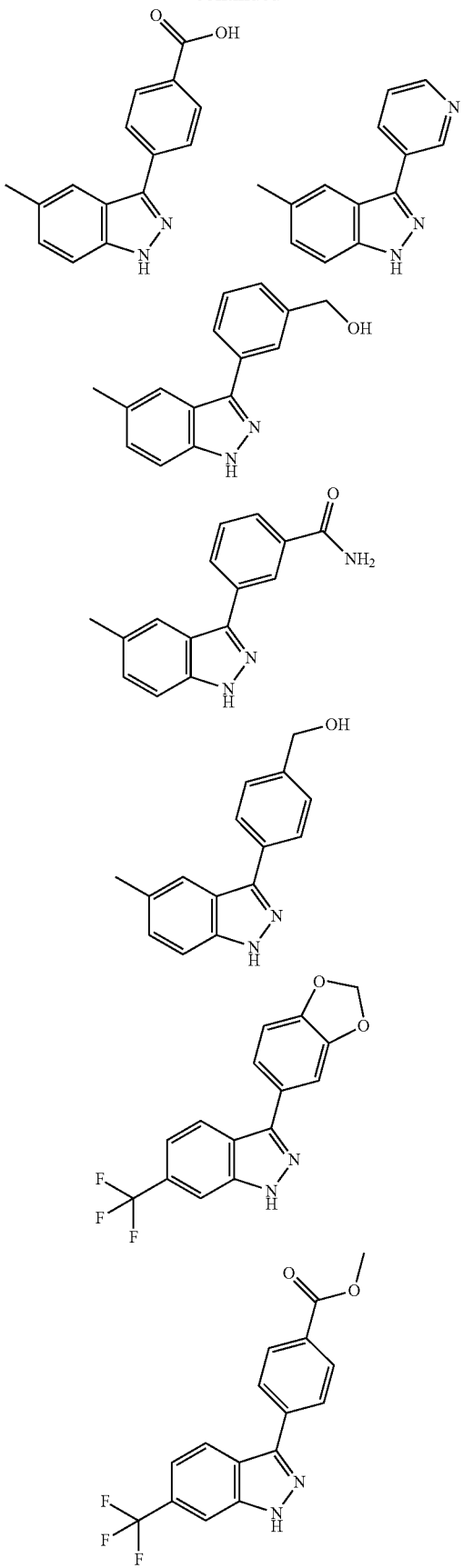

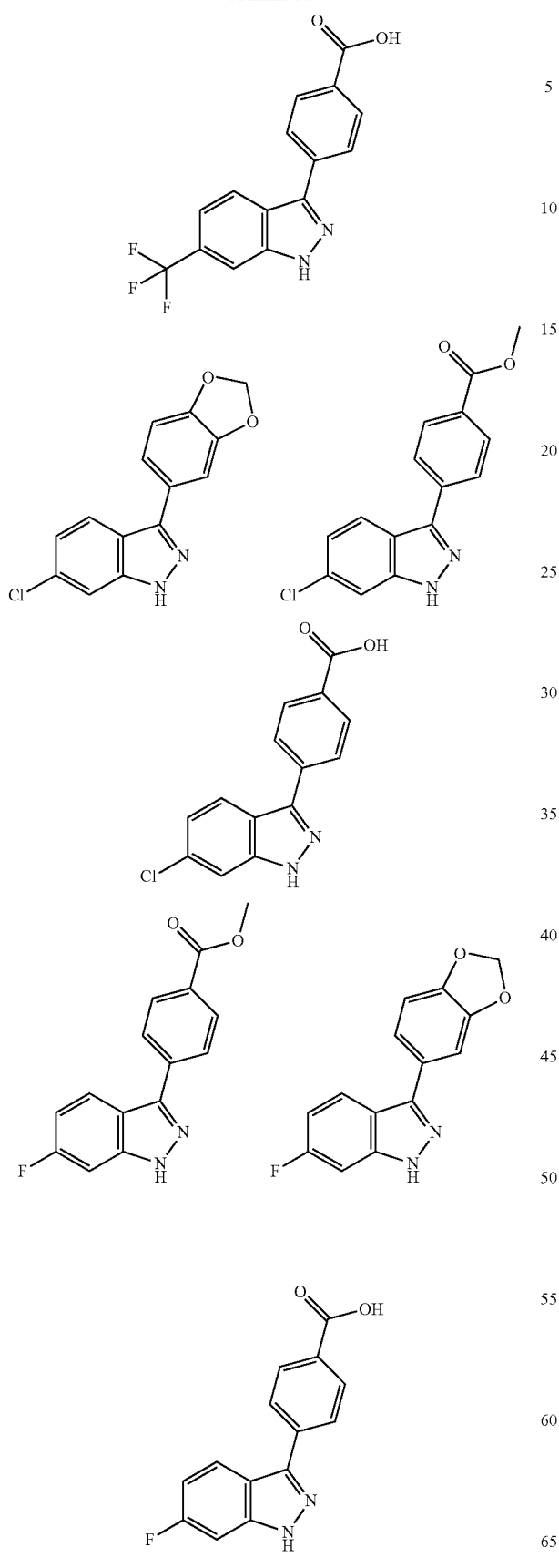
In some embodiments, the 3-Arylindazoles may include compounds having a formula selected from:
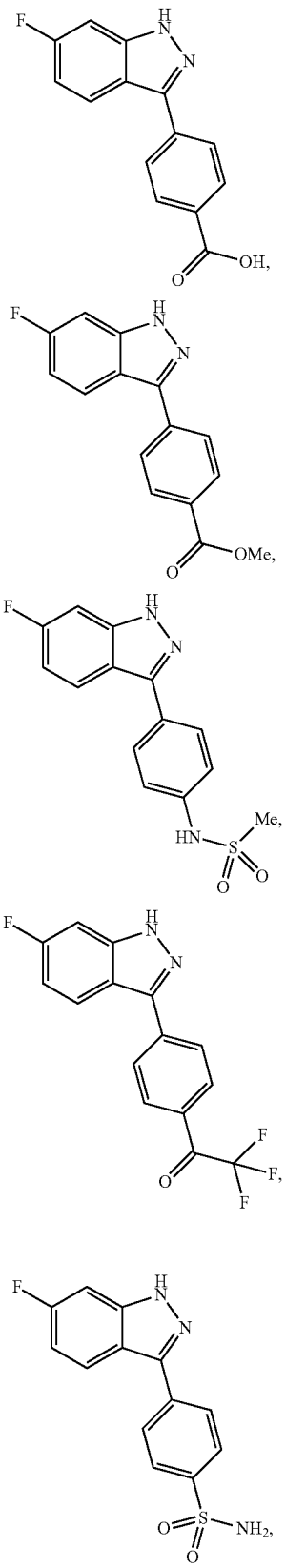

23

-continued

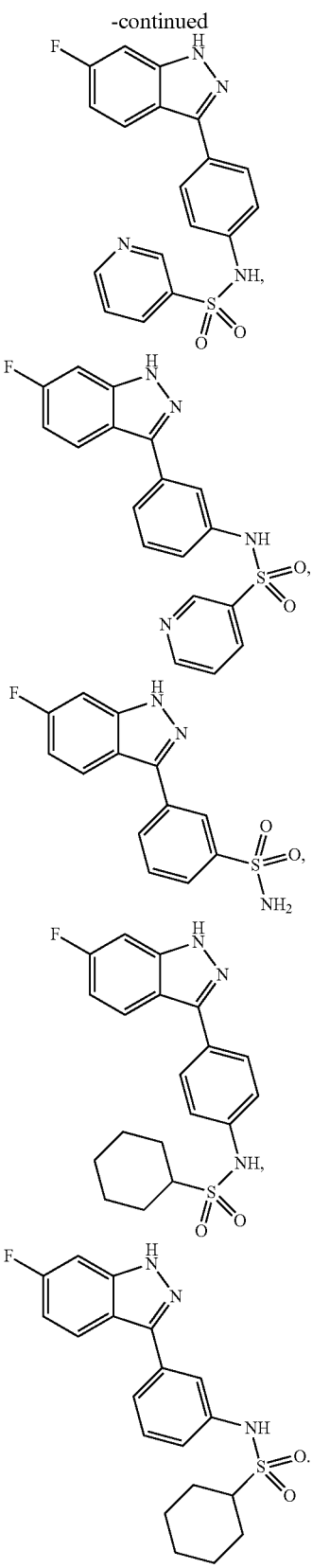

The disclosed compounds, salts thereof, and/or hydrates thereof may be formulated as pharmaceutical compositions comprising the compounds, salts thereof, and/or hydrates thereof, in a pharmaceutically acceptable carrier. The pharmaceutical compositions may be formulated for treating diseases or disorders associated with mitogen-activated protein kinase 4 (MEK4) activity in a subject in need thereof.

In some embodiments, the disclosed compounds and pharmaceutical compositions may be utilized for treating a subject having a cell proliferative disease, disorder, such as prostate, breast or pancreatic cancer associated with mitogen-activated protein kinase 4 (MEK4) activity, the method comprising administering to the subject the compounds and/or the pharmaceutical compositions. In these methods, the subject may be administered an amount of the compound sufficient to modulate MEK4 activity.

ILLUSTRATIVE EMBODIMENTS

The following Examples are illustrative and should not be interpreted to limit the scope of the claimed subject matter.

Embodiment 1

A compound of the following formula or a salt or hydrate thereof:

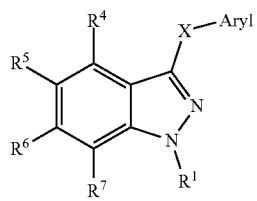

where:
$R^1$ is hydrogen or alkyl (e.g. methyl);
$R^4$, $R^5$, $R^6$, and $R^7$ are independently selected from hydrogen, alkyl (e.g., methyl), alkoxy (e.g., methoxyl), halo, or haloalkyl (e.g., trifluoromethyl), optionally where at least one of $R^4$, $R^5$, $R^6$, and $R^7$ is not hydrogen; optionally where at least one of $R^4$, $R^5$, $R^6$, and $R^7$ is not alkyl; optionally where at least one of $R^4$, $R^5$, $R^6$, and $R^7$ is not halo;
X is a bond, sulfonamide (e.g., —NH—S(O)(O)—), alkylamino (e.g., —NH—CH$_2$—), alkylcarboxamide (e.g., —NH—C(O)—CH$_2$—);
Aryl is phenyl, pyridyl, or 1,3-benzodioxolyl; and
Aryl is optionally substituted at one or more positions with one or more substituents selected from alkyl (e.g., methyl), alkoxy (e.g., methoxy), hydroxyalkyl (e.g., hydroxymethyl and 1-methyl-hydroxymethyl), aryl (e.g., phenyl), carbonyl, carboxyl, hydroxyl, carboxamido (e.g. H—C(O)—NH—), alkylcarboxamido (e.g., CH$_3$—CH$_2$—C(O)—NH—), alkenylcarboxamido (e.g., CH2=CH—C(O)—NH—), alkylamino-alkenyl-carboxamido (e.g., (CH$_3$)$_2$N—CH$_2$—CH=CH—C(O)—NH—), halo-alkenyl-carboxamido (e.g., Cl—CH$_2$—CH=CH—C(O)—NH—), hydroxyalkyl (e.g., HO—CH$_2$—), halo, carboxyalkyl (HO—C(O)—CH$_2$—), alkylcarboxy ester (e.g., CH$_2$—O—C(O)—), nitro, amino, alkylcarbonyl (e.g., acetyl or CH$_3$—C(O)—), haloalkyl-carbonyl (e.g., CF$_3$—C(O)—), sulfonylamino (e.g., S(O)(O)—NH—), alkyl-sulfonylamino (e.g., CH$_3$—S(O)(O)—NH—), haloalkyl-sulfonylamino (e.g., CF$_3$—S(O)(O)—NH—), cycloalkyl-sulfonylamino (e.g., cyclohexyl-S(O)(O)—NH— or cyclopropyl-S(O)(O)—NH—), pyridinyl-sulfonylamino (e.g., (pyridin-4-yl)-S (O)(O)—NH— or (pyridin-3-yl)-S(O)(O)—NH— or (pyridin-2-yl)-S(O)(O)—NH—), pyrazolinyl-sulfonylamino (e.g., pyrazolin-4-yl-S—(O)(O)—NH—), and N-alkylpyrazolinyl-sulfonylamino (e.g., N-methylpyrazolin-4-yl-S—(O)(O)—NH—), aminosulfonyl (e.g., NH$_2$—S(O)(O)—).

Embodiment 2

The compound of embodiment 1 of a formula:

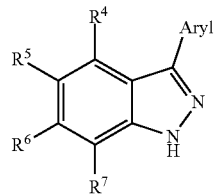

wherein:
$R^4$, $R^5$, $R^6$, and $R^7$ are independently selected from hydrogen, alkyl, alkoxy (e.g., methoxy), halo, or haloalkyl (e.g., trifluoromethyl), optionally wherein at least one of $R^4$, $R^5$, $R^6$, and $R^7$ is not hydrogen; optionally wherein at least one of $R^4$, $R^5$, $R^6$, and $R^7$ is not alkyl (e.g., wherein $R^5$ and/or $R^6$ are not alkyl); optionally wherein at least one of $R^4$, $R^5$, $R^6$, and $R^7$ is not halo (e.g., wherein $R^5$ is not halo).

Embodiment 3

The compound of embodiment 1 or embodiment 2 of a formula:

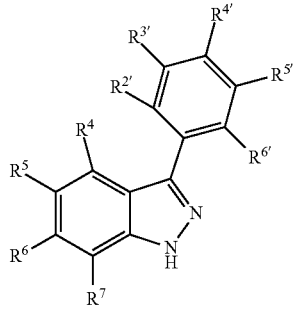

wherein:
$R^{2'}$, $R^{3'}$, $R^{4'}$, $R^{5'}$, and $R^{6'}$ are independent selected from hydrogen, alkyl (e.g., methyl), alkoxy (e.g., hydroxymethyl and 1-methyl-hydroxymethyl), aryl (e.g., phenyl), carboxyl, hydroxyl, carboxamido (e.g. H—C(O)—NH—), alkylcarboxamido (e.g., CH$_3$—CH$_2$—C(O)—NH—), alkenylcarboxamido (e.g., CH2=CH—C(O)—NH—), alkylamino-alkenyl-carboxamido (e.g., (CH$_3$)$_2$N—CH$_2$—CH=CH—C(O)—NH—), halo-alkenyl-carboxamido (e.g., Cl—CH$_2$—CH=CH—C(O)—NH—), hydroxyalkyl (e.g., HO—CH$_2$—), halo, carboxyalkyl (HO—C(O)—CH$_2$—), nitro, amino, alkylcarbonyl (e.g., acetyl or CH$_3$—C(O)—), haloalkyl-carbonyl (e.g., CF$_3$—C(O)—), sulfonylamino (e.g., S(O)(O)—NH—), alkyl-sulfonylamino (e.g., CH$_3$—S(O)(O)—NH—), haloalkyl-sulfonylamino (e.g., CF$_3$—S(O)(O)—NH—), cycloalkyl-sulfonylamino (e.g., cyclohexyl-S(O)(O)—NH— or cyclopropyl-S(O)(O)—NH—), pyridinyl-sulfonylamino (e.g., pyridin-3-yl-S(O)(O)—NH— or pyridin-3-yl-S(O)(O)—NH—), pyrazolinyl-sulfonylamino (e.g., pyrazolin-4-yl-S—(O)(O)—NH—), and N-alkylpyrazolinyl-sulfonylamino (e.g., N-methylpyrazolin-4-yl-S—(O)(O)—NH—).

Embodiment 4

The compound of any of the foregoing embodiments of a formula:

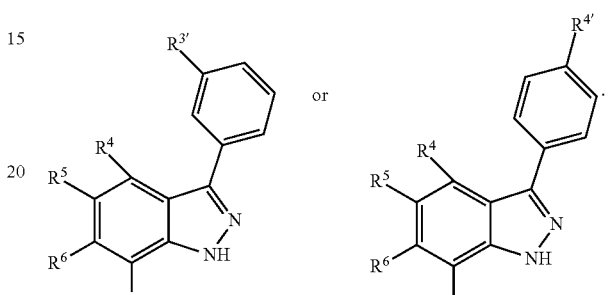

Embodiment 5

The compound of any of the foregoing embodiments of a formula:

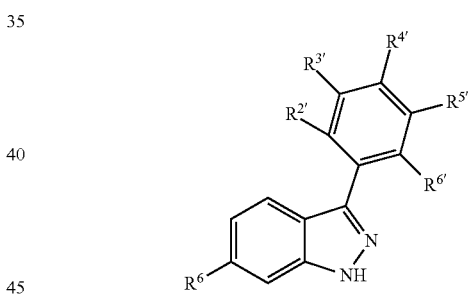

Embodiment 6

The compound of any of the foregoing embodiments of a formula:

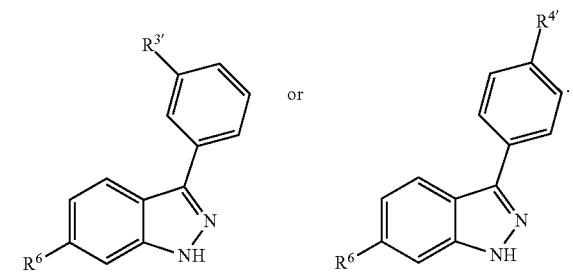

wherein optionally $R^6$ is halo (e.g., fluoro).

Embodiment 7

The compound of any of the foregoing embodiments, wherein $R^6$ is halo (optionally fluoro).

Embodiment 8

The compound of any of the foregoing embodiments, wherein $R^4$ is carboxyl.

Embodiment 9

The compound of any of the foregoing embodiments, wherein Aryl is 1,3-benzodioxol-5-yl.

Embodiment 10

The compound of any of the foregoing embodiments, wherein the compound is:

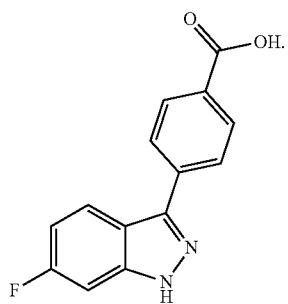 [SMILES: O=C(O)c1ccc(-c2n[nH]c3cc(F)ccc23)cc1]

Embodiment 11

The compound of any of the foregoing embodiments, wherein the compound is:

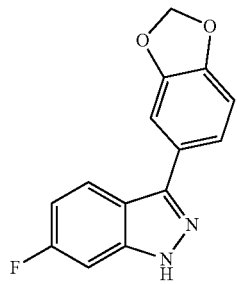 [SMILES: Fc1ccc2c(-c3ccc4c(c3)OCO4)n[nH]c2c1]

Embodiment 12

The compound of any of the foregoing embodiments of a formula selected from:

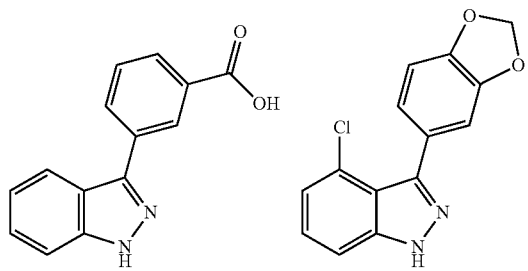

-continued

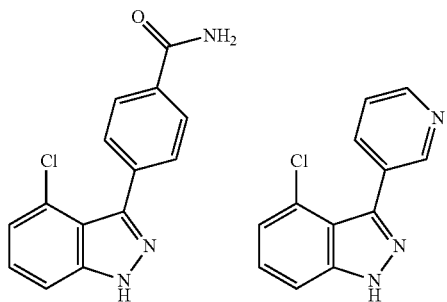

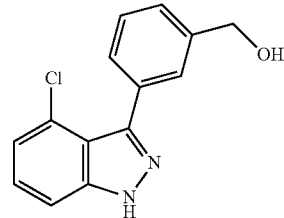

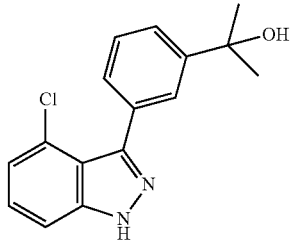

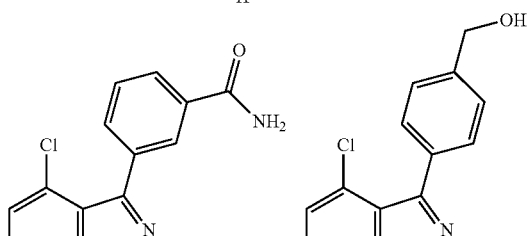

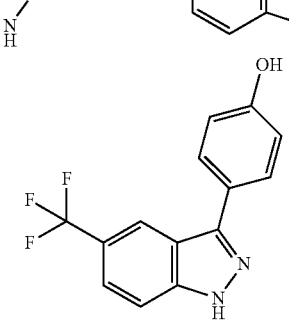

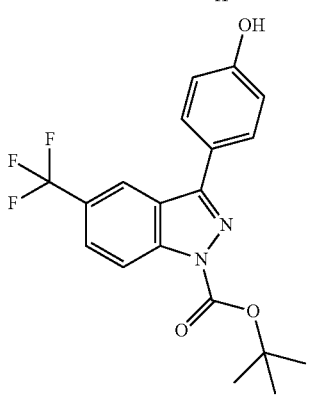

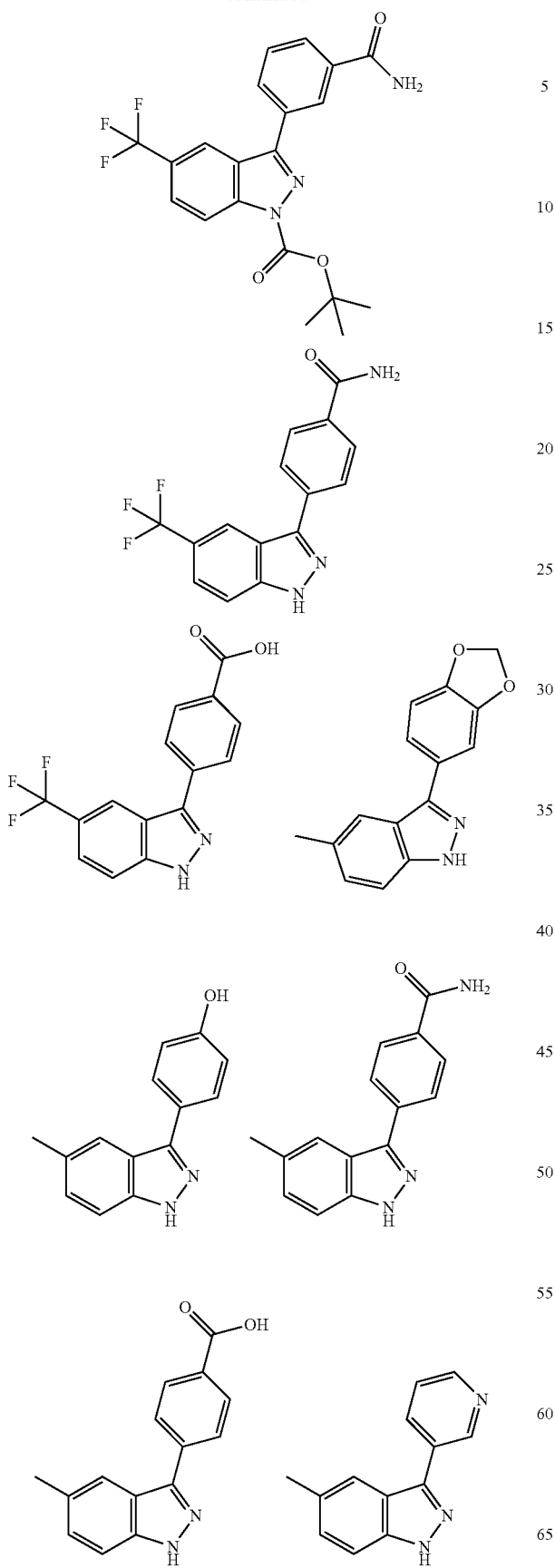
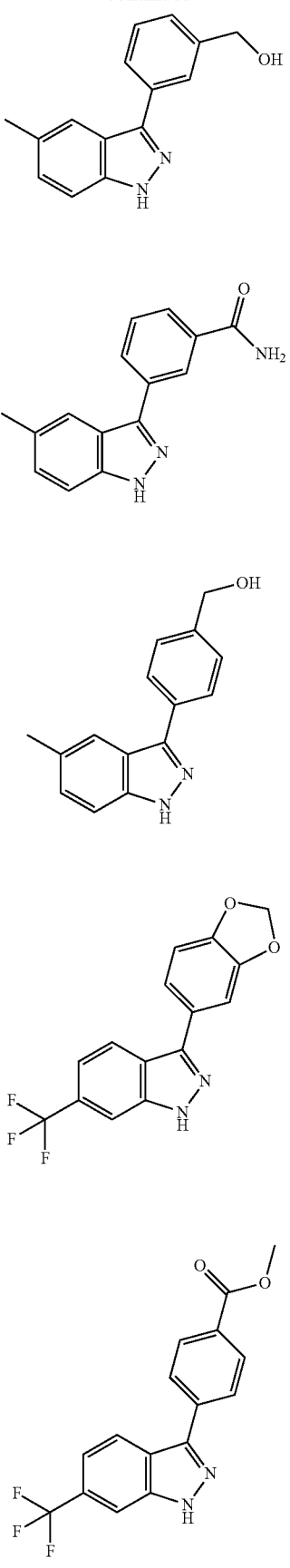

31
-continued
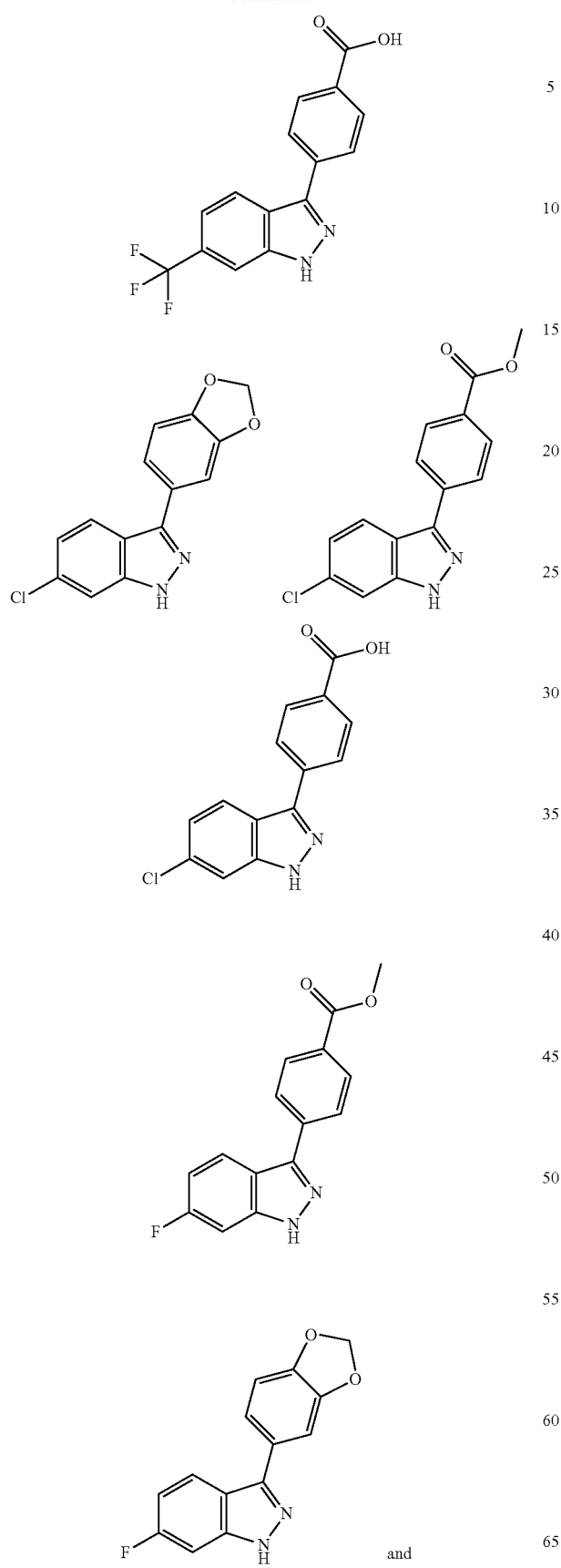
32
-continued
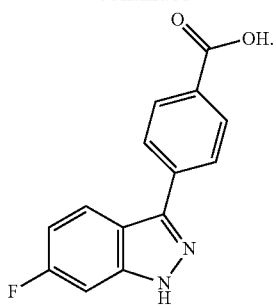
Embodiment 13
The compound of any of the foregoing embodiments of a formula selected from:
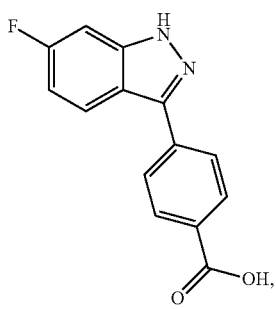
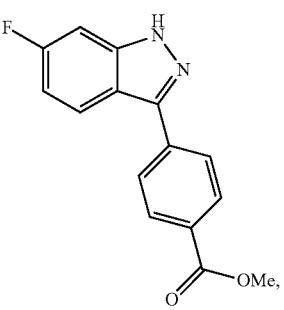
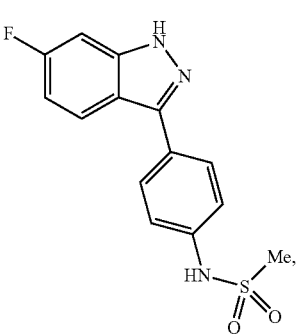

-continued

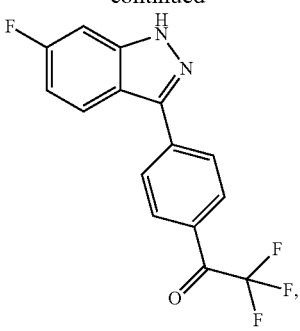

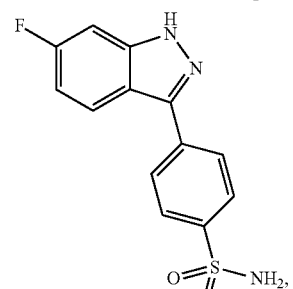

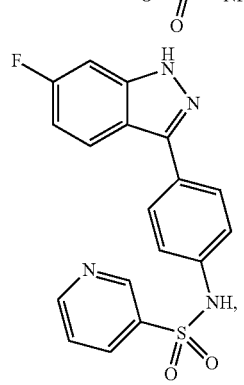

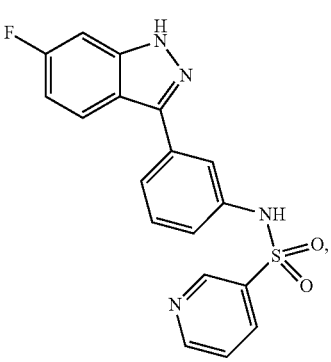

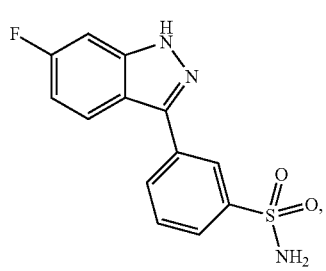

-continued

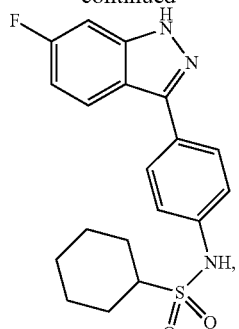

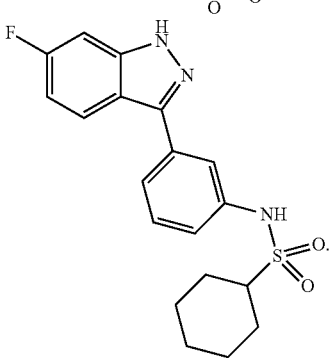

Embodiment 14

A pharmaceutical composition comprising any of the compounds of the foregoing embodiments and a pharmaceutical carrier, excipient, or diluent.

Embodiment 15

A pharmaceutical composition comprising the compound of embodiment 12 and a pharmaceutical carrier, excipient, or diluent.

Embodiment 16

A pharmaceutical composition comprising the compound of embodiment 13 and a pharmaceutical carrier, excipient, or diluent.

Embodiment 17

A pharmaceutical composition comprising any of the compounds disclosed in the specification for this application and a pharmaceutical carrier, excipient, or diluent.

Embodiment 18

A method for treating a disease or disorder associated with mitogen-activated protein kinase 4 (MEK4) activity in a subject in need thereof, the method comprising administering to the subject any of the compounds of embodiments 1-13 or any of the pharmaceutical compositions of embodiments 14-17.

Embodiment 19

The method of embodiment 18, wherein the disease or disorder is a cell proliferative disease or disorder.

Embodiment 20

The method of embodiment 19, wherein the cell proliferative disease or disorder is cancer.

Embodiment 21

The method of embodiment 20, wherein the cancer is prostate cancer.

Embodiment 22

The method of embodiment 20, wherein the cancer is breast cancer.

Embodiment 23

The method of embodiment 20, wherein the cancer is pancreatic cancer.

Embodiment 24

The method of embodiment 20, wherein the cancer is colon cancer.

EXAMPLES

The following Examples are illustrative and should not be interpreted to limit the scope of the claimed subject matter.

Example I

Reference is made to the manuscript Deibler et al., "Synthesis and Biological Evaluation of 3-Arylindazoles as Selective MEK4 Inhibitors", ChemMedChem. 2019 Mar. 22; 14(6):615-620, the content of which is incorporated herein by reference in its entirety.
Title—Synthesis and Biological Evaluation of 3-Arylindazoles as Selective MEK4 Inhibitors
Results
Recognizing that MEK4 represents a novel and validated therapeutic target we sought to identify and characterize selective MEK4 inhibitors. Previously, we developed a platform for mapping the pharmacological relatedness of all seven MEK kinase family members to understand compound selectivity.[11] Herein we discuss leveraging that foundational platform to screen compounds and identify a potent and selective hit molecule. Optimization and biological evaluation gave further insight into potential utilization of this series of compounds as selective MEK4 inhibitors.

Figure 2:
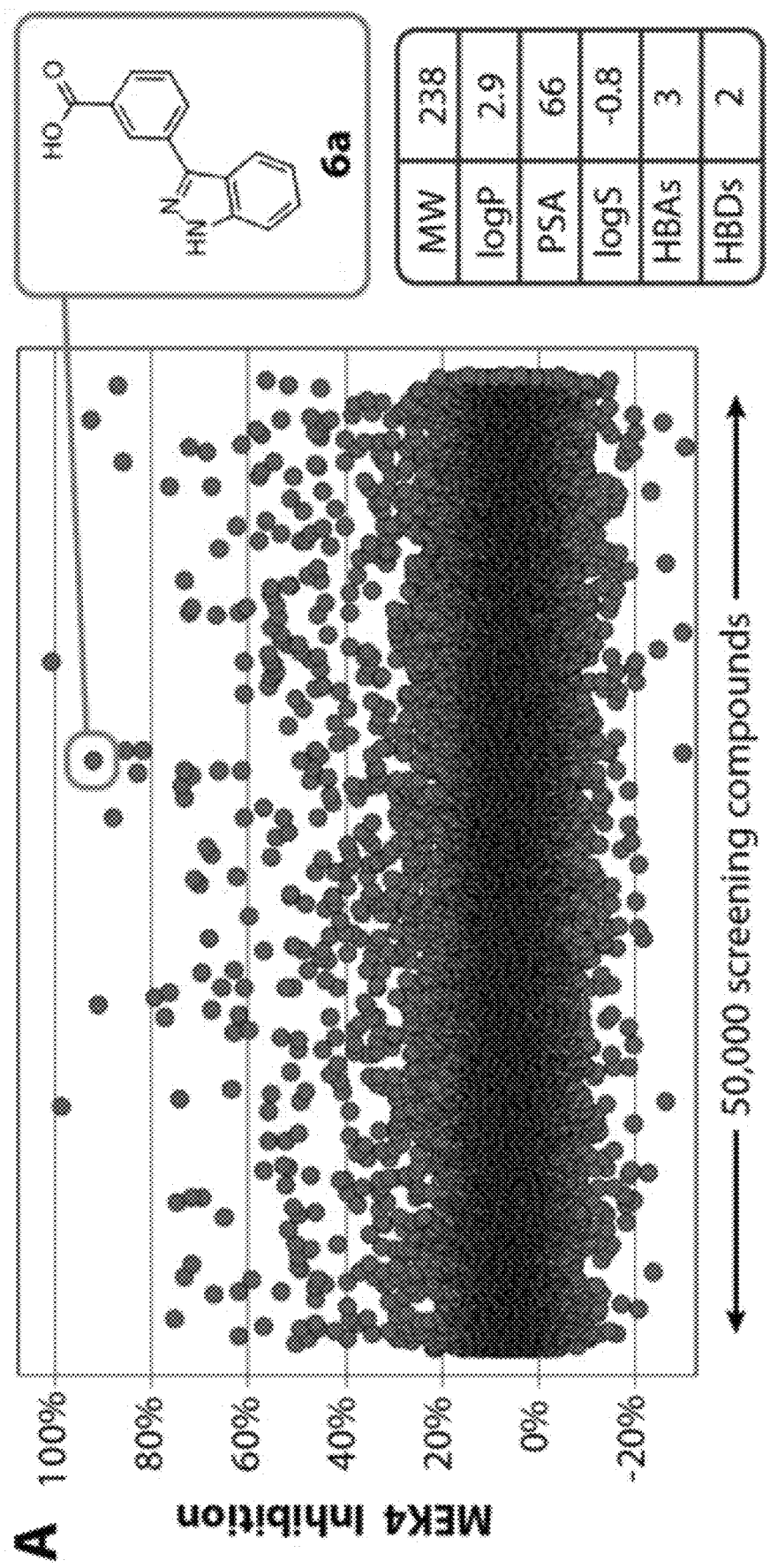
FIG. 2. Identification and validation of 6a. (A) High throughput chemical screen using a functional ADP-Glo assay revealed 6a as one of the most active hit compounds against MEK4b. (B) 6a was tested with and without detergent in the ADP-Glo assay at three doses (n=2-4). (C) TR-FRET was used to evaluate competitive binding with an active site tracer to MEK4 (n=6). (D) 6a was tested at four different ATP concentrations and potency was determined using a logistic regression curve fit (n=2). (E) Thermal stability of various MEK4 constructs was analyzed with vehicle (grey curves) or 6a (blue curves) using a Boltzmann curve fit. Data is representative of two independent runs. (F) 6a was titrated against the seven MEK family proteins to calculate the potency in each system by logistic regression (n=2).
Figure 2:
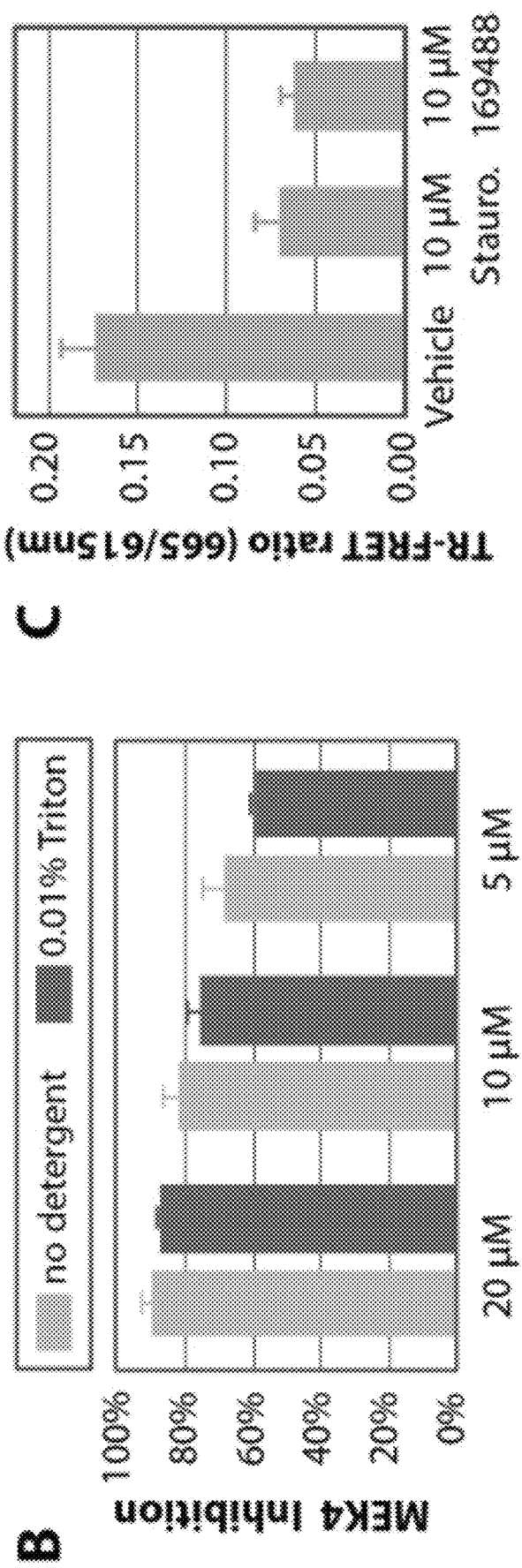
Figure 2:
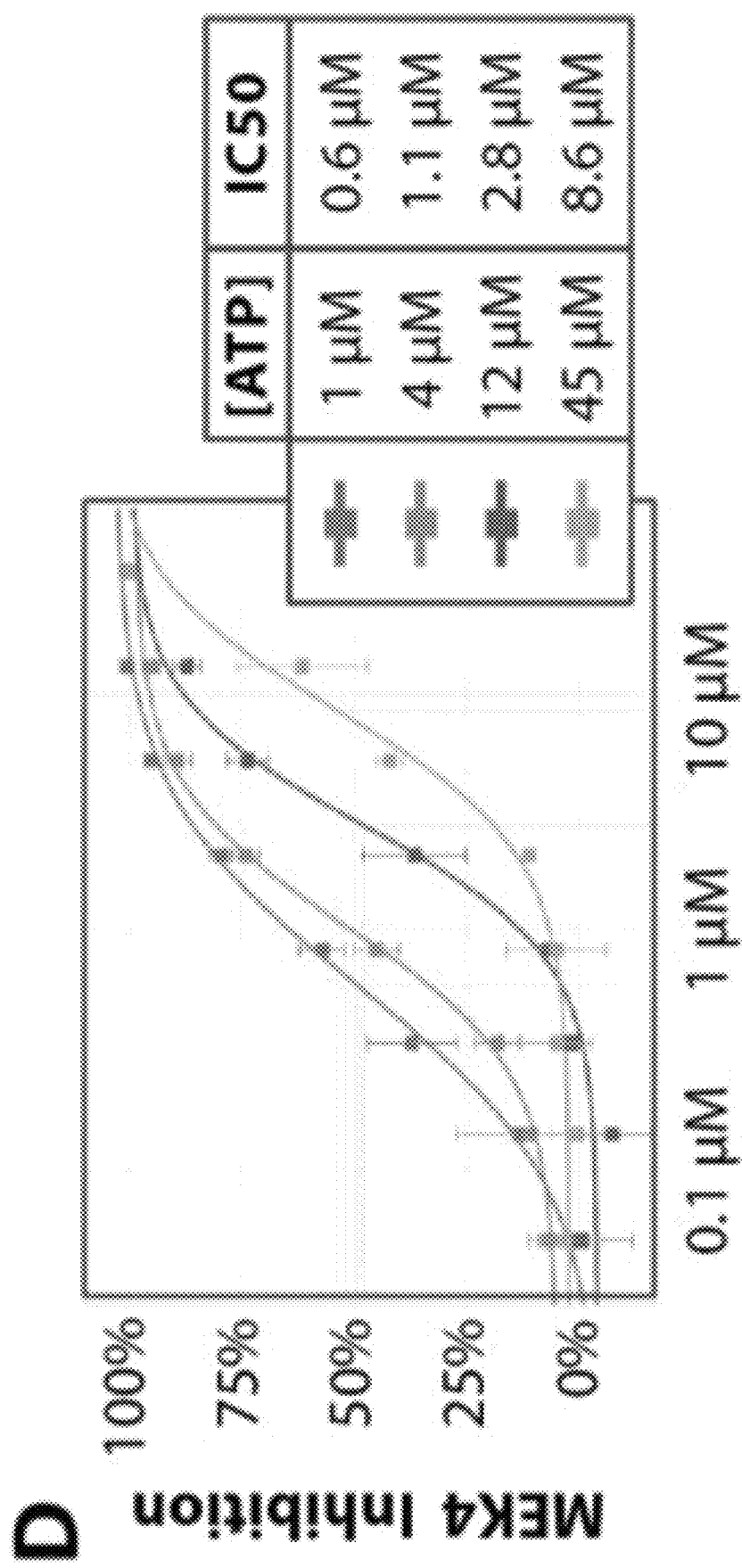
Figure 2:
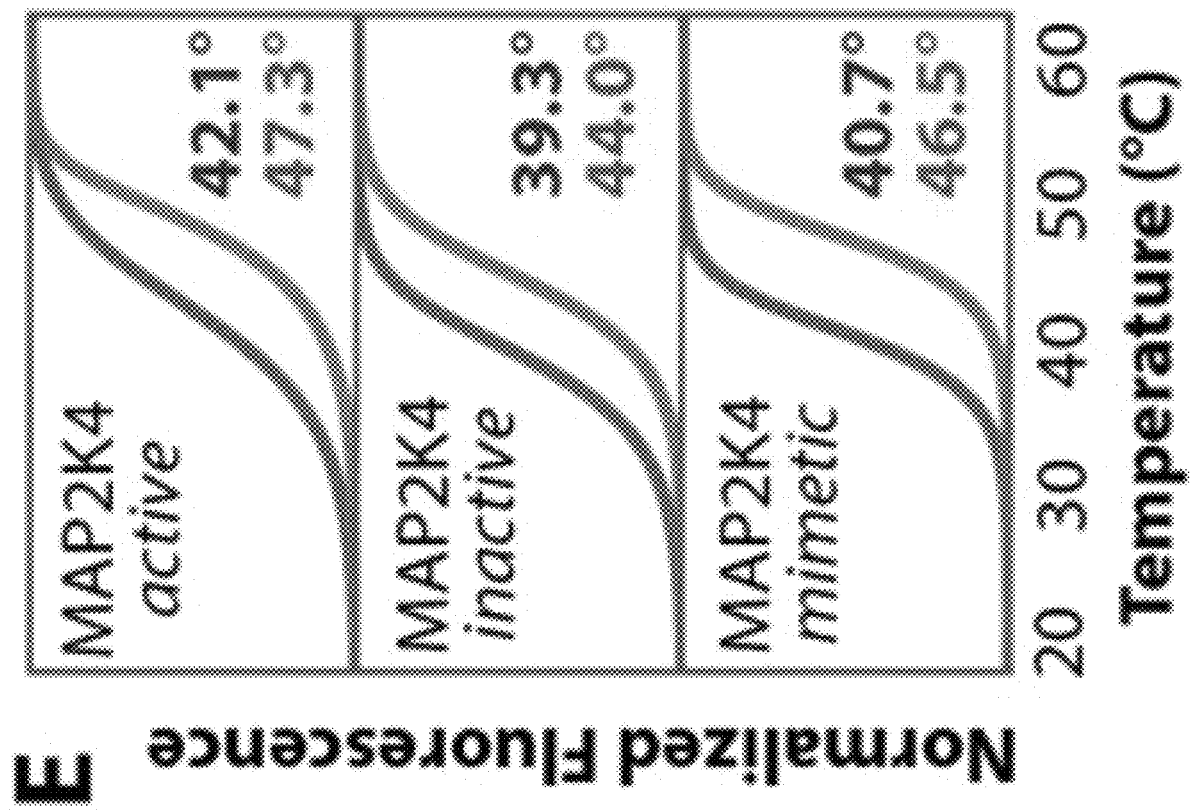
Figure 2:
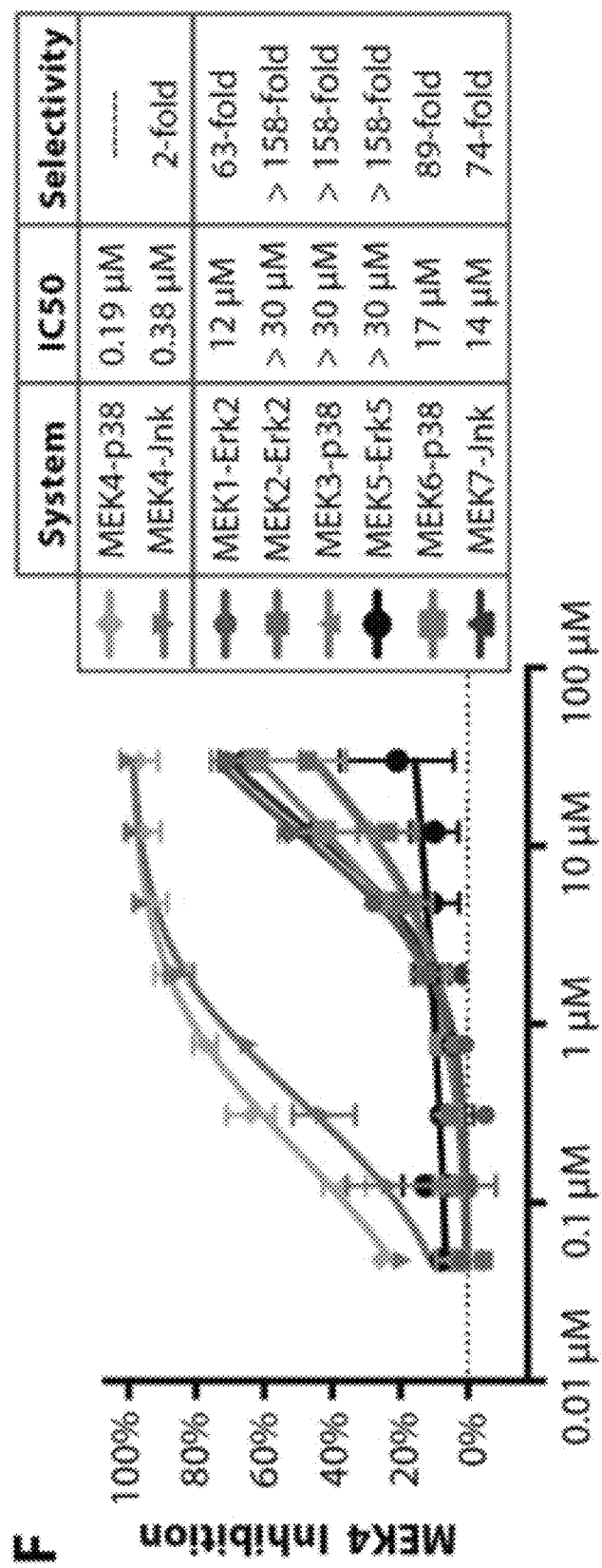

To discover new inhibitors of MEK4, a library of 50,000 diverse compounds (commercially available ChemBridge DIVERSet-CL) was screened using an enzymatic ADP-Glo assay with active recombinant human MEK4 and full-length p38α substrate. The library was calculated to have a diversity index of 0.73 and determined that >90% of the compounds adhered to drug-like filters including Lipinski, Veber, and Pipeline Pilot SMARTS filters. Several compounds exhibited potent activity, and for this study subsequent work focused on a relatively small hit compound with an indazole core that inhibited MEK4 by 92% at 10 μM in the initial screen (FIG. 2A, 6a). LC/MS analysis of the compound confirmed its mass and that its purity was >95% (data not shown).

Compound 6a was next tested to determine if its activity could be attributed to compound aggregation. A large fraction of hit compounds in wide-ranging HTS campaigns have been found to inhibit the target protein by forming hydrophobic aggregates that nonspecifically interact with the protein.[12] Since detergents have been shown to disrupt compound aggregation, a common way to identify these artifacts is by adding detergent to the assay and looking for a substantial or complete loss of potency. Inhibitor 6a was tested at several concentrations in the ADP-Glo assay using a buffer with and without 0.01% Triton X-100, and similar MEK4 inhibition profiles were observed in both cases (FIG. 2B). Additionally, 6a was examined by dynamic light scattering (DLS), another common way to identify compound aggregates. The compound was tested at 20, 5, and 1 μM in buffer with and without Triton X-100, and under no conditions were aggregates observed (data not shown).

To ensure 6a does not nonspecifically interfere with the ADP-Glo assay technology (for example, as a luciferase inhibitor) 1 μM ADP was spiked in to simulate enzymatic ATP turnover and no reduction in the luminescent signal at 20, 10, and 5 μM of compound was observed (data not shown). To further validate 6a as a bona fide MEK4 inhibitor, an orthogonal TR-FRET assay was used to determine if the compound could displace a fluorescently-staurosporine, a low nanomolar MEK4 and pan-kinase tool inhibitor (FIG. 2C).

The ability of 6a to displace the active site TR-FRET probe, along with the potential for kinase hinge binding by the indazole moiety, suggested that the compound likely binds to the ATP pocket of the MEK4 active site. To further characterize the binding mode, an ATP titration experiment was performed. Direct ATP-competitive inhibitors generally experience a loss of potency when tested in the presence of high ATP concentrations, particularly at concentrations above the enzyme's $K_M$ for ATP.[13]

We determined the $K_M$ of MEK4 for ATP to be 3.0±0.4 μM, so 6a was tested at eight doses each with 1, 4, 12, and 45 μM of ATP. The potency of the inhibitor decreased with each stepwise increase in ATP concentration, suggesting an ATP-competitive binding mode (FIG. 2D). As expected, a smaller shift was observed from 1 to 4 μM since 4 μM approximates the $K_M$ value.

Next, the fluorescence thermal shift (FTS) assay was used to determine the change in thermal stability of MEK4 in the presence of 6a. The stability of a protein is commonly altered when it binds a ligand, and we previously demonstrated that a hallmark of MEK4 inhibitors is increased thermal stability.[14] Compound 6a increased the melting temperature of three MEK4 constructs: (1) phosphorylated (active) full-length MEK4 (the same construct used in the ADP-Glo and TR-FRET assays described above), (2) the nonphosphorylated (inactive) kinase domain of MEK4, and (3) a mutant (S257E/T261E) phosphomimetic (partially active) version of the kinase domain, each by 5-6 degrees (FIG. 2E). This suggests 6a has little preference for binding the active versus inactive forms of MEK4.

Finally, to investigate if 6a exhibits specificity for MEK4 relative to the other six MEK isoforms (which have 38-61% homology to MEK4), an ADP-Glo MEK assay panel[11] M was used to determine the potency of this inhibitor against all seven MEK enzymes. The assays were run at a saturating concentration of full-length protein substrates (Erk2, Erk5, p38α, or Jnk1β), and an ATP concentration below the $K_M$ of ATP for each enzyme. The potency of 6a against MEK4 was 0.19 μM and 0.38 μM using p38α and Jnk1β substrates, respectively. In comparison, the next most potent target was MEK1, with an $IC_{50}$ of 12 μM, indicating that 6a has 30- to 60-fold selectivity for MEK4 relative to any other MEK protein (FIG. 2F).

Figure 3:
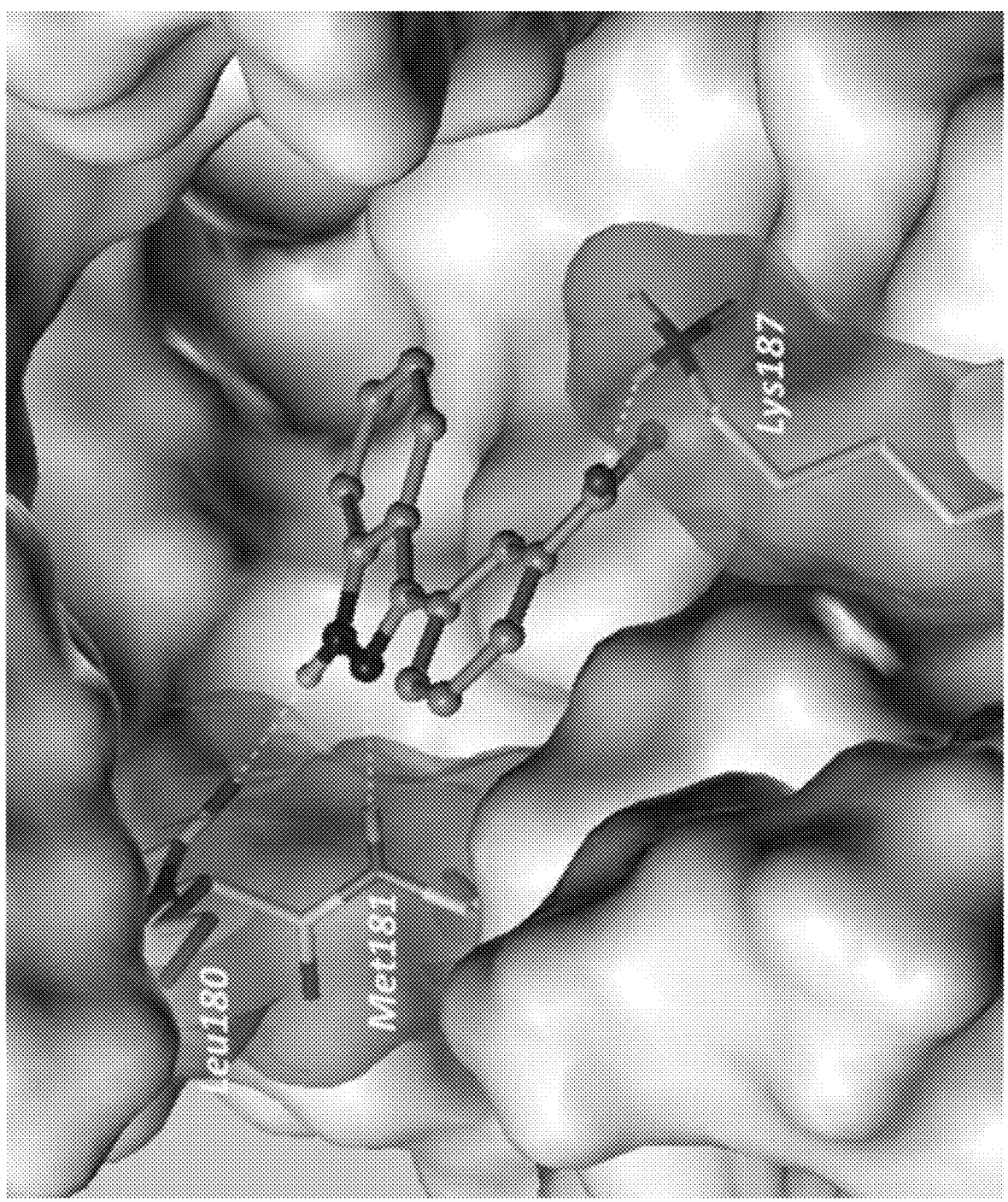
FIG. 3. Modelling of 6a. Docked pose of 6a with MAP2K4. Key interactions are highlighted, including those with hinge residues Leu180 and Met181, as well as an electrostatic interaction between the carboxylate and Lys187.

The identification and validation of 6a as a novel ATP-competitive MEK4 inhibitor prompted us to model its binding to MEK4 and subsequently carry out medicinal chemistry in an effort to further improve its potency and selectivity. Molecular modeling of compound 6a bound to MEK4 was carried out using the Glide docking engine implemented in the Schrödinger suite.[15] Several key interactions were identified from the molecular modeling. When analyzing the predicted binding poses of 6a, critical hydrogen bonding interactions in the hinge region between the small molecule and the backbone of MEK4 residues Leu180 and Met181 were observed (FIG. 3). The predicted binding poses are consistent with it being an ATP-competitive inhibitor (FIG. 2D). Modeling also indicated a favorable electrostatic interaction between the 6a carboxylate and Lys187. In addition, there appeared to be space extending from the 5- and 6-position of the indazole ring that was unoccupied. Replacement of the carboxylate with other hydrogen bond acceptors could maintain or strengthen this interaction while modulating the physiochemical properties of the inhibitors.

Synthesis of the new indazole analogs proceeded as shown in Table 1 starting with commercially available indazoles 1. Selective iodination at the 3-position was achieved using NaOH and iodine to provide the intermediate in yields ranging from 90-95% yield. The iodinated heterocycle was then treated with $Boc_2O$ to protect the free N—H group, since it was found that unprotected indazoles either failed in the subsequent Suzuki reaction or had dramatically slower reaction rates. Thus, treatment of iodides 2 with a range of boronic acids (3) provided the final 3-aryl indazoles 4 in moderate to good yields. In several cases, the Boc-protecting group was lost during the course of the Suzuki reaction. In others, deprotection was carried out separately using TFA. For final compounds containing carboxylic acids, their methyl ester boronic acid was used in the Suzuki reaction and subsequent hydrolysis was then performed to generate the carboxylic acid.

TABLE 1

Synthesis and SAR of substituted 3-aryl indazoles.

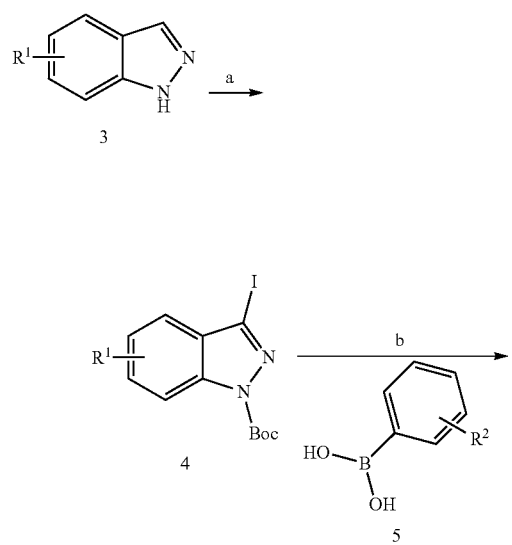

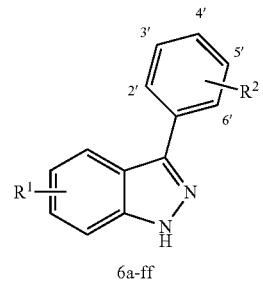

6a-ff

| Compound | $R^1$ | $R^2$ | MEK4-p38, $IC_{50}$, μM [95% CI] |
|---|---|---|---|
| 6a | H | 3'-$CO_2H$ | 0.64 [0.53, 0.77] |
| 6b[a] | 4-$CH_3$ | 4'-OH | 4.0 [3.3, 4.8] |
| 6c | 4-Cl | 3',4'-($OCH_2O$) | 4.5 [3.9, 5.2] |
| 6d | 4-Cl | 4'-$CONH_2$ | 4.4 [3.9, 5.0] |
| 6e | 4-Cl | 3'-pyridyl | >22 |
| 6f | 4-Cl | 3'-$CH_2OH$ | 7.2 [6.0, 8.6] |
| 6g | 4-Cl | 3'-$C(CH_3)OH$ | >22 |
| 6h | 4-Cl | 3'-$CONH_2$ | 1.3 [1.0, 1.6] |
| 6i | 4-Cl | 4'-$CH_2OH$ | 8.1 [7.2, 9.1] |
| 6j | 5-$CF_3$ | 4'-OH | 0.76 [0.67, 0.86] |
| 6k[c] | 5-$CF_3$ | 4'-OH | >20 |
| 6l[c] | 5-$CF_3$ | 3'-$CONH_2$ | 9.9 [7.3, 14] |
| 6m | 5-$CF_3$ | 4'-$CONH_2$ | 1.1 [0.99, 1.3] |
| 6n | 5-$CF_3$ | 4'-$CO_2H$ | 0.47 [0.39, 0.55] |
| 6o[b] | 5-$CH_3$ | 3'-$CH_2OH$, 4'-F | 1.0 [0.69, 1.5] |
| 6p | 5-$CH_3$ | 3',4'-($OCH_2O$) | 0.41 [0.36, 0.48] |
| 6q | 5-$CH_3$ | 4'-OH | 0.59 [0.46, 0.75] |
| 6r | 5-$CH_3$ | 4'-$CONH_2$ | 0.56 [0.40, 0.77] |
| 6s | 5-$CH_3$ | 4'-$CO_2H$ | 0.15 [0.10, 0.23] |
| 6t | 5-$CH_3$ | 3'-pyridyl | 1.6 [1.1, 2.3] |
| 6u | 5-$CH_3$ | 3'-$CH_2OH$ | 1.4 [1.2, 1.8] |
| 6v | 5-$CH_3$ | 3'-$CONH_2$ | 0.97 [0.74, 1.3] |
| 6w | 5-$CH_3$ | 4'-$CH_2OH$ | 1.3 [1.1, 1.5] |
| 6x | 6-$CF_3$ | 3',4'-($OCH_2O$) | 6.1 [4.9, 7.7] |
| 6y | 6-$CF_3$ | 4'-$CO_2CH_3$ | >20 |
| 6z | 6-$CF_3$ | 4'-$CO_2H$ | 0.72 [0.56, 0.92] |
| 6aa | 6-Cl | 3',4'-($OCH_2O$) | 0.46 [0.30, 0.71] |
| 6bb | 6-Cl | 4'-$CO_2CH_3$ | 2.2 [1.7, 2.9] |
| 6cc | 6-Cl | 4'-$CO_2H$ | 0.12 [0.10, 0.14] |
| 6dd | 6-F | 4'-$CO_2CH_3$ | 0.42 [0.35, 0.51] |
| 6ee | 6-F | 3',4'-($OCH_2O$) | 0.063 [0.029, 0.14] |
| 6ff | 6-F | 4'-$CO_2H$ | 0.041 [0.034, 0.049] |

[a] Reagents and Conditions: (a) i. NaOH, $I_2$, MeOH, rt, 24 h, 90-95%; ii. $Boc_2O$, rt, 16 h.; (b) Ar—$B(OH)_2$, $PdCl_2(dppf)$·DCM, $K_3PO_4$, $H_2O$, 1,4-Dioxane, 90° C., 1.5 h., 50-70%.
[b] Compounds were purchased from ChemBridge.
[c] Compound has a Boc-group on the indazole N-1 position.

Figure 4:
FIG. 4. Docked pose of 6ff in MEK4.

Based on molecular modeling of unsubstituted indazole 6a, it was expected that introduction of small hydrophobic groups on the indazole ring could occupy a back hydrophobic pocket. Addition of methyl- or chloro-groups at the indazole 4-position resulted in compounds with significantly decreased potency (Table 1). In contrast to unfavorable substitutions on the 4-position, addition of several different small hydrophobic groups on the 5-position resulted in compounds with greater MEK4 potency. Addition of a 5-$CF_3$ group onto the indazole in combination with 4'-$CO_2H$ (6n) or 4'-OH (6j) resulted in inhibitors with comparable potency to the original unsubstituted hit compound (6a). The inhibitor with a $CH_3$ on the 5-position and a 4'-OH on the 3-aryl ring (6q) was almost 7-times more potent than the analogous 4-$CH_3$-substituted indazole compound (6b). Compounds with a 5-$CH_3$ on the indazole tended to be more potent when the 3-aryl ring was substituted at the 4'-position. Compounds with a Boc-group on the indazole N-1 were completely inactive, which is consistent with the modeling which shows the indazole N—H forming a key interaction with the kinase hinge region. While exploring the activity of 6-$CF_3$ analogs, the importance of the 3-aryl carboxylic acid moiety was also examined. Inhibitors with a methyl ester instead of an acid (e.g. 6y) were completely inactive, while their carboxylic acid analog (6z) showed potent inhibition ($IC_{50}$ of 0.72 μM). It was found that chloro-substituted indazoles possessed improved potency compared with their —$CH_3$ or —$CF_3$ analogs. Finally, several indazoles with a fluorine on the indazole 6-position were prepared and showed excellent potency for MEK4 (6ee and 6ff) and were 5- and 10-fold more potent (respectively) than their 6-Cl analogs. Based on further molecular docking studies (FIG. 4) it is suspected that the fluorine stabilizes most favourable planar confirmation of the compound while being the optimal size for the small polar/solvent expose region.

Having improved the MEK4 potency of our lead series, several of the most potent inhibitors were profiled against the entire MEK family to evaluate selectivity (Table 2). It was found that all compounds tested inhibited MEK4 more potently than any other MEK kinase. In general, compounds had the greatest selectivity against MEK5, 2, and 3. In particular, compound 6ff displays excellent selectivity across the entire MEK family. This compound is at least 150-fold more potent against MEK4 than any other MEK-kinase, and is at least 385-fold selective against three other MEK kinases.

TABLE 2

MEK family profiling. All data are $IC_{50}$ values in μM.

| | MEK isoform | | | | | | | |
|---|---|---|---|---|---|---|---|---|
| ID | MEK 4 (p38) | MEK 4 (Jnk) | 1 | 2 | 3 | 5 | 6 | 7 |
| 6a | 0.18 | 0.46 | 7.2 | >27 | 16 | >27 | 10 | 8.3 |
| 6b | 0.92 | 0.88 | 11 | 15 | >27 | >27 | 21 | 12 |
| 6j | 0.25 | 0.24 | 4.6 | 5.3 | 2.3 | >27 | 1.6 | 2.2 |
| 6n | 0.13 | 0.06 | 10 | >27 | 2.9 | >27 | 6.0 | 2.0 |
| 6o | 0.39 | 0.75 | 4.0 | 5.4 | 6.0 | >27 | 3.4 | 4.9 |
| 6p | 0.11 | 0.56 | 6.6 | 9.1 | 8.5 | 16 | 3.2 | 6.1 |
| 6q | 0.21 | 0.41 | 7.7 | 7.2 | 5.5 | 25 | 2.2 | 5.4 |
| 6r | 0.20 | 0.51 | 3.9 | 6.1 | 4.1 | 19 | 2.1 | 3.7 |
| 6s | 0.18 | 0.22 | 17 | >27 | 12 | >27 | 8.7 | 11 |
| 6z | 0.36 | 0.10 | 17 | >27 | >27 | 0.35 | 8.8 | 6.9 |
| 6ee | 0.26 | 1.5 | 6.6 | 9.3 | 21 | >27 | 5.8 | 14 |
| 6ff | 0.066 | 0.10 | 15 | >27 | >27 | >27 | 11 | 12 |

[a] Sample size n = 2 and 95% confidence intervals were calculated for each compound tested.

Because compound 6ff was a potent and selective (among the MEK family) MEK4 inhibitor in the functional assay, it was evaluated against 57 diverse kinases (see supporting information Table 3). These kinases were chosen to be a highly representative set of the broader kinome in accordance with recent work showing this approach provides an efficient way in which to assess overall kinase selectivity while minimizing experimentation.[16] In addition to the 50 kinases from the diversity panel,[16] the 7 MEK family members were also included. The original hit (6a) was also evaluated to allow comparison. Inhibitor 6a was found to have an S(35) value of 0.088, meaning that it inhibited 8.8% of tested kinases>35%, which in our case was 5 out of 57 kinases tested. Inhibitor 6ff had an S(35) of 0.21, or 12 out of the 57 kinases. Both compounds were tested at 10 μM and both fully inhibited MEK4. Because both compounds fully inhibited MEK4 at the tested concentration of 10 μM and 6ff is 3-4 fold more potent than 6a, it is possible that 6ff may be more selective than compound 6a when both compounds are tested at concentrations that give equivalent MEK4 inhibition. Additional work to further define and improve the kinase selectivity of our lead series is underway.

Figure 5:
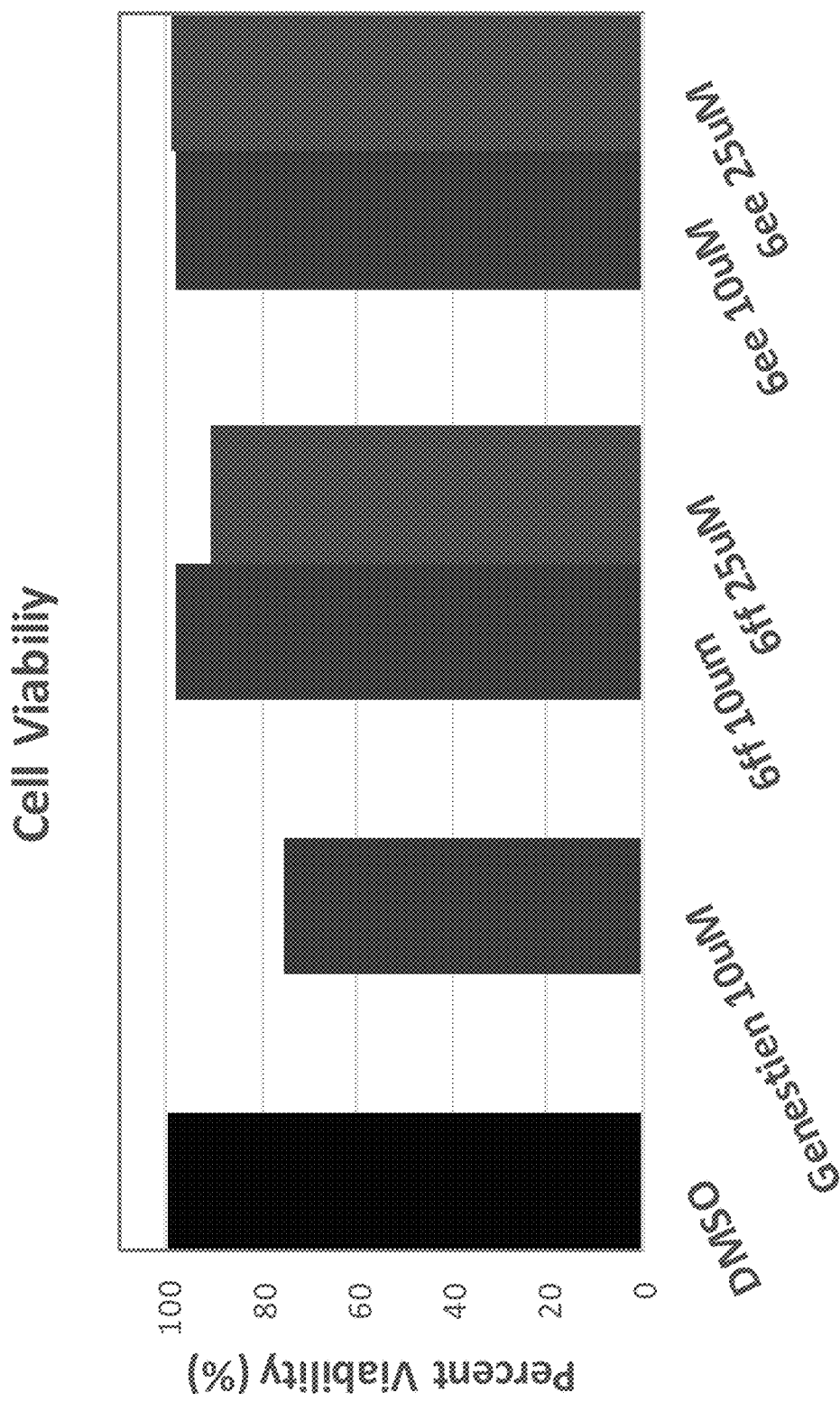
FIG. 5. Cell viability data for NUCC-201177 (6ff) and NUCC-201167 (6ee).

A preliminary evaluation of the cellular efficacy of 6ff was performed to investigate the potential involvement of MEK4 in cancer cell motility and migration. The results from a wound scratch assay showed that compound 6ff had no efficacy at the concentrations tested (10 and 25 μM).[10b] Interestingly, compound 6ee has modest efficacy at 10 μM and performs better at 25 μM, though never achieving the effect of control compound genistein (see Table 4), suggesting differences in cell permeability between the negatively-charged 6ff carboxylate and the 6ee ether may be relevant. A trypan blue exclusion for cells treated for 3 days to look at effects on proliferation and viability was also performed (see FIG. 5). Interestingly, it was observed that both compounds (6ff and 6ee) had less toxicity was performed at 10 μM). The results could be indicative of the necessity to improve compound solubility and cell permeability.

In summary, we have evaluated and optimized the potency of a series of indazoles selective for MEK4 in vitro. To the best of our knowledge this is the first potent and selective (among the MEK family) inhibitor of MEK4. Analysis of the subtle differences of ligand binding in conjunction with the previous known trends of MEK family selectively that we have described allowed for the discovery of a potent and selective MEK4 inhibitor. The empirical binding affinities and functional potencies, along with sequential in silico docking studies, were used to predict the molecular features of the ligands responsible for activity and selectivity across this kinase family. The structure-activity relationship described herein indicates that the hit compounds are amenable to further optimization as they progress into more advanced in vivo and preclinical studies. The optimized compound 6ff has strong potency and moderate selectivity which will be improved in the future. Further evaluation of the lead inhibitors is underway to validate and pursue MEK4 as a relevant cancer target.

Experimental Section

Molecular Modeling of Indazole-based MEK4 inhibitor. To carry out the docking, the ATP bound MEK4 crystal structure (pdb code 3ALN) was used. Analysis of this crystal structure revealed that it has missing or uncertain (high B values) atoms on the side chains of the active site residues and some of the residues show restricted torsions. To build a MEK4 model suitable for docking, protein refinement using the Prime module implemented in Schrödinger platform was applied. Using this module, the missing atoms were added and torsional constrains were relieved from the Lys321, Leu236, and Lue180 residues present in the ATP binding site. After these corrections, the structure was subjected to an energy minimization in OPLS3 force field. Finally, the MEK4 structure was subjected to the Protein Preparation panel implemented in Schrödinger suite to ensure the structure is suitable for in-silico studies. The protein preparation panel added missing hydrogen atoms and oriented them suitably for hydrogen-bonding, B-values were replaced with force field charges, oriented amide bonds in appropriate configurations, added missing atoms, relieved side-chain bumping, set the protonation state to pH=7.4, and eliminated torsional restrictions. The MEK4 inhibitor was prepared for docking using the Lig-Prep module by fixing the pH=7.41. After preparing the protein and the ligand, the Glide Extra Precision docking engine of Schrödinger was used to dock the ligand.

MEK4 ADP-Glo kinase activity assay. Kinase activity of recombinant active full-length human MEK4 (Carna Biosciences) was measured using the ADP-Glo assay (Promega) with 3 µM recombinant full-length human p38α (MAPK14). The concentration of ATP used for high throughput screening was 3 µM (equal to the ATP $K_M$ value for MEK4). For ATP competition studies, the ATP concentration was varied (1, 4, 12, or 45 µM). Standard ADP-Glo assay buffer contained 25 mM Tris-HCl, 5 mM beta-glycerophosphate, 2 mM dithiothreitol (DTT), 0.1 mM $Na_3VO_4$, and 10 mM $MgCl_2$ at pH 7.5. Triton X-100 was added at a final concentration of 0.01% (w/v) for the aggregation studies. For MEK family profiling, recombinant active full-length human MEK1, 2, 3, 4, 5, 6, and 7 (Carna Biosciences) were used together with 3 µM recombinant full-length substrates. p38α was used for MEK3, 4, and 6. Jnk1B (MAPK8) was used for MEK4 and 7. Erk2 (MAPK1) was used for MEK1 and 2. Erk5 (MAPK7) was used for MEK5. All reactions included 0.6 µM ATP, a concentration that was at least 2-fold below the empirically determined ATP $K_M$ values for all MEKs.

MEK4 TR-FRET Lanthascreen binding assay. The ability of an inhibitor to compete with a fluorescent kinase active site tracer was measured using time-resolved FRET. 8 nM GST-tagged recombinant active full-length human MEK4 (Carna Biosciences) was mixed with 4 nM anti-GST IgG Europium W-1024 chelate (Columbia Biosciences). Staurosporine (LC Labs) or 6a were added to the mixture for 30 minutes followed by 20 nM fluorescent Tracer 236 (Thermo Fisher Scientific) for 30 minutes before detection. The TR-FRET assay buffer was composed of 25 mM Tris-HCl, 5 mM beta-glycerophosphate, 2 mM dithiothreitol (DTT), 0.1 mM $Na_3VO_4$, 10 mM MgCl2, and 0.008% Brij-35 at pH 7.5.

Fluorescence thermal shift assay. The thermal stability of different MEK4 constructs were quantified using SYPRO Orange dye (Thermo Fisher Scientific) to detect denatured protein in solution. Measurements were performed on a real-time PCR thermocycler (Bio-Rad CFX384) in 384-well clear PCR plates. 1 µg of MEK4 was added to each well in 10 µl of assay buffer (100 mM HEPES and 150 mM NaCl at pH 7.5) containing SYPRO Orange at 5× the vendor's final recommended concentration. The following MEK4 constructs were tested: (1) the same recombinant active full-length human MEK4 that was used for high throughput screening (Cama Biosciences); (2) the nonphosphorylated (inactive) kinase domain from MEK4; and (3) a S257E/T261E mutant phosphomimetic (partially active) version of the MEK4 kinase domain. The last two constructs contained residues 80-399 of MEK4 with a C-terminal 6×His tag for purification following expression in bacteria. To assess thermal stability, the temperature was increased 0.6° C. per minute from 10-90° C. and the raw fluorescence values from the instrument were fitted using a Boltzmann distribution model. Curves were normalized, plotted, and melting temperatures (Tm) were determined as the midpoint of each curve.

Kinase Selectivity Profiling. The binding affinities of NUCC-169488 and NUCC-201177 were tested at 10 µM in a high-throughput binding assay (KINOMEscan, Discoverx, CA, USA) against a panel of 57 kinases tagged with DNA. Compounds that bind the kinase active site and directly or indirectly prevent kinase binding to an immobilized ligand will reduce the amount of kinase captured on solid support. Conversely, test molecules that do not bind the kinase have no effect on the amount of kinase captured on the solid support. Hits were identified by measuring the amount of kinase captured in test versus control samples by using a quantitative PCR method that detects the associated DNA label (www.discoverx.com/tools-resources/publications-references). Results are presented in Table 3 as percent of control (POC). Selectivity score (S-score) is a quantitative measure of compound selectivity. S(35) is calculated as number of non-mutant kinases with POC<35/number of non-mutant kinases tested.

TABLE 3

KinomeScan binding assay against 57 kinases for compound 6a and 6ff.

| Target Gene Symbol | 6a (NUCC-169488) % Ctrl @ 10000 nM | 6ff (NUCC-201177) % Ctrl @ 10000 nM |
|---|---|---|
| AAK1 | 87 | 55 |
| ABL1(T3151)-non-phosphorylated | 67 | 15 |
| ABL1(T3151)-phosphorylated | 40 | 12 |
| ABL1-phophorylated | 86 | 73 |
| ABL2 | 100 | 100 |
| ALK(L1196M) | 59 | 61 |
| CAMK4 | 100 | 100 |
| CDC2L1 | 100 | 100 |
| CDK2 | 97 | 100 |
| CDK9 | 95 | 98 |
| CHEK2 | 76 | 39 |
| C;L3 | 94 | 100 |
| CSNK1A1L | 87 | 93 |
| CSML1E | 88 | 100 |
| CSNK1G1 | 80 | 90 |
| CSML2A1 | 0.75 | 0 |
| DMPK | 100 | 100 |
| EGFR(L747-S752DEL, P753S) | 85 | 81 |
| EPHA2 | 92 | 100 |
| EPHA6 | 97 | 99 |
| EPHB4 | 89 | 100 |
| ERK2 | 96 | 100 |
| FGFR1 | 100 | 99 |
| HIPK1 | 43 | 48 |
| ICK | 43 | 26 |
| IKK-ALPHA | 50 | 14 |
| IKK-EPSILON | 48 | 43 |
| KIT(L576P) | 59 | 11 |
| MAP3K4 | 90 | 100 |
| MARK4 | 97 | 86 |
| MEK1 | 62 | 49 |
| MEK2 | 60 | 61 |
| MEK3 | 13 | 1.6 |
| MEK4 | 0 | 0 |
| MEK5 | 88 | 44 |
| MEK6 | 91 | 78 |
| MKK7 | 66 | 52 |
| MKNK2 | 66 | 43 |
| MLK2 | 100 | 95 |
| MRCKA | 95 | 89 |
| MUSK | 100 | 65 |
| NLK | 97 | 99 |
| PCTK3 | 100 | 100 |
| PHKG2 | 98 | 89 |
| PIK4CB | 0 | 28 |
| PKN2 | 100 | 95 |
| PRKCD | 100 | 100 |
| PRKG1 | 100 | 100 |
| PRP6 | 76 | 52 |
| RAF1 | 100 | 100 |
| SIK2 | 93 | 100 |
| SNARK | 68 | 53 |
| TEC | 100 | 100 |
| TNIK | 65 | 3.6 |
| TRKC | 39 | 11 |
| VEGFR2 | 20 | 3.5 |
| ZAP70 | 70 | 73 |

Scratch assay. PC3M cells were cultured for 48 hrs with genistein (10 µM), experimental compounds (10 or 25 µM)

or vehicle control, and subsequently scratch wound assays performed. Briefly, confluent monolayer of cells were wounded gently by scratching a 200-μL tip along the surface of the well. Wells were rinsed twice with PBS to remove debris. Media containing either genistein, inhibitors or control, was replenished. For each well, 32 images were obtained at 0 and 20 hrs after scratching. Images were imported into ImageJ for evaluation and wound healing determined by assessing the differences in wound gap between the 0 and corresponding 20 hr image. All experiments were conducted in a minimum of N=3 replicates.

TABLE 4

Wound Scratch Assay data for compounds 6ff and 6ee.

| | NUCC-201177 (6ff) | | NUCC-201167 (6ee) | |
|---|---|---|---|---|
| | Percent Difference | t.test | Percent Difference | t.test |
| DMSO vs. 10 uM inhibitor | −1.65 | 1.53E−01 | 14.93 | 5.58E−47 |
| DMSO vs. 25 uM inhibitor | −0.16 | 9.26E−01 | 32.15 | 1.83E−114 |

| | Percent Difference | t.test |
|---|---|---|
| DMSO vs. Geni | 33.45 | 9.90E−68 |

Cell viability. To determine cell viability, PC3M cells were seeded in 6-well plates ($1.5 \times 10^5$ cells/well) overnight before complete medium containing genistein (10 μM), experimental compounds (10 or 25 μM) or vehicle control was added. Cells were cultured for 72 hrs at which point cell viability determined utilizing trypan blue exclusion.

General Chemical Synthesis Information. All chemical reagents were obtained from commercial suppliers and used without further purification unless otherwise stated. Anhydrous solvents were purchased from Sigma-Aldrich, and dried over 3 Å molecular sieves when necessary. Normal-phase flash column chromatography was performed using Biotage KP-Sil 50 μm silica gel columns and ACS grade solvents on a Biotage Isolera flash purification system. Reverse phase preparative HPLC was performed with the following conditions: Phenomenex Kinetex C18 50×30 mm; 5 μm. Eluting with a gradient of 15-80% acetonitrile:water with 0.1% formic acid over 7 min, then 1 min at 100% acetonitrile. The flow rate was 50 mL/min. Analytical thin layer chromatography (TLC) was performed on EM Reagent 0.25 mm silica gel 60 $F_{254}$ plates and visualized by UV light. Proton (H), and carbon ($^{13}$C) NMR spectra were recorded on a 500 MHz Bruker Advance III with direct cryoprobe spectrometer. Chemical shifts were reported in ppm (δ) and were referenced using residual non-deuterated solvent as an internal standard (CDCl$_3$ at 7.24 ppm for $^1$H-NMR and 77.0 for $^{13}$C-NMR. CD$_3$OD at 3.33 ppm for $^1$H-NMR and 47.6 for $^{13}$C-NMR. DMSO-d$_6$ at 2.52 ppm for $^1$H-NMR and 39.9 ppm for $^{13}$C-NMR). Proton coupling constants are expressed in hertz (Hz). The following abbreviations were used to denote spin multiplicity for proton NMR: s=singlet, d=doublet, t=triplet, q=quartet, m=multiplet, brs=broad singlet, dd=doublet of doublets, dt=doublet of triplets, quin=quintet, tt=triplet of triplets. Low resolution liquid chromatography/mass spectrometry (LCMS) was performed on a Waters Acquity-H UPLC/MS system with a 2.1 mm×50 mm, 1.7 μm, reversed phase BEH C18 column and LCMS grade solvents. A gradient elution from 95% water+0.1% formic acid/5% acetonitrile+0.1% formic acid to 95% acetonitrile+0.1% formic acid/5% water+0.1% formic acid over 2 min plus a further minute continuing this mixture at a flow rate of 0.85 mL/min was used as the eluent. Total ion current traces were obtained for electrospray positive and negative ionization (ESI+/ESI−). High-resolution mass spectra were obtained using an Agilent 6210 LC-TOF spectrometer in the positive ion mode using electrospray ionization with an Agilent G1312A HPLC pump and an Agilent G1367B autoinjector at the Integrated Molecular Structure Education and Research Center (IMSERC), Northwestern University. Melting point ranges were measured with a Buchi Melting Point M-565 apparatus and are uncorrected. All microwave-assisted reactions were carried out in a Biotage® initiator. All compounds tested in biological assays were >95% pure based on HPLC unless otherwise noted. Compounds 6b and 6o were purchased from Chembridge Corp. and used as is in biological experiments after confirming their purity was >95% by LC/MS.

Synthesis of Intermediates
General Procedure A

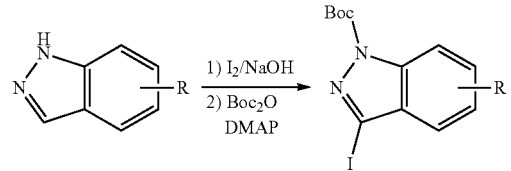

To a solution of the indazole (1.0 equiv) in MeOH (3.2 mL/mmol) and 2 M NaOH (3.2 mL/mmol) was added I$_2$ (1.3 equiv) portionwise over 20 min. After 24 h, the reaction mixture was cooled to 0° C. and concentrated HCl (4.0 equiv) was added slowly followed by 2 M HCl solution (1.0 equiv). To the suspension was added saturated aqueous sodium thiosulfate solution. After stirring for 20 minutes, the mixture was filtered and the filter cake was collected, washed with water, and dried to give the respective iodinated indazoles.

To a solution of the iodinated indazole (1.0 equiv) in acetonitrile (3.2 mL/mmol) was added DIEA (2.0 equiv) and DMAP (0.1 equiv). Boc-anhydride (2.0 equiv) was added and the reaction mixture was stirred for 16 h after which it was diluted with DCM and saturated aqueous NH$_4$Cl solution. The organic layer was washed with water, brine, filtered through an isolute phase separator, and concentrated. The residue was purified by silica gel purification eluting with 0-100% ethyl acetate in hexanes to give the respective Boc-protected iodinated indazoles.

General Procedure B

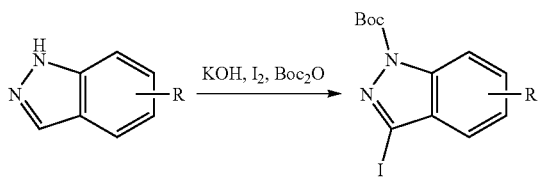

To a solution of the indazole (1.0 eqiuv) in DMF (3.6 mL/mmol) was added KOH (2.0 equiv) and iodine (1.1 equiv) and the mixture was stirred until starting material was consumed (TLC, 1:1 EtOAc:Hex). At this time, Boc$_2$O (1.2 equiv) was added and the reaction mixture was stirred until the reaction was complete (usually 1 hr). An aqueous solution of sodium thiosulfate was added and the reaction mixture was extracted with ethyl acetate (×3), washed with brine, and dried (MgSO₄). All solvents were removed under reduced pressure and the residue was purified by silica gel column chromatography eluting with 0-10% ethyl acetate in hexanes to give the respective Boc-protected iodinated indazoles.

tert-butyl 4-chloro-3-iodo-1H-indazole-1-carboxylate

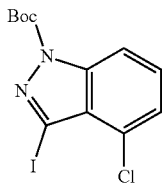 [SMILES: CC(C)(C)OC(=O)n1nc(I)c2c(Cl)cccc21]

Prepare according to genera procedure A using 4-chloro-1H-indazole (500 mg, 3.28 mmol) to afford tert-butyl 4-chloro-3-iodo-H-indazole-1-carboxylate (261 mg, 21%).

$^1$H NMR (500 MHz, Chloroform-d) δ 8.15 (d, J=8.5 Hz, 1H), 7.42 (dd, J=8.5, 7.6 Hz, 1H), 7.28 (d, J=7.6 Hz, 1H), 1.69 (s, 9H).

tert-butyl 3-iodo-5-(trifluoromethyl)-1H-indazole-1-carboxylate

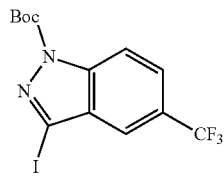

Prepared according to general procedure A using 5-(trifluoromethyl)-1H-indazole (500 mg, 2.69 mmol) to afford tert-butyl 3-iodo-5-(trifluoromethyl)-1H-indazole-1-carboxylate (793 mg, 72%).

$^1$H NMR (500 MHz, Chloroform-d) δ 8.25 (d, J=9.2 Hz, 1H), 7.80 (m, 2H), 1.71 (s, 9H).

tert-butyl 3-iodo-5-methyl-1H-indazole-1-carboxylate

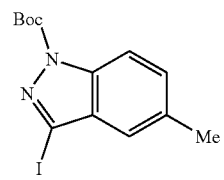

Prepared according to general procedure A using 5-methyl-H-indazole (500 mg, 3.78 mmol) to afford tert-butyl 3-iodo-5-methyl-1H-indazole-1-carboxylate (850 mg, 63%).

$^1$H NMR (500 MHz, Methanol-d₄) δ 8.00 (d, J=8.6 Hz, 1H), 7.51 (dd, J=8.6, 1.6 Hz, 1H), 7.32 (dt, J=1.8, 0.8 Hz, 1H), 2.52 (s, 3H), 1.73 (s, 9H).

tert-butyl 6-fluoro-3-iodo-1H-indazole-1-carboxylate

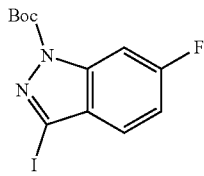 [SMILES: CC(C)(C)OC(=O)n1nc(I)c2ccc(F)cc21]

Prepared according to general procedure A using 6-fluoro-1H-indazole (500 mg, 3.67 mmol) to afford tert-butyl 6-fluoro-3-iodo-1H-indazole-1-carboxylate (760 mg, 57%).

$^1$H NMR (500 MHz, Chloroform-d) δ 7.81 (dd, J=9.6, 2.2 Hz, 1H), 7.44 (dd, J=8.8, 5.0 Hz, 1H), 7.11 (td, J=8.8, 2.2 Hz, 1H), 1.70 (s, 9H).

tert-butyl 3-iodo-6-(trifluoromethyl)-1H-indazole-1-carboxylate

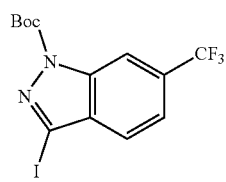 [SMILES: CC(C)(C)OC(=O)n1nc(I)c2ccc(C(F)(F)F)cc21]

Prepared according to general procedure B using 6-trifluoromethyl-1H-indazole (333 mg, 1.79 mmol) to afford tert-butyl 3-iodo-6-(trifluoromethyl)-1H-indazole-1-carboxylate (543 mg, 73.6%).

$^1$H NMR (500 MHz, Chloroform-d) δ 8.48 (s, 1H), 7.62 (d, J=8.4 Hz, 1H), 7.59 (dd, J=8.5, 1.4 Hz, 1H), 1.72 (s, 9H).

tert-butyl 6-chloro-3-iodo-1H-indazole-1-carboxylate

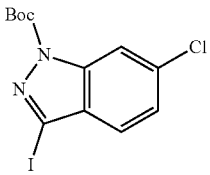

Prepared according to general procedure B using 6-chloro-1H-indazole (333 mg, 2.18 mmol) to afford tert-butyl 6-chloro-3-iodo-H-indazole-1-carboxylate (540 mg, 65%).

$^1$H NMR (500 MHz, Chloroform-d) δ 8.17 (d, J=1.8 Hz, 1H), 7.42-7.36 (m, 1H), 7.33 (dd, J=8.5, 1.7 Hz, 1H), 1.70 (s, 9H).

Synthesis of Final Compounds
Suzuki Procedure C

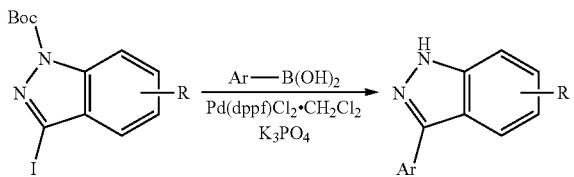

To a microwave vial was added the Boc-protected iodinated indazole (1.0 equiv), PdCl$_2$(dppf)-DCM (0.05 equiv), aryl boronic acid (1.2 equiv), K$_3$PO$_4$ (2.0 equiv) and 1,4-dioxane/water (5:1; 6 mL/mmol). The vial was degassed under nitrogen gas for 5 minutes after which it was irradiated in the microwave reactor at 90° C. for 1 h. The reaction mixture was diluted with DCM and water. The organic layer was washed with brine, filtered through an isolute phase separator, concentrated and purified by reverse phase HPLC eluting with 15 to 80% acetonitrile in water (0.1% formic acid conditions) to give the respective products.

In some cases, the Boc-group came off during the course of the Suzuki reaction and the material resulting from the preparative HPLC was the desired N—H indazole final product. In cases where the Boc-group survived the Suzuki reaction conditions, the Boc-protected compound resulting from the Suzuki reaction (1.0 equiv) was dissolved in DCM (10 mL/mmol), treated with TFA (10.0 equiv), and the reaction mixture was stirred at room temperature for 16 h after which the reaction mixture was concentrated and dried under high vacuum to yield the respective deprotected indazoles.

Suzuki Procedure D

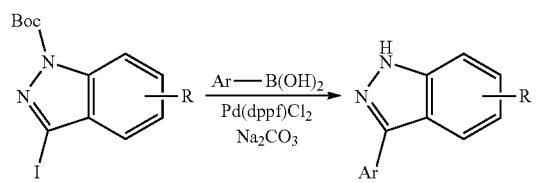

To a vial was added the Boc-protected iodinated indazole (1.0 equiv), PdCl$_2$(dppf) (0.1 equiv), aryl boronic acid (1.0 equiv), Na$_2$CO$_3$ (3.0 equiv) and toluene/ethanol/water (1:1:1; 4 ml/mmol). The vial was degassed under argon gas for 15 minutes after which it was heated at 75° C. for 16 h. The reaction mixture was diluted with EtOAc and saturated aqueous NH$_4$Cl solution after which the organic layer was removed, washed twice with water, then brine. The organic layer was dried (Na$_2$SO$_4$), filtered, concentrated and purified by silica gel chromatography eluting with 0-100% EtOAc in hexanes. The resulting material was then purified by reverse phase HPLC eluting with 15-80% acetonitrile in water (0.1% formic acid conditions) to give the respective products.

In some cases, the Boc-group came off during the course of the Suzuki reaction and the material resulting from the preparative HPLC was the desired N—H indazole final product. In cases where the Boc-group survived the Suzuki reaction conditions, the Boc-protected compound resulting from the suzuki reaction (1.0 equiv) was dissolved in DCM (10 mL/mmol), treated with TFA (10.0 equiv), and reaction mixture was stirred at room temperature for 16 h. The reaction mixture was concentrated and dried under high vacuum to yield the respective deprotected indazoles.

Suzuki Procedure E

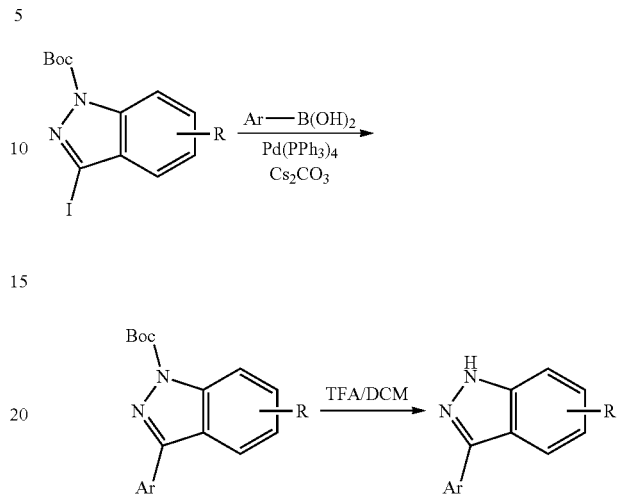

To a vial was added the Boc-protected iodinated indazole (1.0 equiv), Pd(PPh$_3$)$_4$ (0.05 equiv), aryl boronic acid (2.5 equiv), Cs$_2$CO$_3$ (3.0 equiv), and 1,2-dimethoxyethane/water (4:1; 7.7 ml/mmol). The reaction mixture was degassed under argon gas for 15 min after which it was heated at 90° C. for 16 h. The reaction was then worked up and purified as per Suzuki method D to afford the desired products. In this procedure, the Boc group was not lost and TFA deprotection was carried out as described in procedures C and D to give the final N—H indazole.

Methyl Ester Hydrolysis Procedure F

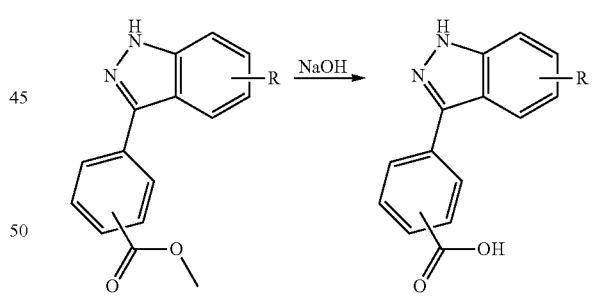

To a solution of the methyl ester indazole (1.0 equiv) in MeOH/THF (1:1; 10 mL/mmol) was added 1 M NaOH (8.0 equiv) and the reaction mixture was stirred at room temperature for 16 h after which the reaction mixture was acidified with 1 M HCl (pH 2). The mixture was filtered and the isolated solids washed with water and dried under high vacuum to give the desired carboxylic acids.

The following compounds were all prepared according to the general methods described above unless otherwise noted.

3-(1H-indazol-3-yl)benzoic Acid (6a)

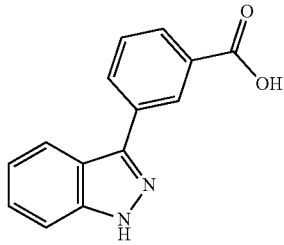 [SMILES: O=C(O)c1cccc(-c2n[nH]c3ccccc23)c1]

Suzuki procedure C yielded tert-butyl 3-(3-(methoxycarbonyl)phenyl)-1H-indazole-1-carboxylate (53 mg, 0.15 mmol, 52%), which was subjected to TFA deprotection followed by methyl ester hydrolysis via procedure F to give the title compound (28 mg, 78% over 2 steps).

$^1$H NMR (500 MHz, DMSO-d$_6$) δ 13.42 (s, 1H), 8.56 (s, 1H), 8.25 (d, J=7.7 Hz, 1H), 8.07 (d, J=8.2 Hz, 1H), 7.97 (d, J=7.7 Hz, 1H), 7.72-7.58 (m, 2H), 7.49-7.38 (m, 1H), 7.26 (t, J=7.5 Hz, 1H).

$^{13}$C NMR (126 MHz, DMSO) δ 167.69, 142.63, 142.11, 134.53, 131.85, 131.31, 129.82, 128.83, 127.71, 126.74, 121.85, 120.74, 120.37, 111.29.

Melting point range (° C.): 244-246.5

HRMS (ES)): mass calc for $C_{14}H_{10}N_2O_2^+$ [M+H]$^+$=239.0815, found=239.0821.

3-(2H-1,3-benzodioxol-5-yl)-4-chloro-2H-indazole (6c)

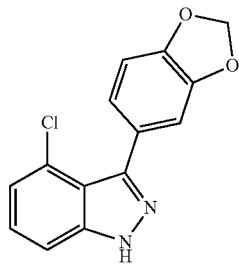 [SMILES: Clc1cccc2[nH]nc(-c3ccc4c(c3)OCO4)c12]

Suzuki procedure C yielded tert-butyl 3-(benzo[d][1,3]dioxol-5-yl)-4-chloro-1H-indazole-1-carboxylate (12 mg, 0.13 mmol, 25%) which was subjected to TFA deprotection to give 3-(benzo[d][1,3]dioxol-5-yl)-4-chloro-1H-indazole (11 mg, 31% over 2 steps)

$^1$H NMR (500 MHz, Methanol-d$_4$) δ 7.50 (d, J=8.4 Hz, 1H), 7.39-7.30 (m, 1H), 7.19-7.05 (m, 3H), 6.92 (d, J=7.9 Hz, 1H), 6.03 (s, 2H).

$^{13}$C NMR (126 MHz, CD$_3$OD) δ 147.90, 147.07, 145.28, 142.75, 127.19, 126.75, 126.40, 124.23, 121.41, 118.28, 110.64, 108.95, 107.15, 101.18.

Melting point range (° C.): 145-147.

HRMS (ES)): mass calc for $C_{14}H_9ClN_2O_2^+$ [M+H]$^+$=273.0425, found=273.0428.

4-(4-chloro-1H-indazol-3-yl)benzamide (6d)

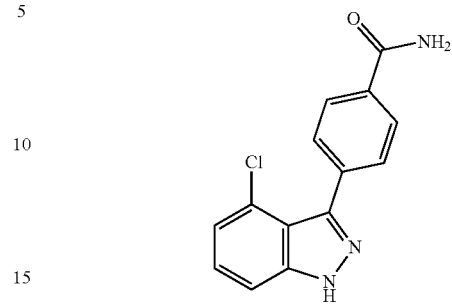

Suzuki procedure D yielded 4-(4-chloro-1H-indazol-3-yl)benzamide (2 mg, 2.4%).

Note: for this reaction, the unprotected iodinated indazole was used.

$^1$H NMR (500 MHz, Methanol-d$_4$) δ 8.05-7.94 (m, 2H), 7.85-7.74 (m, 2H), 7.57 (d, J=8.3 Hz, 1H), 7.40 (dd, J=8.4, 7.4 Hz, 1H), 7.21 (d, J=7.4 Hz, 1H).

$^{13}$C NMR (126 MHz, CD$_3$OD) δ 170.72, 168.95, 142.89, 136.83, 133.20, 130.42, 127.30, 126.60, 126.17, 121.69, 118.35, 109.09.

Melting point range (° C.): 216-218.

HRMS (ES)): mass calc for $C_{14}H_{10}ClN_3O^+$ [M+H]$^+$=272.0585, found=272.0589.

4-chloro-3-(pyridin-3-yl)-2H-indazole (6e)

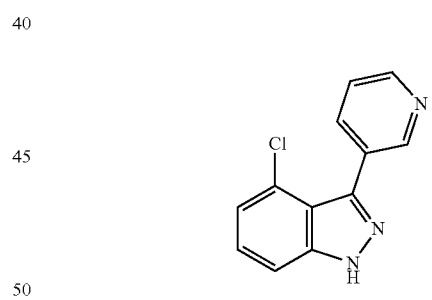

Suzuki procedure C yielded 4-chloro-3-(pyridin-3-yl)-2H-indazole (10 mg, 33%).

$^1$H NMR (500 MHz, DMSO-d$_6$) δ 8.84 (d, J=2.3 Hz, 1H), 8.64 (d, J=4.6 Hz, 1H), 8.12-8.01 (m, 1H), 7.63 (d, J=8.4 Hz, 1H), 7.53 (dd, J=7.9, 4.7 Hz, 1H), 7.45-7.32 (m, 1H), 7.24 (d, J=7.3 Hz, 1H).

$^{13}$C NMR (126 MHz, DMSO) δ 150.81, 149.34, 143.24, 141.72, 138.12, 129.76, 127.78, 125.34, 123.34, 122.05, 118.68, 110.571

Melting point range (° C.): 260-262.

HRMS (ES)): mass calc for $C_{12}H_8ClN_3^+$ [M+H]$^+$=230.0480, found=230.0479.

[3-(4-chloro-2H-indazol-3-yl)phenyl]methanol (6f)

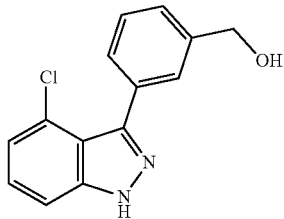 [SMILES: OCc1cccc(-c2n[nH]c3cccc(Cl)c23)c1]

Suzuki procedure D yielded [3-(4-chloro-2H-indazol-3-yl)phenyl]methanol (4 mg, 4%).

Note: for this reaction, the unprotected iodinated indazole was used.

$^1$H NMR (500 MHz, Methanol-$d_4$) δ 7.67 (s, 1H), 7.60-7.51 (m, 2H), 7.46 (d, J=5.9 Hz, 2H), 7.38 (t, J=7.9 Hz, 1H), 7.18 (d, J=7.3 Hz, 1H), 4.71 (s, 2H).

$^{13}$C NMR (126 MHz, CD$_3$OD) δ 168.87, 145.61, 142.78, 140.85, 133.19, 129.31, 128.92, 127.27, 127.19, 126.43, 121.43, 118.36, 108.94, 63.72.

Melting point range (° C.): 158.4-159.9.

HRMS (ES)): mass calc for C$_{14}$H$_{11}$ClN$_2$O$^+$ [M+H]$^+$=259.0633, found=259.0638.

2-[3-(4-chloro-2H-indazol-3-yl)phenyl]propan-2-ol (6g)

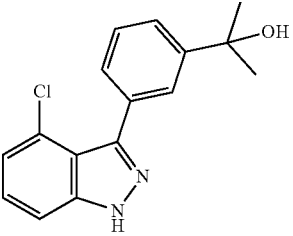 [SMILES: CC(C)(O)c1cccc(-c2n[nH]c3cccc(Cl)c23)c1]

Suzuki procedure D yielded 2-[3-(4-chloro-2H-indazol-3-yl)phenyl]propan-2-ol (3 mg, 6%).

Note: for this reaction, the unprotected iodinated indazole was used.

$^1$H NMR (500 MHz, Methanol-$d_4$) δ 7.80 (t, J=1.8 Hz, 1H), 7.62 (dt, J=8.0, 1.6 Hz, 1H), 7.53 (ddd, J=7.6, 3.8, 2.3 Hz, 2H), 7.44 (t, J=7.7 Hz, 1H), 7.38 (dd, J=8.4, 7.4 Hz, 1H), 7.18 (d, J=7.3 Hz, 1H), 1.61 (s, 6H).

$^{13}$C NMR (126 MHz, CD$_3$OD) δ 168.76, 148.86, 145.92, 142.80, 132.70, 128.30, 127.18, 127.02, 126.47, 124.09, 121.43, 118.34, 108.95, 71.57, 30.48.

Melting point range (° C.): 179-181

HRMS (ES)): mass calc for C$_{16}$H$_{15}$ClN$_2$O$^+$ [M+H]$^+$=287.0946, found=287.0948.

3-(4-chloro-2H-indazol-3-yl)benzamide (6h)

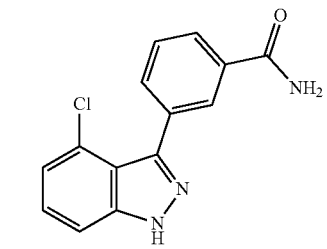 [SMILES: NC(=O)c1cccc(-c2n[nH]c3cccc(Cl)c23)c1]

Suzuki procedure D yielded 3-(4-chloro-2H-indazol-3-yl)benzamide (2 mg, 3%).

Note: for this reaction, the unprotected iodinated indazole was used.

$^1$H NMR (500 MHz, Methanol-$d_4$) δ 8.22 (d, J=1.8 Hz, 1H), 7.99 (dt, J=7.8, 1.5 Hz, 1H), 7.87 (dt, J=7.7, 1.4 Hz, 1H), 7.68-7.51 (m, 2H), 7.40 (dd, J=8.4, 7.4 Hz, 1H), 7.20 (d, J=7.4 Hz, 1H).

$^{13}$C NMR (126 MHz, CD$_3$OD) δ 170.62, 168.87, 142.88, 133.71, 133.63, 133.08, 129.57, 127.49, 127.28, 127.02, 126.24, 121.57, 118.36, 109.10.

Melting point range (° C.): 219-221.

HRMS (ES)): mass calc for C$_{14}$H$_{10}$ClN$_3$O$^+$ [M+H]$^+$=272.0585, found=272.0588.

[4-(4-chloro-2H-indazol-3-yl)phenyl]methanol (6i)

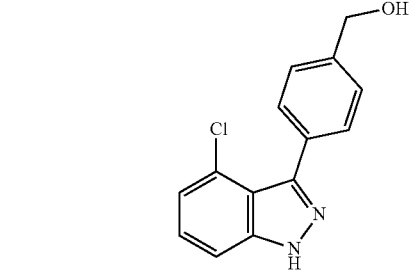 [SMILES: OCc1ccc(-c2n[nH]c3cccc(Cl)c23)cc1]

Suzuki procedure C yielded [4-(4-chloro-2H-indazol-3-yl)phenyl]methanol (8 mg, 23%)

The Boc-protected compound was also isolated: tert-butyl 4-chloro-3-(4-(hydroxymethyl)phenyl)-1H-indazole-1-carboxylate (9 mg, 19%).

$^1$H NMR (500 MHz, Methanol-$d_4$) δ 7.68-7.62 (m, 2H), 7.53 (d, J=8.4 Hz, 1H), 7.48 (d, J=7.9 Hz, 2H), 7.36 (dd, J=8.4, 7.4 Hz, 1H), 7.16 (d, J=7.4 Hz, 1H), 4.72 (s, 2H).

$^{13}$C NMR (126 MHz, CD$_3$OD) δ 145.50, 142.78, 141.50, 132.10, 130.36, 127.18, 126.42, 125.83, 121.41, 118.37, 108.95, 63.62.

Melting point range (C): 169-171

HRMS (ES)): mass calc for C$_{14}$H$_{11}$ClN$_2$O$^+$ [M+H]$^+$=259.0633, found=259.0637.

4-[5-(trifluoromethyl)-2H-indazol-3-yl]phenol (6j)

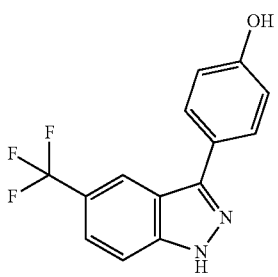 [SMILES: Oc1ccc(-c2n[nH]c3ccc(C(F)(F)F)cc23)cc1]

Suzuki procedure D followed by deprotection with TFA yielded 4-[5-(trifluoromethyl)-2H-indazol-3-yl]phenol (3 mg, 3%).

$^1$H NMR (500 MHz, Methanol-$d_4$) δ 8.26 (s, 1H), 7.77 (d, J=8.5 Hz, 2H), 7.72 (d, J=8.8 Hz, 1H), 7.66 (dd, J=8.8, 1.5 Hz, 1H), 6.99 (d, J=8.4 Hz, 2H).

$^{13}$C NMR (126 MHz, CD$_3$OD) δ 158.05, 146.21, 142.77, 128.57, 124.96 (q, J=271 Hz), 123.71, 122.85 (q, J=31.97 Hz), 122.69 (q, J=3.15 Hz), 119.46, 118.79 (q, J=4.56 Hz), 115.52, 111.09.

Melting point range (° C.): 177.6-179.9

HRMS (ES)): mass calc for C$_{14}$H$_9$F$_3$N$_2$O$^+$ [M+H]$^+$=279.0740, found=279.0740.

tert-butyl 3-(4-hydroxyphenyl)-5-(trifluoromethyl)-1H-indazole-1-carboxylate (6k)

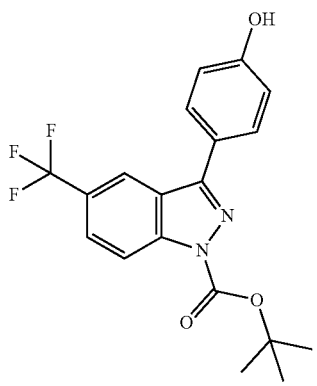 [SMILES: CC(C)(C)OC(=O)n1nc(-c2ccc(O)cc2)c2cc(C(F)(F)F)ccc21]

Suzuki procedure D yielded tert-butyl 3-(4-hydroxyphenyl)-5-(trifluoromethyl)-1H-indazole-1-carboxylate (9 mg, 10%).

$^1$H NMR (500 MHz, Methanol-$d_4$) δ 8.37 (d, J=8.8 Hz, 1H), 8.27 (s, 1H), 7.89 (dd, J=8.9, 1.6 Hz, 1H), 7.86-7.80 (m, 2H), 7.06-6.95 (m, 2H), 1.77 (s, 9H).

$^{13}$C NMR (126 MHz, CD$_3$OD) δ 159.24, 150.22, 148.90, 142.05, 129.39, 125.96 (q, $^2$J (C,F)=32.52 Hz), 125.30 (q, $^3$J (C,F)=3.78 Hz), 124.36 (q, $^1$J (C,F)=271.58 Hz), 123.58, 121.71, 119.07 (q, $^3$J (C,F)=3.78 Hz), 115.62, 115.37, 85.65, 26.92.

Melting point range (° C.): 122-125

HRMS (ES)): mass calc for C$_{19}$H$_7$F$_3$N$_2$O$_3^+$ [M+H]$^+$=379.1264, found=379.1266.

tert-butyl 3-(3-carbamoylphenyl)-5-(trifluoromethyl)-1H-indazole-1-carboxylate (6l)

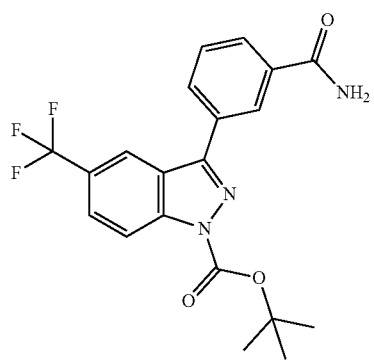 [SMILES: CC(C)(C)OC(=O)n1nc(-c2cccc(C(N)=O)c2)c2cc(C(F)(F)F)ccc21]

Route used:

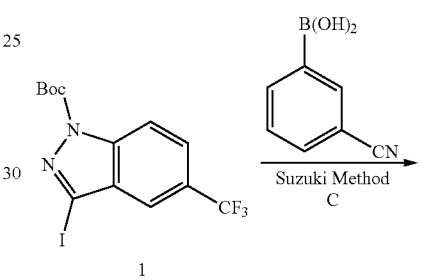

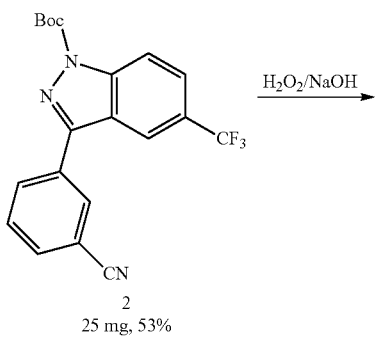

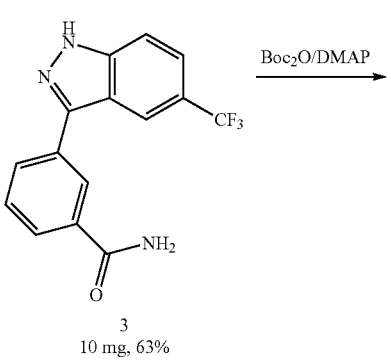

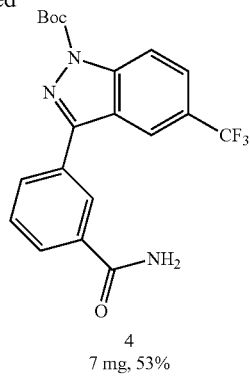

4
7 mg, 53%

Starting with Boc-protected indazole 1, Suzuki procedure C yielded nitrile 2, tert-butyl 3-(3-cyanophenyl)-5-(trifluoromethyl)-1H-indazole-1-carboxylate (25 mg, 0.065 mmol, 53%). To compound 2, water (0.3 mL) and EtOH (0.3 mL) were added followed by NaOH (4 mg, 0.1 mmol, 2.0 eqiuv) and 30% $H_2O_2$ (11 μL, 0.1 mmol, 2.0 equiv). The reaction mixture was stirred at room temperature for 2 hours after which it was purified by reverse phase HPLC eluting with 5-80% acetonitrile in water (0.1% formic acid conditions) to give 3-(5-(trifluoromethyl)-1H-indazol-3-yl)benzamide (3, 10 mg, 63%). To this, DMF (0.7 mL), DMAP (1 mg, 8 μmol, 0.25 equiv), Boc$_2$O (10 μL, 43 μmol, 1.3 equiv), and DIEA (11 μL, 66 μmol, 2.0 equiv) were added. The reaction mixture was stirred at room temperature for 2 h, then purified by reverse phase HPLC eluting with 30-95% acetonitrile in water (0.1% formic acid conditions) to give tert-butyl 3-(3-carbamoylphenyl)-5-(trifluoromethyl)-1H-indazole-1-carboxylate (4, 7 mg, 53%).

$^1$H NMR (500 MHz, DMSO-d$_6$) δ 8.41 (m, 3H), 8.30-7.98 (m, 4H), 7.72 (t, J=7.7 Hz, 1H), 7.54 (s, 1H), 1.71 (s, 9H).

$^{13}$C NMR (126 MHz, DMSO) δ 167.84, 149.17, 148.59, 142.42, 135.70, 131.31, 131.03, 129.81, 129.27, 127.43, 126.37 (q, $^3$J (C,F)=3.29 Hz), 125.50 (q, $^2$J (C,F)=32.17), 124.76 (q, $^1$J (C,F)=272.6 Hz), 123.41, 119.85 (q, $^3$J (C,F)=3.17 Hz), 116.27, 86.18, 28.14.

Melting point range (° C.): 242-244.

HRMS (ES)): mass calc for $C_{20}H_{18}F_3N_3O_3^+$ [M+Na]$^+$=428.1192, found=428.1194.

4-[5-(trifluoromethyl)-2H-indazol-3-yl]benzamide (6m)

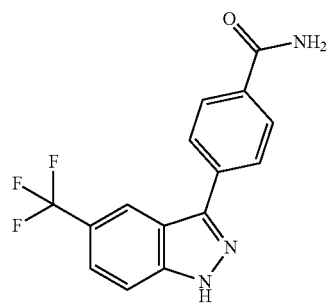 [SMILES: NC(=O)c1ccc(-c2n[nH]c3ccc(C(F)(F)F)cc23)cc1]

Suzuki procedure D yielded 4-[5-(trifluoromethyl)-2H-indazol-3-yl]benzamide (6 mg, 8%).

$^1$H NMR (500 MHz, DMSO-d$_6$) δ 8.44 (s, 1H), 8.11 (d, J=8.2 Hz, 2H), 8.08 (s, 1H), 8.05 (d, J=8.2 Hz, 2H), 7.84 (d, J=8.8 Hz, 1H), 7.72 (d, J=8.6 Hz, 1H), 7.43 (s, 1H).

$^{13}$C NMR (126 MHz, DMSO) δ 168.03, 144.34, 143.16, 135.76, 134.22, 128.73, 127.19, 125.38 (q, $^1$J (C,F)=272.21 Hz), 123.08 (q, $^3$J (C,F)=2.67 Hz), 122.57 (q, $^2$J (C,F)=31.42 Hz), 119.70, 119.31 (q, $^3$J (C,F)=4.19 Hz), 112.64.

Melting point range (° C.): 313-315.

HRMS (ES)): mass calc for $C_{15}H_{10}F_3N_3O^+$ [M+H]$^+$=306.0849, found=306.0851.

4-[5-(trifluoromethyl)-2H-indazol-3-yl]benzoic Acid (6n)

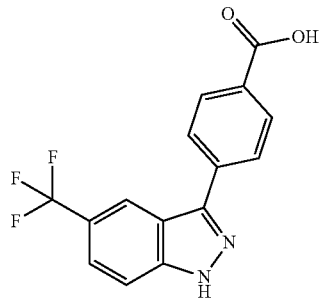 [SMILES: O=C(O)c1ccc(-c2n[nH]c3ccc(C(F)(F)F)cc23)cc1]

Suzuki procedure C yielded tert-butyl 3-(4-(methoxycarbonyl)phenyl)-5-(trifluoromethyl)-1H-indazole-1-carboxylate (30 mg, 71 μmol). After TFA deprotection followed by hydrolysis procedure F, 4-(5-(trifluoromethyl)-1H-indazol-3-yl)benzoic acid (14 mg, 38% over 3 steps) was obtained.

Note: a HPLC purification was not performed in Suzuki procedure C for this compound. Rather, upon completion of the suzuki reaction, water was added to the solution and the mixture was filtered to isolate the product as a solid.

$^1$H NMR (500 MHz, Methanol-d$_4$) δ 8.38 (dt, J=2.0, 1.0 Hz, 1H), 8.25-8.18 (m, 2H), 8.13-8.06 (m, 2H), 7.78 (dt, J=8.8, 0.9 Hz, 1H), 7.71 (dd, J=8.8, 1.6 Hz, 1H).

$^{13}$C NMR (126 MHz, CD$_3$OD) δ 168.30, 144.67, 142.90, 137.07, 130.58, 130.03, 126.91, 124.87 (q, J=271.39 Hz), 123.58 (q, J=32.05 Hz), 122.82 (q, J=3.15 Hz), 119.61, 118.49 (q, J=4.57 Hz), 111.38.

Melting point range (° C.): 311-314

HRMS (ES)): mass calc for $C_{15}H_9F_3N_2O_2^+$ [M+H]$^+$=307.0689, found=307.0699.

3-(2H-1,3-benzodioxol-5-yl)-5-methyl-2H-indazole (6p)

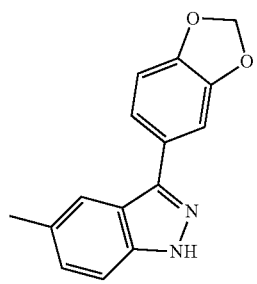 [SMILES: Cc1ccc2[nH]nc(-c3ccc4c(c3)OCO4)c2c1]

Suzuki procedure C yielded tert-butyl 3-(benzo[d][1,3]dioxol-5-yl)-5-methyl-1H-indazole-1-carboxylate (23 mg, 47%). TFA deprotection yielded 3-(benzo[d][1,3]dioxol-5-yl)-5-methyl-H-indazole (12 mg, 34% over 2 steps).

$^1$H NMR (500 MHz, Methanol-$d_4$) δ 7.72 (s, 1H), 7.46-7.38 (m, 2H), 7.36 (d, J=1.7 Hz, 1H), 7.26 (d, J=8.4 Hz, 1H), 6.97 (d, J=8.0 Hz, 1H), 6.02 (s, 2H), 2.47 (s, 3H).

$^{13}$C NMR (126 MHz, CD$_3$OD) δ 148.15, 147.56, 143.84, 140.54, 130.42, 128.53, 127.64, 120.92, 120.46, 119.34, 109.71, 108.10, 107.27, 101.15, 20.17.

Melting point range (° C.): 132.4-133.4.

HRMS (ES)): mass calc for $C_{15}H_{12}N_2O_2^+$ [M+H]$^+$=253.0972, found=253.0976.

4-(5-methyl-2H-indazol-3-yl)phenol (6q)

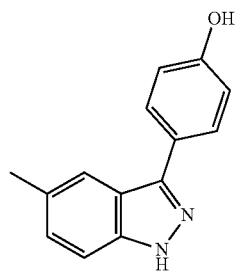 [SMILES: Cc1ccc2[nH]nc(-c3ccc(O)cc3)c2c1]

Suzuki procedure C yielded 4-(5-methyl-1H-indazol-3-yl)phenol (15 mg, 48%).

Note: The Boc-protected compound, tert-butyl 3-(4-hydroxyphenyl)-5-methyl-1H-indazole-1-carboxylate (24 mg, 53%), was also isolated.

$^1$H NMR (500 MHz, Methanol-$d_4$) δ 7.75 (m, 3H), 7.44 (d, J=8.5 Hz, 1H), 7.27 (d, J=8.5 Hz, 1H), 6.95 (d, J=8.2 Hz, 2H), 2.49 (s, 3H).

$^{13}$C NMR (126 MHz, CD$_3$OD) δ 157.29, 144.39, 140.45, 130.17, 128.48, 128.41, 124.92, 120.55, 119.53, 115.22, 109.58, 20.16.

Melting point range (° C.): 197.4-199.0

HRMS (ES)): mass calc for $C_{14}H_{12}N_2O^+$ [M+H]$^+$=225.1022, found=225.1022.

4-(5-methyl-2H-indazol-3-yl)benzamide (6r)

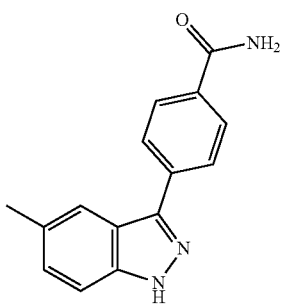 [SMILES: Cc1ccc2[nH]nc(-c3ccc(C(N)=O)cc3)c2c1]

Suzuki procedure C yielded 4-(5-methyl-H-indazol-3-yl)benzamide (4 mg, 11%).

Note: The Boc-protected compound, tert-butyl 3-(4-carbamoylphenyl)-5-methyl-1H-indazole-1-carboxylate (15 mg, 31%) was also isolated.

$^1$H NMR (500 MHz, Methanol-$d_4$) δ 8.08 (d, J=8.5 Hz, 2H), 8.04 (d, J=8.5 Hz, 2H), 7.85 (q, J=1.1 Hz, 1H), 7.50 (d, J=8.5 Hz, 1H), 7.32 (dd, J=8.6, 1.4 Hz, 1H), 2.52 (s, 3H).

$^{13}$C NMR (126 MHz, CD$_3$OD) δ 170.64, 142.80, 140.60, 137.28, 132.56, 131.04, 128.62, 127.83, 126.79, 120.72, 119.21, 109.87, 20.20.

Melting point range (° C.): 275-277.

HRMS (ES)): mass calc for $C_{15}H_{13}N_3O^+$ [M+H]$^+$=252.1131, found=252.1134.

4-(5-methyl-2H-indazol-3-yl)benzoic Acid (6s)

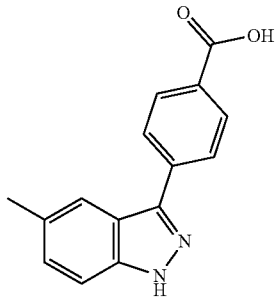 [SMILES: Cc1ccc2[nH]nc(-c3ccc(C(=O)O)cc3)c2c1]

Suzuki procedure C yielded tert-butyl 3-(4-(tert-butoxycarbonyl)phenyl)-5-methyl-1H-indazole-1-carboxylate (26 mg, 46%), to which TFA (64 µL, 10.0 equiv) were added and the reaction mixture was stirred for 16 h at room temperature then concentrated and dried to give 4-(5-methyl-2H-indazol-3-yl)benzoic acid (21 mg, quant.)

$^1$H NMR (500 MHz, Methanol-$d_4$) δ 8.21-8.16 (m, 2H), 8.11-8.06 (m, 2H), 7.86 (s, 1H), 7.50 (d, J=8.6 Hz, 1H), 7.32 (d, J=8.6 Hz, 1H), 2.52 (s, 3H).

$^{13}$C NMR (126 MHz, CD$_3$OD) δ 168.23, 142.68, 140.66, 138.26, 131.16, 129.88, 129.53, 128.68, 126.73, 120.73, 119.24, 109.94, 20.21.

Melting point range (° C.): 258-260

HRMS (ES)): mass calc for $C_{15}H_{12}N_2O_2^+$ [M+H]$^+$=253.0972, found=253.0977.

5-methyl-3-(pyridin-3-yl)-2H-indazole (6t)

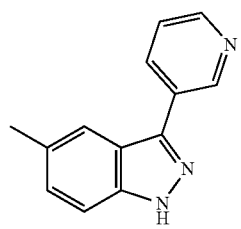 [SMILES: Cc1ccc2[nH]nc(-c3cccnc3)c2c1]

Suzuki procedure E yielded tert-butyl 5-methyl-3-(pyridin-3-yl)-1H-indazole-1-carboxylate (24 mg, 30%). TFA deprotection on 12 mg (0.039 mmol) of this material under the standard conditions yielded 5-methyl-3-(pyridin-3-yl)-2H-indazole (4 mg, 50%).

$^1$H NMR (500 MHz, Chloroform-d) δ 9.24 (d, J=2.2 Hz, 1H), 8.74-8.55 (m, 1H), 8.26 (dt, J=8.0, 2.0 Hz, 1H), 7.77 (s, 1H), 7.46-7.39 (m, 2H), 7.29-7.25 (m, 1H), 2.49 (s, 3H).

$^{13}$C NMR (126 MHz, CDCl$_3$) δ 148.92, 148.48, 142.20, 140.30, 134.60, 131.54, 129.89, 129.20, 123.76, 121.29, 119.73, 109.80, 21.53.

Melting point range (° C.): 165.5-167.6.

HRMS (ES)): mass calc for C$_{13}$H$_{11}$N$_3$$^+$ [M+H]$^+$=210.1026, found=210.1022.

[3-(5-methyl-2H-indazol-3-yl)phenyl]methanol (6u)

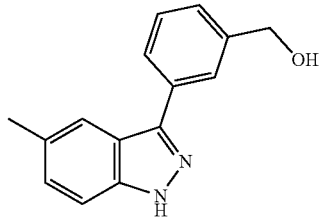 [SMILES: Cc1ccc2[nH]nc(-c3cccc(CO)c3)c2c1]

Suzuki procedure E yielded tert-butyl 3-(3-(hydroxymethyl)phenyl)-5-methyl-1H-indazole-1-carboxylate (37 mg, 42%) after which TFA deprotection under standard conditions yielded [3-(5-methyl-2H-indazol-3-yl)phenyl]methanol (5 mg, 19%).

$^1$H NMR (500 MHz, Chloroform-d) δ 7.96 (s, 1H), 7.87 (dt, J=7.8, 1.5 Hz, 1H), 7.77-7.74 (m, 1H), 7.48 (t, J=7.6 Hz, 1H), 7.40 (d, J=7.6 Hz, 1H), 7.32 (d, J=8.5 Hz, 1H), 7.21 (dd, J=8.5, 1.5 Hz, 1H), 4.78 (s, 2H), 2.47 (s, 3H).

$^{13}$C NMR (126 MHz, CDCl$_3$) δ 144.97, 141.61, 140.34, 133.95, 130.98, 129.05, 128.96, 126.82, 126.61, 126.05, 121.28, 120.13, 109.73, 65.32, 21.52.

Melting point range (° C.): 138-140.

HRMS (ES)): mass calc for C$_{15}$H$_{14}$N$_2$O$^+$ [M+H]$^+$=239.1179, found=239.1181.

3-(5-methyl-2H-indazol-3-yl)benzamide (6v)

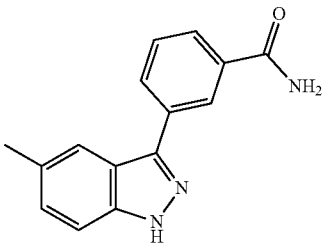 [SMILES: Cc1ccc2[nH]nc(-c3cccc(C(N)=O)c3)c2c1]

Suzuki procedure C yielded 3-(5-methyl-H-indazol-3-yl) benzamide (7 mg, 20%).

Note: The Boc-protected compound, tert-butyl 3-(3-carbamoylphenyl)-5-methyl-1H-indazole-1-carboxylate (23 mg, 47%) was also isolated.

$^1$H NMR (500 MHz, Methanol-d$_4$) δ 8.47 (t, J=1.8 Hz, 1H), 8.14 (dt, J=7.8, 1.4 Hz, 1H), 7.92 (dt, J=7.8, 1.4 Hz, 1H), 7.87 (q, J=1.2 Hz, 1H), 7.64 (t, J=7.8 Hz, 1H), 7.49 (d, J=8.5 Hz, 1H), 7.31 (dd, J=8.5, 1.4 Hz, 1H), 2.68-2.31 (m, 3H).

$^{13}$C NMR (126 MHz, CD$_3$OD) δ 170.89, 143.10, 140.57, 134.26, 134.24, 130.88, 130.27, 128.67, 128.63, 126.45, 126.20, 120.62, 119.23, 109.78, 20.15.

Melting point range (C): 243-246.

HRMS (ES)): mass calc for C$_{15}$H$_{13}$N$_3$O$^+$ [M+H]$^+$=252.1131, found=252.1130.

[4-(5-methyl-2H-indazol-3-yl)phenyl]methanol (6w)

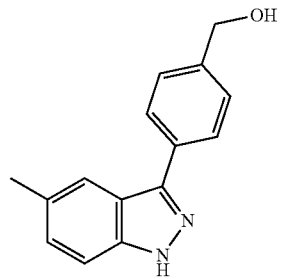 [SMILES: Cc1ccc2[nH]nc(-c3ccc(CO)cc3)c2c1]

Suzuki procedure E yielded tert-butyl 3-(4-(hydroxymethyl)phenyl)-5-methyl-1H-indazole-1-carboxylate (30 mg, 34%). Standard TFA deprotection conditions gave [4-(5-methyl-2H-indazol-3-yl)phenyl]methanol (5 mg, 24%)

$^1$H NMR (500 MHz, Methanol-d$_4$) δ 7.96-7.88 (m, 2H), 7.79 (d, J=1.6 Hz, 1H), 7.53 (d, J=8.0 Hz, 2H), 7.47 (d, J=8.5 Hz, 1H), 7.29 (dd, J=8.6, 1.4 Hz, 1H), 4.70 (s, 2H), 2.50 (s, 3H).

$^{13}$C NMR (126 MHz, CD$_3$OD) δ 143.92, 141.12, 140.52, 132.62, 130.55, 128.55, 127.05, 127.02, 120.68, 119.38, 109.72, 63.60, 20.18.

Melting point range (° C.): 171-174.

HRMS (ES)): mass calc for C$_{15}$H$_{14}$N$_2$O$^+$ [M+H]$^+$=239.1179, found=239.1178.

3-(2H-1,3-benzodioxol-5-yl)-6-(trifluoromethyl)-2H-indazole (6x)

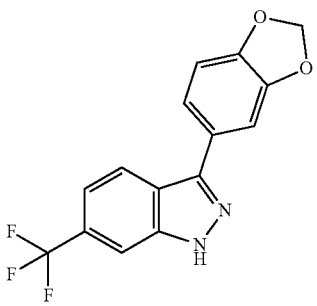 [SMILES: FC(F)(F)c1ccc2c(-c3ccc4c(c3)OCO4)n[nH]c2c1]

Suzuki procedure D yielded tert-butyl 3-(benzo[d][1,3] dioxol-5-yl)-6-(trifluoromethyl)-1H-indazole-1-carboxylate, which was subjected to standard TFA deprotection conditions to give 3-(2H-1,3-benzodioxol-5-yl)-6-(trifluoromethyl)-2H-indazole (5 mg, 17% over 2 steps).

$^1$H NMR (500 MHz, Methanol-d$_4$) δ 8.17 (d, J=8.5 Hz, 1H), 7.90 (s, 1H), 7.46 (td, J=7.7, 1.5 Hz, 2H), 7.42 (d, J=1.6 Hz, 1H), 7.00 (d, J=8.0 Hz, 1H), 6.05 (s, 2H).

$^{13}$C NMR (126 MHz, CD$_3$OD) δ 148.32, 148.00, 144.87, 140.73, 128.28 (q, J=32 Hz), 126.80, 124.60 (q, J=272 Hz), 121.91, 121.36, 121.08, 116.81 (q, J=3 Hz), 108.22, 107.84, 107.26, 101.29.

Melting point range (° C.): 178-180.

HRMS (ES)): mass calc for C$_{15}$H$_9$F$_3$N$_2$O$_2^+$ [M+H]$^+$=307.0689, found=307.0700.

methyl 4-[6-(trifluoromethyl)-2H-indazol-3-yl]benzoate (6y)

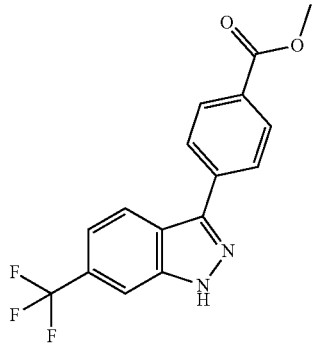 [SMILES: COC(=O)c1ccc(-c2n[nH]c3cc(C(F)(F)F)ccc23)cc1]

Suzuki procedure C yielded methyl 4-(6-(trifluoromethyl)-1H-indazol-3-yl)benzoate (36 mg, 46%).

$^1$H NMR (500 MHz, Methanol-d$_4$) δ 8.27 (d, J=8.6 Hz, 1H), 8.18 (d, J=8.4 Hz, 2H), 8.16-8.08 (m, 2H), 7.95 (s, 1H), 7.51 (dd, J=8.6, 1.6 Hz, 1H), 3.97 (s, 3H).

$^{13}$C NMR (126 MHz, CD$_3$OD) δ 166.84, 143.56, 140.83, 137.59, 129.72, 129.40, 128.35 (q, J=32.07 Hz), 126.87, 124.54 (q, J=271.88 Hz), 122.14, 121.77, 117.41 (q, J=3.10 Hz), 108.09 (q, J=3.87 Hz), 51.29

Melting point range (° C.): 210.7-212.5.

HRMS (ES)): mass calc for C$_{16}$H$_{11}$F$_3$N$_2$O$_2^+$ [M+H]$^+$=321.0845, found=328.0853.

4-[6-(trifluoromethyl)-2H-indazol-3-yl]benzoic Acid (6z)

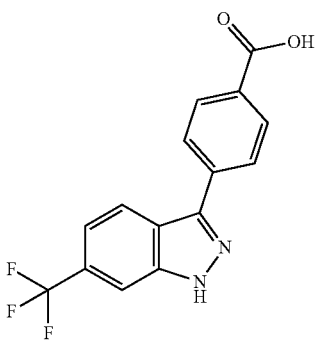 [SMILES: O=C(O)c1ccc(-c2n[nH]c3cc(C(F)(F)F)ccc23)cc1]

Suzuki procedure C gave methyl 4-(6-(trifluoromethyl)-1H-indazol-3-yl)benzoate (36 mg, 46%) after which methyl ester hydrolysis procedure F on 15 mg (47 μmol) of the compound gave 4-(6-(trifluoromethyl)-1H-indazol-3-yl) benzoic acid (9 mg, 63%).

$^1$H NMR (500 MHz, Methanol-d$_4$) δ 8.27 (d, J=8.5 Hz, 1H), 8.22-8.16 (m, 2H), 8.11 (d, J=8.0 Hz, 2H), 7.94 (s, 1H), 7.50 (d, J=8.6 Hz, 1H).

$^{13}$C NMR (126 MHz, CD$_3$OD) δ 168.09, 143.67, 140.84, 137.37, 130.05, 129.97, 128.35 (q, J=32.17 Hz), 126.81, 124.54 (q, J=271.7 Hz), 122.15, 121.80, 117.38 (q, J=3.1 Hz), 108.11 (q, J=4.5 Hz).

Melting point range (° C.): 283-284.5.

HRMS (ES)): mass calc for C$_{15}$H$_9$F$_3$N$_2$O$_2^+$ [M+Na]$^+$=329.0508, found=329.0508.

3-(2H-1,3-benzodioxol-5-yl)-6-chloro-2H-indazole (6aa)

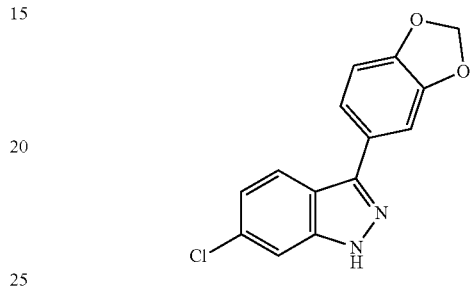

Suzuki procedure D yielded 3-(2H-1,3-benzodioxol-5-yl)-6-chloro-2H-indazole (3 mg, 11%).

$^1$H NMR (500 MHz, Methanol-d$_4$) δ 7.95 (d, J=8.7 Hz, 1H), 7.57 (d, J=1.7 Hz, 1H), 7.42 (dd, J=8.0, 1.7 Hz, 1H), 7.38 (d, J=1.7 Hz, 1H), 7.20 (dd, J=8.7, 1.8 Hz, 1H), 6.99 (d, J=8.0 Hz, 1H), 6.04 (s, 2H).

$^{13}$C NMR (126 MHz, CD$_3$OD) δ 148.27, 147.92, 144.87, 142.16, 132.66, 126.94, 121.87, 121.64, 121.01, 118.89, 109.57, 108.18, 107.23, 101.26.

Melting point range (° C.): 235-237.

HRMS (ES)): mass calc for C$_{14}$H$_9$ClN$_2$O$_2^+$ [M+H]$^+$=273.0425, found=273.0429.

methyl 4-(6-chloro-2H-indazol-3-yl)benzoate (6bb)

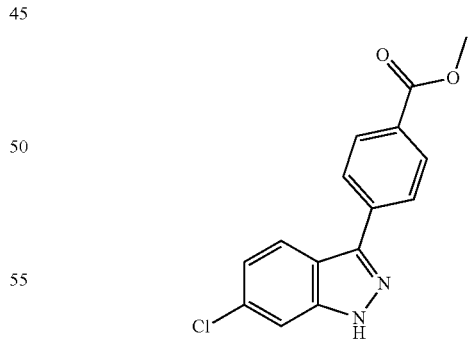

Suzuki procedure D yielded tert-butyl 6-chloro-3-(4-(methoxycarbonyl)phenyl)-1H-indazole-1-carboxylate (100 mg, 30%). TFA deprotection using the standard protocol gave methyl 4-(6-chloro-2H-indazol-3-yl)benzoate (7 mg, 9%).

$^1$H NMR (500 MHz, DMSO-d$_6$) δ 8.17 (m, 3H), 8.11 (m, 2H), 7.72 (d, J=1.7 Hz, 1H), 7.28 (dd, J=8.7, 1.8 Hz, 1H), 3.90 (s, 3H).

$^{13}$C NMR (126 MHz, DMSO) δ 166.47, 142.70, 142.63, 138.12, 131.81, 130.32, 129.12, 127.21, 122.73, 122.58, 119.39, 110.88, 52.66.

Melting point range (° C.): 196.9-198.8.

HRMS (ES)): mass calc for $C_{15}H_{11}ClN_2O_2^+$ [M+H]$^+$=287.0582, found=287.0587.

4-(6-chloro-2H-indazol-3-yl)benzoic Acid (6cc)

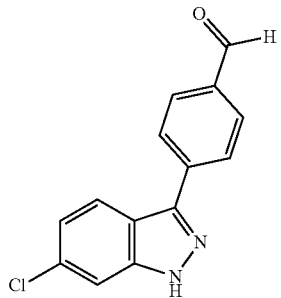 [SMILES: O=Cc1ccc(-c2n[nH]c3cc(Cl)ccc23)cc1]

Suzuki procedure C yielded methyl 4-(6-chloro-1H-indazol-3-yl)benzoate (35 mg, 44%) of which 15 mg (52 μmol) was subjected to methyl ester hydrolysis procedure F to give 4-(6-chloro-1H-indazol-3-yl)benzoic acid (7 mg, 26 umol, 49%).

Note: acidification did not produce a solid. Thus, rather than filtration, a few drops of DMSO were added to the solution and the mixture was purified by reverse phase HPLC eluting with 15-80% acetonitrile in water (0.1% formic acid conditions) to afford the desired product.

$^1$H NMR (500 MHz, Methanol-d$_4$) δ 8.21-8.15 (m, 2H), 8.07 (dd, J=8.5, 3.9 Hz, 3H), 7.63 (d, J=1.6 Hz, 1H), 7.25 (dd, J=8.7, 1.8 Hz, 1H).

$^{13}$C NMR (126 MHz, CD$_3$OD) δ 168.69, 143.71, 142.34, 137.23, 132.73, 130.75, 129.89, 126.73, 122.17, 121.78, 119.13, 109.84.

Melting point range (° C.): 313-316.

HRMS (ES)): mass calc for $C_{14}H_9ClN_2O_2^+$ [M+H]$^+$=273.0425, found=273.0429.

methyl 4-(6-fluoro-2H-indazol-3-yl)benzoate (6dd)

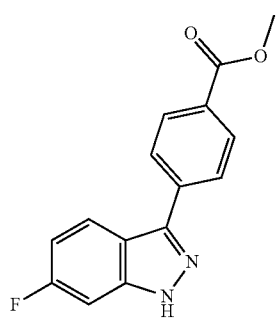 [SMILES: COC(=O)c1ccc(-c2n[nH]c3cc(F)ccc23)cc1]

Suzuki procedure D yielded tert-butyl 6-fluoro-3-(4-(methoxycarbonyl)phenyl)-1H-indazole-1-carboxylate (100 mg, 30%). TFA deprotection under standard conditions gave methyl 4-(6-fluoro-2H-indazol-3-yl)benzoate (10 mg, 12%).

$^1$H NMR (500 MHz, Chloroform-d) δ 8.20-8.10 (m, 2H), 8.04-7.99 (m, 2H), 7.96 (dd, J=9.0, 5.0 Hz, 1H), 7.16 (dd, J=8.8, 2.2 Hz, 1H), 7.03 (td, J=9.0, 2.2 Hz, 1H), 3.95 (s, 3H).

$^{13}$C NMR (126 MHz, CDCl$_3$) δ 166.88, 162.45 (d, J=246.77 Hz), 144.98, 142.06 (d, J=12.76 Hz), 137.50, 130.19, 129.78, 127.26, 122.51 (d, J=10.91 Hz), 118.02, 111.84 (d, J=25.96 Hz), 95.84 (d, J=26.41 Hz), 52.23.

Melting point range (° C.): 220.4-222.1.

HRMS (ES)): mass calc for $C_{15}H_{11}FN_2O_2^+$ [M+H]$^+$=271.0877, found=271.0882.

3-(2H-1,3-benzodioxol-5-yl)-6-fluoro-2H-indazole (6ee)

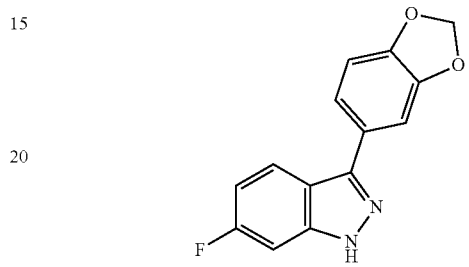

Suzuki procedure D gave tert-butyl tert-butyl 3-(benzo[d][1,3]dioxol-5-yl)-6-fluoro-1H-indazole-1-carboxylate, which was subjected to regular TFA deprotection conditions to give 3-(2H-1,3-benzodioxol-5-yl)-6-fluoro-2H-indazole (5 mg, 18%).

$^1$H NMR (500 MHz, Methanol-d$_4$) δ 7.97 (dd, J=8.9, 5.1 Hz, 1H), 7.42 (dd, J=8.0, 1.7 Hz, 1H), 7.38 (d, J=1.6 Hz, 1H), 7.23 (dd, J=9.3, 2.2 Hz, 1H), 7.06-6.94 (m, 2H), 6.04 (s, 2H).

$^{13}$C NMR (126 MHz, CD$_3$OD) δ 162.38 (d, J=244 Hz), 148.26, 147.89, 144.85, 142.11 (d, J=11 Hz), 127.03, 122.37 (d, J=11 Hz), 121.04, 117.28, 110.43 (d, J=26.4 Hz), 108.17, 107.27, 101.26, 95.15 (d, J=26.46 Hz)

Melting point range (° C.): 183.3-184.4.

HRMS (ES)): mass calc for $C_{14}H_9FN_2O_2^+$ [M+H]$^+$=257.0721, found=257.0726.

4-(6-fluoro-2H-indazol-3-yl)benzoic Acid (6ff)

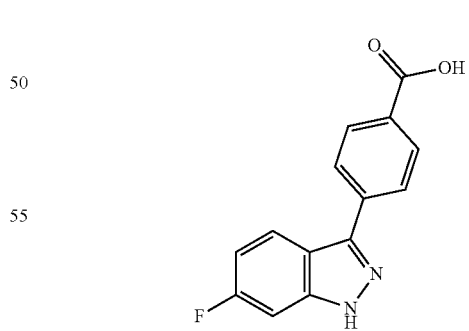

Methyl ester hydrolysis procedure F performed on methyl 4-(6-fluoro-2H-indazol-3-yl)benzoate (10 mg, 0.037 mmol) yielded 4-(6-fluoro-2H-indazol-3-yl)benzoic acid (2 mg, 21%).

$^1$H NMR (500 MHz, Methanol-d$_4$) δ 8.18 (d, J=8.1 Hz, 2H), 8.12-8.02 (m, 3H), 7.28 (m, 1H), 7.10-6.98 (m, 1H).

$^{13}$C NMR (126 MHz, CD$_3$OD) δ 168.91, 162.35 (d, J=244.5 Hz), 143.79, 142.31 (d, J=11.6 Hz), 137.21, 131.04, 129.86, 126.75, 122.29 (d, J=10.91 Hz), 117.50, 110.47 (d, J=26.43 Hz), 95.51.

Melting point range (° C.): 312-314.

HRMS (ES)): mass calc for C$_{14}$H$_9$FN$_2$O$_2^+$ [M+H]$^+$=257.0721, found=257.0729.

REFERENCES

[1] a) C.-T. Hsueh, D. Liu, H. Wang, Biomarker Res. 2013, 1, 1; b) C. Wellbrock, I. Arozarena, Frontiers in cell and developmental biology 2016, 4, 33; c) F. Liu, X. Yang, M. Geng, M. Huang, Acta Pharmaceutica Sinica B 2018, 8, 552; d) A. Whitmarsh, R. Davis, Oncogene 2007, 26, 3172; e) A. Akinleye, M. Furqan, N. Mukhi, P. Ravella, D. Liu, Journal of hematology & oncology 2013, 6, 27; f) B. B. Friday, A. A. Adjei, Clinical Cancer Research 2008, 14, 342-346.

[2] a) Y. Zhao, A. A. Adjei, Nature Reviews Clinical Oncology 2014, 11, 385; b) L. N. Micel, J. J. Tentler, A.-C. Tan, H. M. Selby, K. L. Brunkow, K. M. Robertson, S. L. Davis, P. J. Klauck, T. M. Pitts, E. Gangolli, R. Fabrey, S. M. O'Connell, P. W. Vincent, S. G. Eckhardt, Mol. Cancer Ther. 2015, 14, 317-325; c) E. Poplin, Y. Feng, J. Berlin, M. L. Rothenberg, H. Hochster, E. Mitchell, S. Alberts, P. O'Dwyer, D. Haller, P. Catalano, D. Cella, A. B. Benson, 3rd, J. Clin. Oncol. 2009, 27, 3778-3785.

[3] Z. Xue, D. J. Vis, A. Bruna, T. Sustic, S. van Wageningen, A. S. Batra, O. M. Rueda, E. Bosdriesz, C. Caldas, L. F. Wessels, R. Bernards, Cell Research 2018, 28, 719729.

[4] A. Cuenda, The international journal of biochemistry & cell biology 2000, 32, 581-587.

[5] L. Xu, Y. Ding, W. J. Catalona, X. J. Yang, W. F. Anderson, B. Jovanovic, K. Wellman, J. Killmer, X. Huang, K. A. Scheidt, R. B. Montgomery, R. C. Bergan, Journal of the National Cancer Institute 2009, 101, 1141-1155.

[6] a) B. Derijard, J. Raingeaud, T. Barrett, I. H. Wu, J. Han, R. J. Ulevitch, R. J. Davis, Science 1995, 267, 682-685; b) T. L. Lotan, M. Lyon, D. Huo, J. B. Taxy, C. Brendler, B. A. Foster, W. Stadler, C. W. Rinker-Schaeffer, J. Pathol. 2007, 212, 386-394; c) L. Wang, Y. Pan, J. L. Dai, Oncogene 2004, 23, 5978-5985; d) J. M. Pavese, I. M. Ogden, E. A. Voll, X. Huang, L. Xu, B. Jovanovic, R. C. Bergan, PloS one 2014, 9, e102289.

[7] S. C. Cunningham, E. Gallmeier, T. Hucl, D. A. Dezentje, E. S. Calhoun, G. Falco, K. Abdelmohsen, M. Gorospe, S. E. Kern, Cancer research 2006, 66, 5560-5564.

[8] N. Kim, J. Park, C. G. Gadhe, S. J. Cho, Y. Oh, D. Kim, K. Song, PloS one 2014, 9, e91037.

[9] E. V. Leitao da-Cunha, I. M. Fechine, D. N. Guedes, J. M. Barbosa-Filho, M. Sobral da Silva, in The Alkaloids: Chemistry and Biology, Vol. 62 (Ed.: G. A. Cordell), Academic Press, 2005, pp. 1-75.

[10] a) D. E. Lee, K. W. Lee, S. Byun, S. K. Jung, N. Song, S. H. Lim, Y.-S. Heo, J. E. Kim, N. J. Kang, B. Y. Kim, T. Bowden, G., A. M. Bode, H. J. Lee, Z. Dong, Journal of Biological Chemistry 2011, 286, 14246; b) L. Xu, R. Gordon, R. Farmer, A. Pattanayak, A. Binkowski, X. Huang, M. Avram, S. Krishna, E. Voll, J. Pavese, J. Chavez, J. Bruce, A. Mazar, A. Nibbs, W. Anderson, L. Li, B. Jovanovic, S. Pruell, M. Valsecchi, G. Francia, R. Betori, K. Scheidt, R. Bergan, Nature Communications 2018, 9, 2454.

[11] K. K. Deibler, R. K. Mishra, M. R. Clutter, A. Antanasijevic, R. Bergan, M. Caffrey, K. A. Scheidt, ACS chemical biology 2017, 12, 1245-1256.

[12] a) S. L. McGovern, B. T. Helfand, B. Feng, B. K. Shoichet, J. Med. Chem. 2003, 46, 4265-4272; b) J. J. Irwin, D. Duan, H. Torosyan, A. K. Doak, K. T. Ziebart, T. Sterling, G. Tumanian, B. K. Shoichet, J. Med. Chem. 2015, 58, 7076-7087.

[13] Z. A. Knight, K. M. Shokat, Chemistry & biology 2005, 12, 621-637.

[14] S. N. Krishna, C. H. Luan, R. K. Mishra, L. Xu, K. A. Scheidt, W. F. Anderson, R. C. Bergan, PloS one 2013, 8, e81504.

[15] a) T. A. Halgren, R. B. Murphy, R. A. Friesner, H. S. Beard, L. L. Frye, W. T. Pollard, J. L. Banks, J. Med. Chem. 2004, 47, 1750-1759; b) N. Schrodinger LLC Small-Molecule Drug Discovery Suite 2014-4: Glide, version 6.5, Schrödinger, LLC, New York, N.Y., 2014, 2014.

[16] S. D. Bembenek, G. Hirst, T. Mirzadegan, J. Chem. Inf. Model. 2018, 58, 1434-1440.

Example II

Title—Design, Synthesis, and Evaluation of MEK4 Inhibitors Against Metastatic Pancreatic Ductal Adenocarcinoma Pancreatic ductal adenocarcinoma (PDAC) represents 85% of all diagnosed pancreatic cancers and is the fourth most common cause of cancer death. The mortality rate is >90% a few years after diagnosis. Because there are no distinct symptoms in early stages, >50% of diagnosed patients have metastatic disease. The current best treatment is resection of the tumor, which is not an option for metastatic tumors.

MMP-2 has been studied as a potential target for treating PDAC due to its direct role in metastasis. However, previous attempts to develop an MMP-2 inhibitor have failed due to low efficacy and high toxicity. Because MEK4 is part of an upstream enzyme cascade for activating MMP-2, we selected MEK4 as a therapeutic target. Studies in mice have shown that MEK4-cell lines exhibit smaller tumor growth and lower metastatic potential in comparison to MEK4$^+$ cell lines. (See Cunningham et al. Cancer Res. 2006, 66, 5560).

As such, we attempted to design irreversible inhibitors of MEK4 kinase as a target for treating cancers such as PDAC. Our preliminary cellular assays revealed that a reversible inhibitor exhibited attenuated potency.

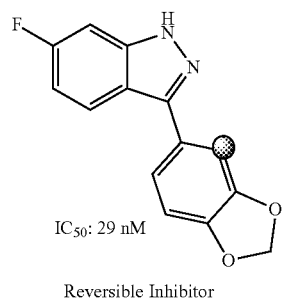 [SMILES: Fc1ccc2c(-c3ccc4c(c3)OCO4)n[nH]c2c1]

IC$_{50}$: 29 nM

Reversible Inhibitor

We suspected that the reversible inhibitor was outcompeted by ATP for binding to MEK4 and we set out to design a covalent inhibitor using structure-guided design based on a modeled binding of the reversible inhibitor near Cys 246.

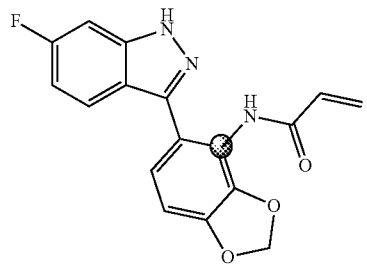

Covalent Inhibitor

Figure 6:
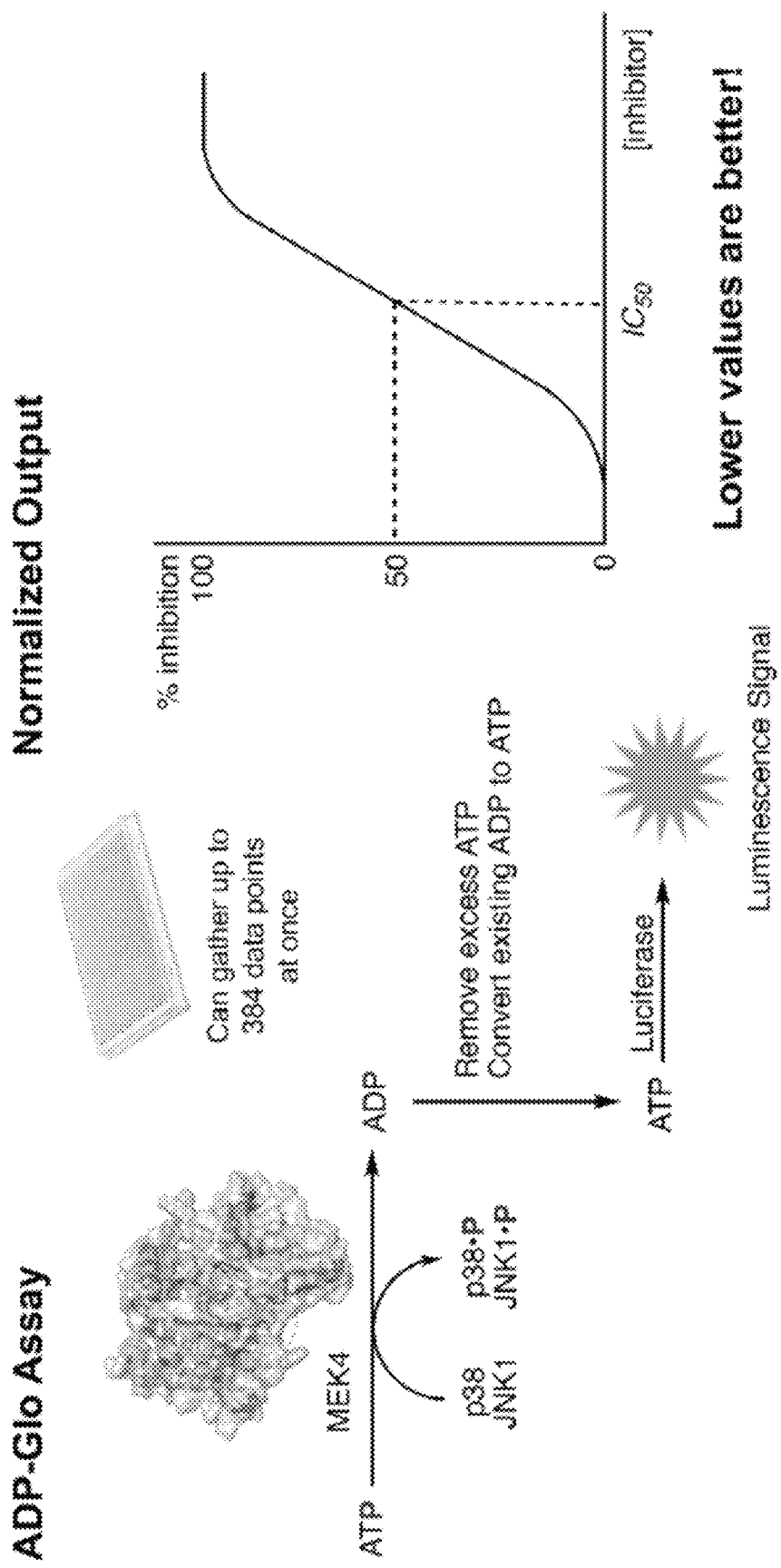
FIG. 6. Illustration of ADP-Glo assay for assessing MEK4 inhibition.
Figure 7:
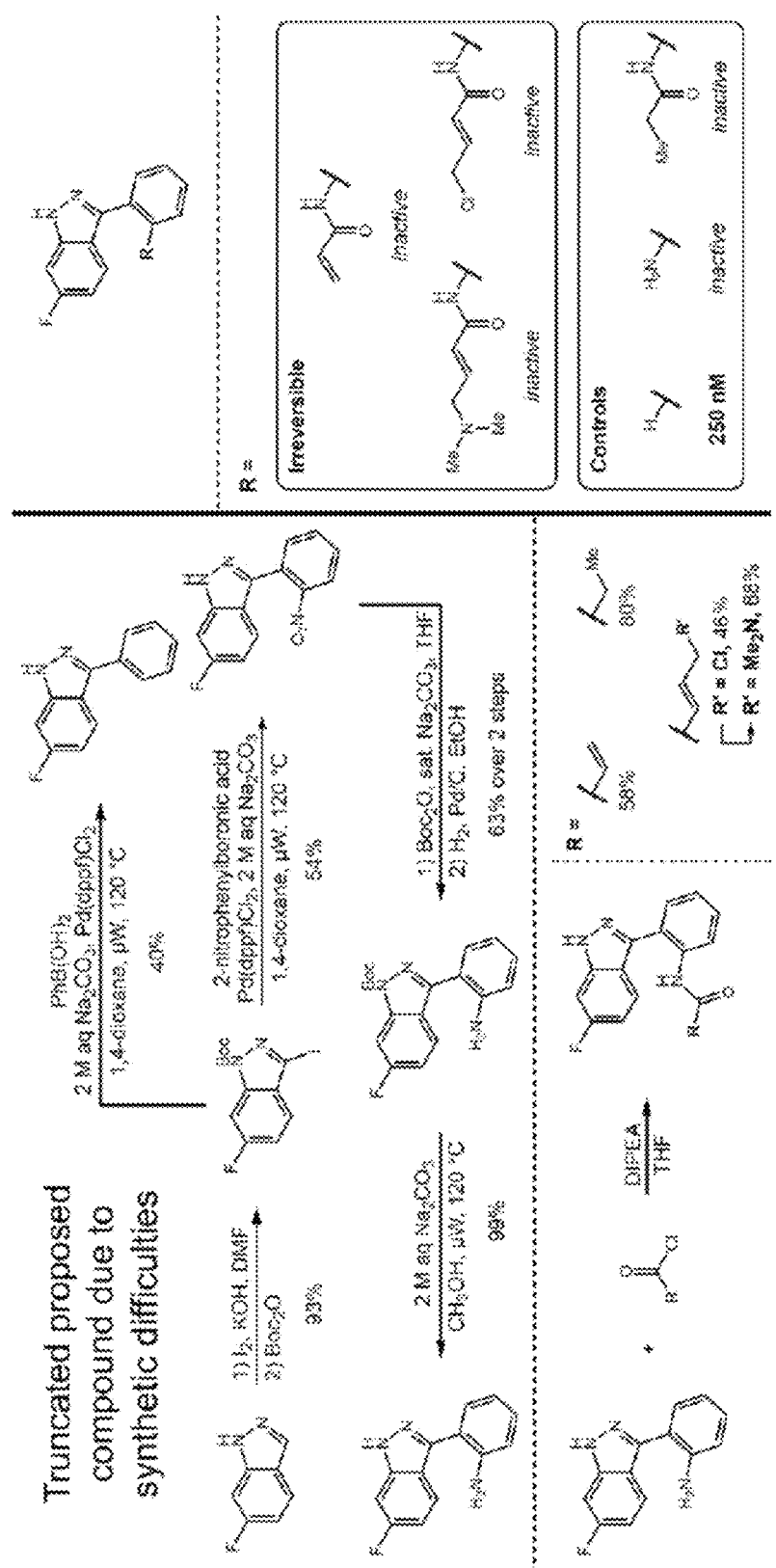
FIG. 7. Irreversible inhibitors and sample synthesis.
Figure 8:
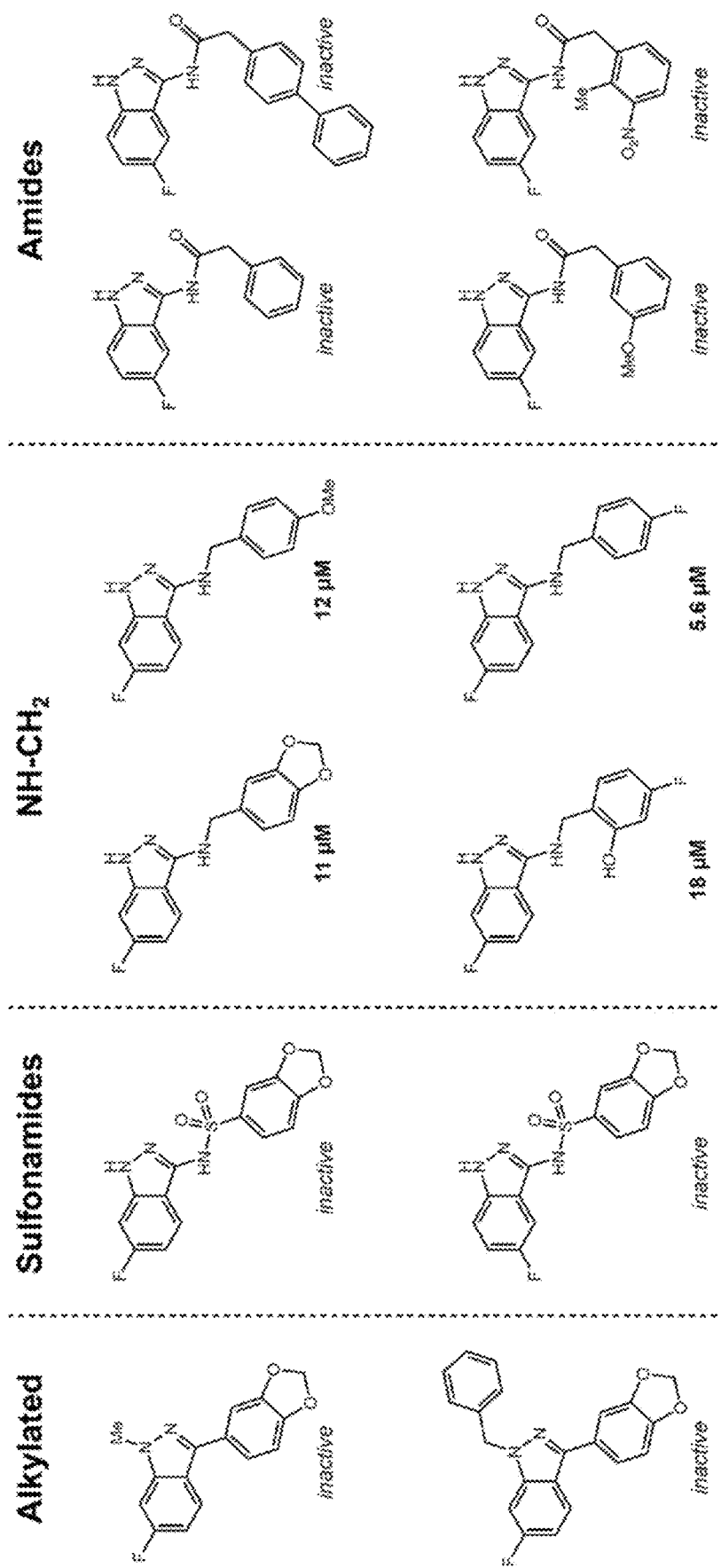
FIG. 8. Reversible inhibitors.
Figure 9:
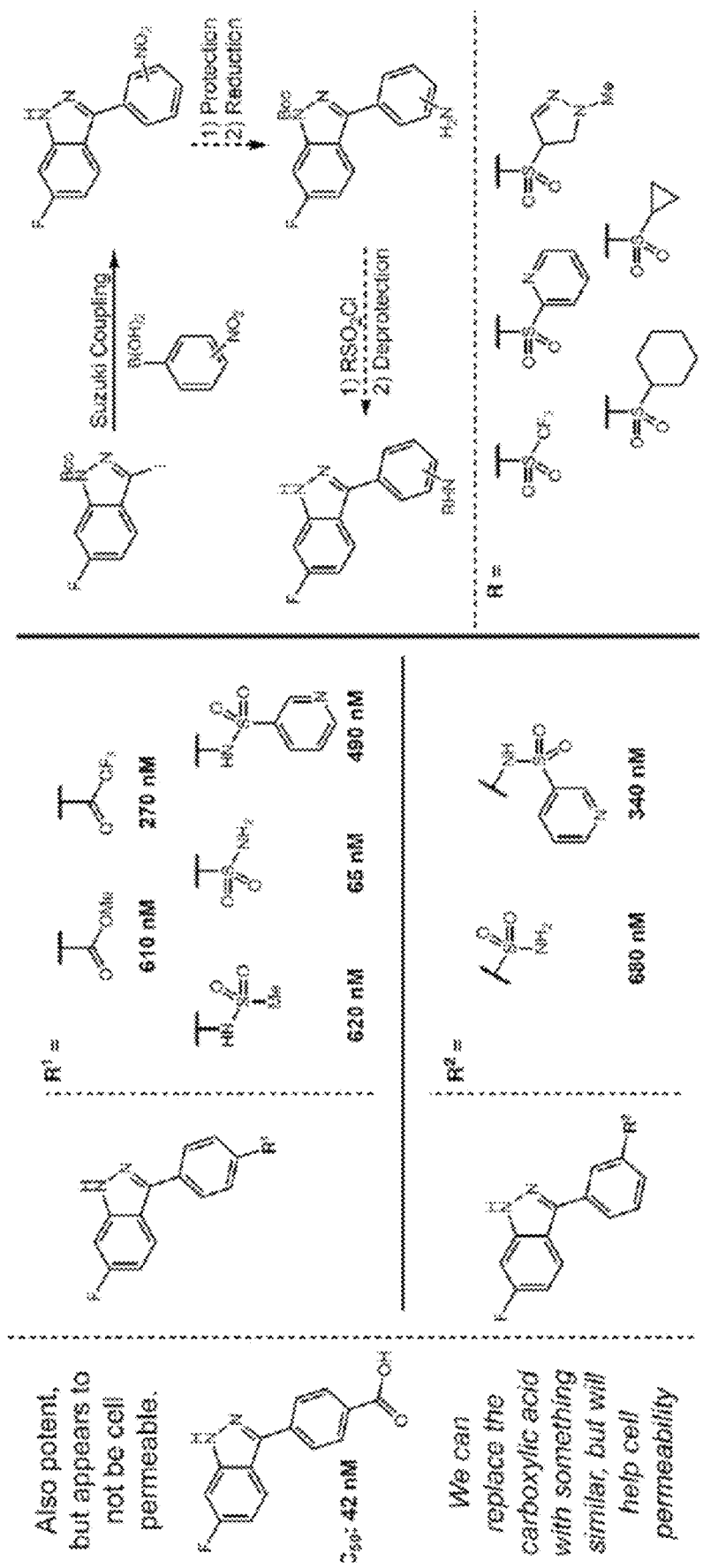
FIG. 9. Bioisostere inhibitors.

In order to evaluate the compounds as inhibitors of MEK4, we designed an ADP-Glo assay as illustrated in FIG. 6. Percent inhibition of MEK4 was determined based on a compounds ability to inhibit MEK4 phosphorylation of p38 and JNK1. Irreversible inhibitors and sample synthesis is illustrated in FIG. 7. Additional reversible inhibitors are illustrated in FIG. 8. Bioisostere inhibitors and derivatives are illustrated in FIG. 9.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A compound of the following formula or a salt or hydrate thereof:

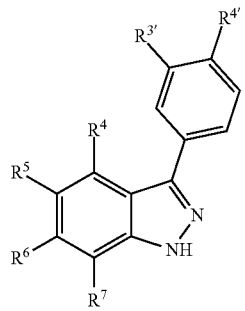

where:
$R^4$, $R^5$, and $R^6$ are independently selected from hydrogen, alkyl, halogen, and haloalkyl;
$R^{3'}$ is selected from hydrogen, carboxyl, hydroxymethyl, and carboxamido; and
$R^{4'}$ is selected from hydrogen, hydroxyl, carboxamido, hydroxymethyl, 2-hydroxy-2-propyl, carboxyl, and methyl carboxyl ester;
wherein at least one of $R^{3'}$ and $R^{4'}$ is not hydrogen.

2. The compound of claim 1, wherein $R^6$ is halogen.

3. The compound of claim 1, wherein $R^{4'}$ is carboxyl.

4. The compound of claim 1, wherein the compound is:

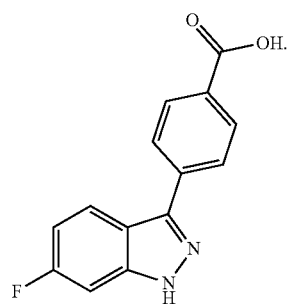 [SMILES: O=C(O)c1ccc(-c2n[nH]c3cc(F)ccc23)cc1]

5. The compound of claim 1 of a formula selected from:

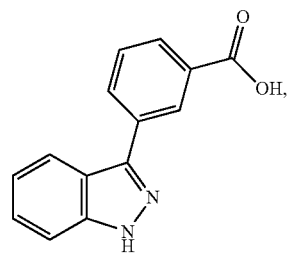

69
-continued
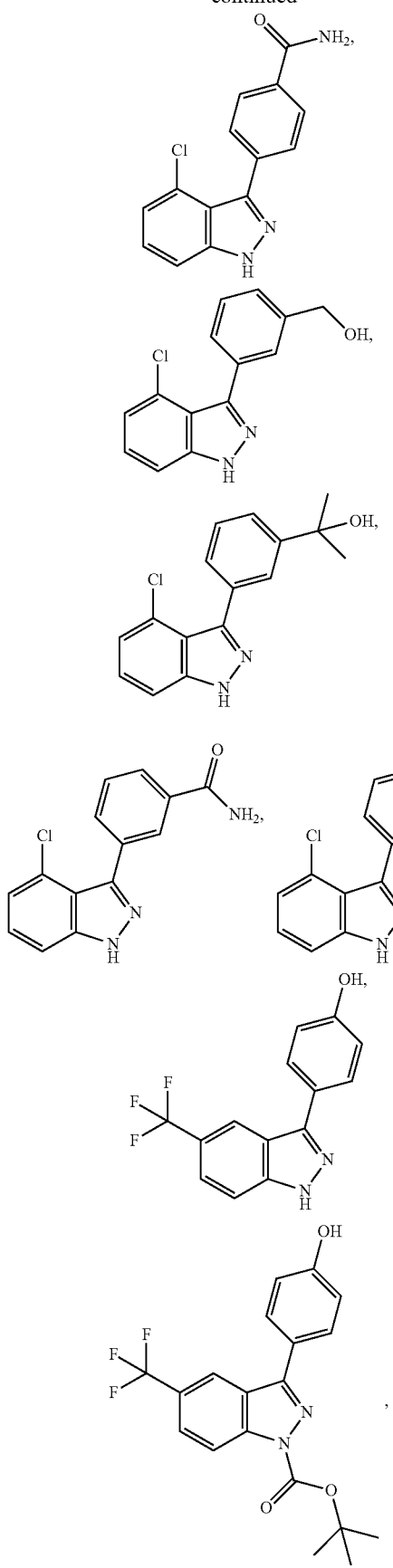
70
-continued
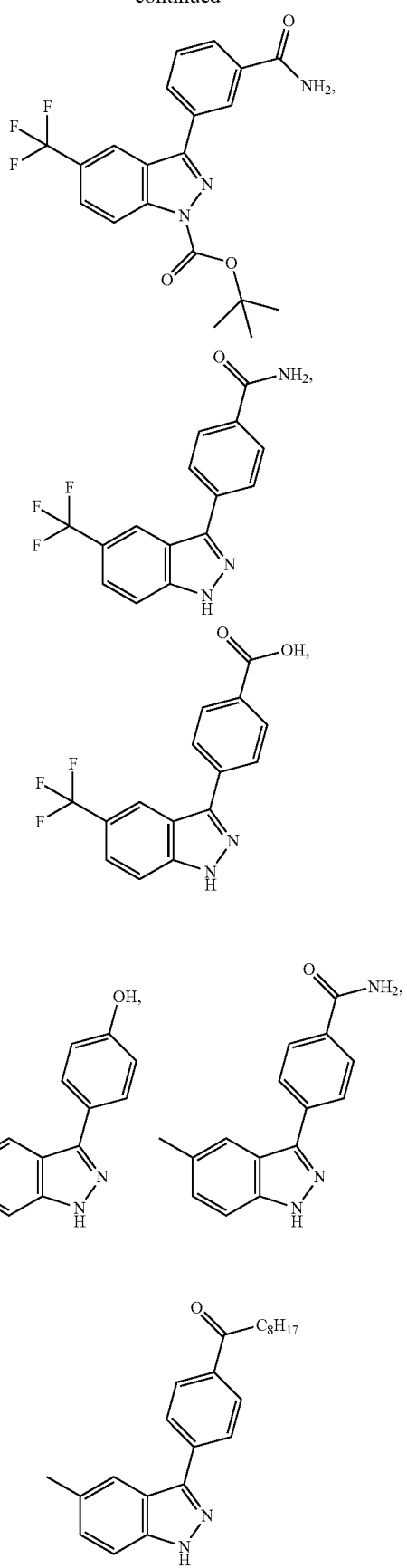

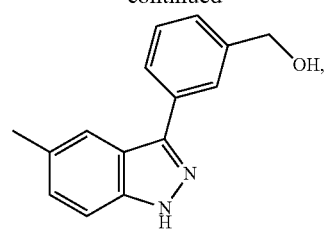

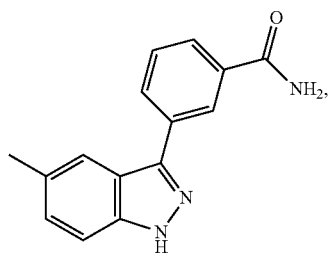

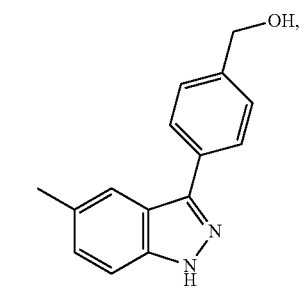

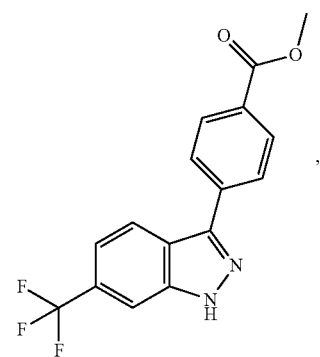

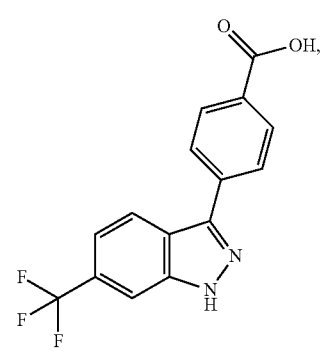

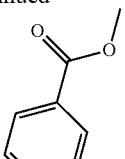

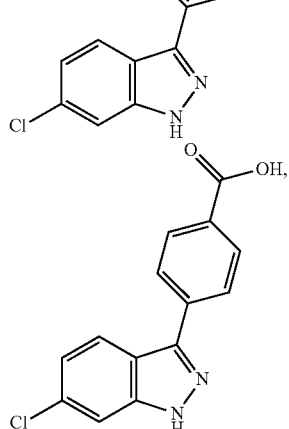

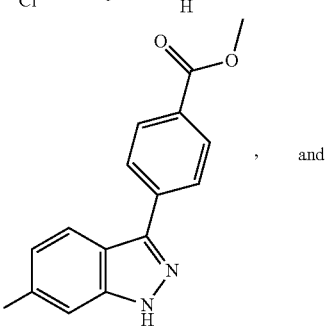

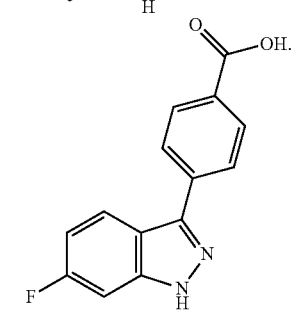

6. A pharmaceutical composition comprising the compound of claim 1 and a pharmaceutical carrier, excipient, or diluent.

7. A pharmaceutical composition comprising the compound of claim 5 and a pharmaceutical carrier, excipient, or diluent.

8. A method for treating a cancer characterized by increased disease or disorder associated with mitogen-activated protein kinase 4 (MEK4) activity in a subject in need thereof, the method comprising administering to the subject the pharmaceutical composition of claim 6 and delivering an effective amount of the compound to inhibit MEK4 activity in the subject.

9. The method of claim 8, wherein the cancer is prostate cancer.

10. The method of claim 8, wherein the cancer is breast cancer.

11. The method of claim 8, wherein the cancer is pancreatic cancer.

12. The method of claim 8, wherein the cancer is colon cancer.

13. The compound of claim 1, wherein at least one of $R^4$, $R^5$, and $R^6$ is not hydrogen.

14. A compound of the following formula or a salt or hydrate thereof:

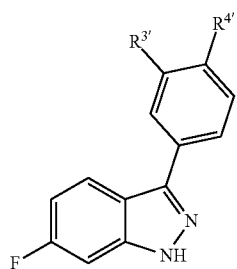

wherein:

$R^{3'}$ is hydrogen, and $R^4$ is selected from carboxyl and methyl carboxyl ester; or $R^{3'}$ and $R^4$ are linked together and are —O—CH$_2$—O—.

15. The compound of claim 14, wherein $R^{3'}$ is hydrogen and $R^{4'}$ is carboxyl.

16. The compound of claim 14, wherein $R^{3'}$ and $R^4$ are linked together and are —O—CH$_2$—O—.

17. The compound of claim 14, wherein the compound is:

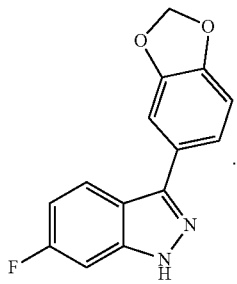 [SMILES: Fc1ccc2c(-c3ccc4c(c3)OCO4)n[nH]c2c1]

18. The compound of claim 14, wherein the compound is:

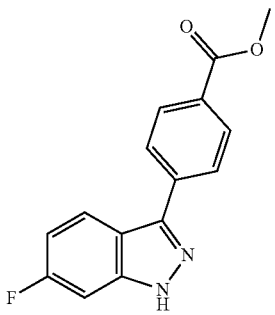

19. The compound of claim 14, wherein the compound is:

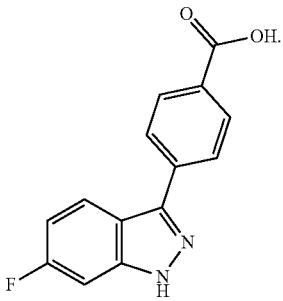 [SMILES: O=C(O)c1ccc(-c2n[nH]c3cc(F)ccc23)cc1]

20. A pharmaceutical composition comprising the compound of claim 14 and a pharmaceutical carrier, excipient, or diluent.

21. A method for treating a cancer characterized by increased mitogen-activated protein kinase 4 (MEK4) activity in a subject in need thereof, the method comprising administering to the subject the pharmaceutical composition of claim 20 and delivering an effective amount of the compound to inhibit MEK4 activity in the subject.

22. The method of claim 21, wherein the cancer is prostate cancer.

23. The method of claim 21, wherein the cancer is breast cancer.

24. The method of claim 21, wherein the cancer is pancreatic cancer.

25. The method of claim 21, wherein the cancer is colon cancer.

* * * * *